United States Patent
Tsourkas et al.

(10) Patent No.: US 12,187,809 B2
(45) Date of Patent: Jan. 7, 2025

(54) PROXIMITY-BASED SORTASE-MEDIATED PROTEIN PURIFICATION AND LIGATION

(71) Applicant: THE TRUSTEES OF THE UNIVERSITY OF PENNSYLVANIA, Philadelphia, PA (US)

(72) Inventors: Andrew Tsourkas, Bryn Mawr, PA (US); Burcin Altun, Philadelphia, PA (US); Hejia Henry Wang, Philadelphia, PA (US); Feifan Yu, Aberdeen, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 197 days.

(21) Appl. No.: 17/588,205

(22) Filed: Jan. 28, 2022

(65) Prior Publication Data

US 2022/0235145 A1    Jul. 28, 2022

Related U.S. Application Data

(62) Division of application No. 16/333,196, filed as application No. PCT/US2017/051636 on Sep. 14, 2017, now Pat. No. 11,236,177.

(60) Provisional application No. 62/394,430, filed on Sep. 14, 2016.

(51) Int. Cl.
| | |
|---|---|
| *C07K 16/40* | (2006.01) |
| *C07K 1/14* | (2006.01) |
| *C07K 7/06* | (2006.01) |

(52) U.S. Cl.
CPC .............. *C07K 16/40* (2013.01); *C07K 1/14* (2013.01); *C07K 7/06* (2013.01); *C07K 2317/622* (2013.01); *C07K 2319/20* (2013.01); *C07K 2319/21* (2013.01); *C07K 2319/22* (2013.01); *C07K 2319/70* (2013.01); *C07K 2319/73* (2013.01); *C07K 2319/92* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 5,013,556 A | 5/1991 | Woodle et al. |
| 7,238,489 B2 | 7/2007 | Schneewind et al. |
| 9,631,218 B2 | 4/2017 | Tsourkas et al. |
| 2014/0030697 A1 | 1/2014 | Ploegh et al. |
| 2015/0086576 A1 | 3/2015 | Ploegh et al. |
| 2016/0032346 A1 | 2/2016 | Tsourkas et al. |

FOREIGN PATENT DOCUMENTS

| | | |
|---|---|---|
| WO | WO 1997/38731 | 10/1997 |
| WO | WO 2013/003555 | 1/2013 |
| WO | WO 2014/183066 | 11/2014 |
| WO | WO 2016/183387 | 5/2016 |

OTHER PUBLICATIONS

Chivers et al., Nature Methods 7(5): 391-393 (Year: 2010).*
Chen et al., PNAS 108(28): 11399-11404 (Year: 2011).*
Almquist, et al. "Synthesis and biological activity of a ketomethylene analog of a tripeptide inhibitor of angiotensin converting enzyme." Journal of medicinal chemistry 23.12 (1980): 1392-1398.
Beerli, Roger R., et al. "Sortase enzyme-mediated generation of site-specifically conjugated antibody drug conjugates with high in vitro and in vivo potency." PloS one 10.7 (2015): e0131177.
Bird et al. "Single-chain antigen-binding proteins." Science 242. 4877 (1988): 423-426.
Chari, et al. "Immunoconjugates containing novel maytansinoids: promising anticancer drugs." Cancer research 52.1 (1992): 127-131.
Edwards, et al. "The remarkable flexibility of the human antibody repertoire; isolation of over one thousand different antibodies to a single protein, BLyS." Journal of molecular biology 334.1 (2003): 103-118.
Fernández-Suárez et al., "Protein—protein interaction detection in vitro and in cells by proximity biotinylation." Journal of the American Chemical Society 130.29 (2008): 9251-9253.
Gabizon et al., "Pharmacokinetics and tissue distribution of doxorubicin encapsulated in stable liposomes with long circulation times." JNCI: Journal of the National Cancer Institute 81.19 (1989): 1484-1488.
Hann, et al. "On the double bond isostere of the peptide bond: preparation of an enkephalin analogue." Journal of the Chemical Society, Perkin Transactions 1 (1982): 307-314.
Holladay et al., "Synthesis of hydroxyethylene and ketomethylene dipeptide isosteres." Tetrahedron Letters 24.41 (1983): 4401-4404.
Hruby, V.J., Conformational restrictions of biologically active peptides via amino acid side chain groups. Life sciences 31.3 (1982): 189-199.
Hudson et al., "Methionine enkephalin and isosteric analogues I. Synthesis on a phenolic resin support." International Journal of Peptide and Protein Research 14.3 (1979): 177-185.
Hunkapiller and Hood. "Immunology: the growing immunoglobulin gene superfamily." Nature 323.6083 (1986): 15-16.
Huston et al., "Protein engineering of antibody binding sites: recovery of specific activity in an anti-digoxin single-chain Fv analogue produced in *Escherichia coli*." Proceedings of the National Academy of Sciences 85.16 (1988): 5879-5883.
Hwang et al., "Hepatic uptake and degradation of unilamellar sphingomyelin/cholesterol liposomes: a kinetic study." Proceedings of the National Academy of Sciences 77.7 (1980): 4030-4034.
Iain et al., "In vivo polyester immobilized sortase for tagless protein purification", Microbial Cell Factories, vol. 14, No. 1, Nov. 25, 2015, pp. 1-7.

(Continued)

*Primary Examiner* — Phuong Huynh
(74) *Attorney, Agent, or Firm* — Mark S. Cohen; PEARL COHEN ZEDEK LATZER BARATZ LLP

(57) ABSTRACT

The invention relates to proximity-based sortase-mediated protein purification and ligation. Specifically, the invention relates to techniques that links protein expression/purification with conjugation to therapeutic agents, imaging agents, or linkers.

7 Claims, 18 Drawing Sheets

Specification includes a Sequence Listing.

(56) References Cited

OTHER PUBLICATIONS

International Preliminary Report on Patentability from PCT Patent Application No. PCT/US2017/051636 dated May 16, 2019.
Jennings-White et al., "Synthesis of ketomethylene analogs of dipeptides." Tetrahedron Letters 23.25 (1982): 2533-2534.
Lanzavecchia et al., "The use of hybrid hybridomas to target human cytotoxic T lymphocytes." European journal of immunology 17.1 (1987): 105-111.
Lloyd, et al. "Modelling the human immune response: performance of a 1011 human antibody repertoire against a broad panel of therapeutically relevant antigens." Protein Engineering, Design & Selection 22.3 (2009): 159-168.
O'Shea et al., "Peptide 'Velcro': design of a heterodimeric coiled coil." Current Biology 3.10 (1993): 658-667.
Reminington's Pharmaceutical Sciences, 16th Edition, Osol, A. Ed., 1980.
Spatola, et al. "Structure-activity relationships of enkephalins containing serially replaced thiomethylene amide bond surrogates." Life Sciences 38.14 (1986): 1243-1249.
Stella et al., "Prodrugs, A Chemical Approach to Targeted Drug Delivery", Directed Drug Delivery, Borchardt et al. (ed). 247-267, Humana Press 1985.
Supplementary European Search Report from EP17851555 dated Jun. 17, 2020.
Warden-Rothman et al., Sortase-Tag Expressed Protein Ligation: Combining Purification and Site-Specific Bioconjugation into a Single Step, Analytical Chemistry, vol. 85, No. 22, Oct. 28, 2013, pp. 11090-11097.
Zakeri et al., "Peptide Tag Forming a Rapid Covalent Bond to a protein, through engineering a bacterial adhesin", PNAS (2012, vol. 109, No. 12, 2012, pp. E690-E697. DOI: 10.1073/pnas. 1115485109.

\* cited by examiner

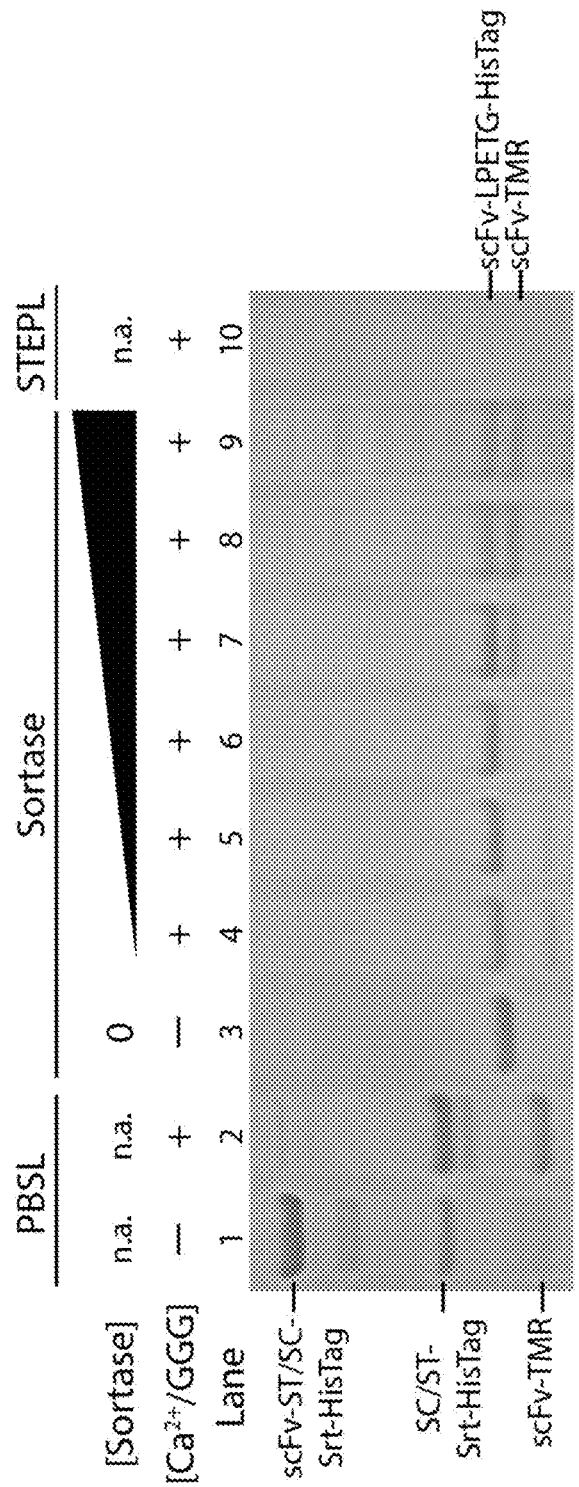
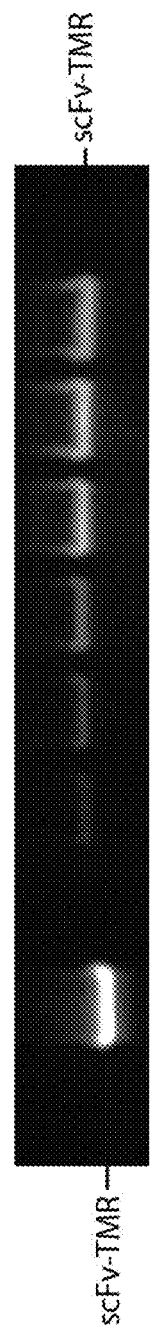
Figure 14A
Figure 14B

PROXIMITY-BASED SORTASE-MEDIATED PROTEIN PURIFICATION AND LIGATION

CROSS-REFERENCE TO RELATED APPLICATIONS

This application is a divisional application of Ser. No. 16/333,196, filed Mar. 13, 2019 (to issue as U.S. Pat. No. 11,236,177), which is U.S. National Phase Application of PCT International Application No. PCT/US2017/051636, International Filing Date Sep. 14, 2017, claiming the benefit of U.S. Patent Application(s) No(s). 62/394,430, filed Sep. 14, 2016, each of which is hereby incorporated by reference.

GOVERNMENT INTEREST STATEMENT

This invention was made with government support under grant numbers R21-EB018863 and R21-CA187657 awarded by the National Institutes of Health. The government has certain rights in the invention.

FIELD OF THE INVENTION

The invention relates to proximity-based, sortase-mediated protein purification and ligation. Specifically, the invention relates to techniques that link protein purification with conjugation to other agents, including therapeutic agents, imaging agents, or linkers.

BACKGROUND OF THE INVENTION

In many basic science, commercial or clinical applications, it is necessary to label a protein with a cargo. The cargo can be a biomolecule, a drug, an imaging agent, a chemical moiety (e.g., hapten, click chemistry molecule, etc.) or other compounds. While many bioconjugation approaches exist to prepare protein-cargo conjugates, the method used can significantly impact the function of the protein and/or cargo as well as the homogeneity of the resulting conjugate. For example, the number and location of cargo can vary significantly from protein to protein.

One of the most widely used approaches for conjugating cargo onto a protein involves the use of N-hydroxysuccinimide (NHS) chemistry. This chemistry allow for the labeling of primary amines. Since primary amines are randomly located throughout the protein, the resulting products are heterogeneous with respect to the number and location of drugs on each protein. The conjugation efficiencies are also generally poor, since hydrolysis is a competing reaction. Similarly, free thiol groups (normally present on cysteines) can be labeled via maleimide- or other thiol-reactive chemistries, but this approach has the same shortcomings as NHS-chemistry.

Thiol groups or click-chemistry groups (e.g., azides and alkynes) can be introduced onto proteins using chemicals, such as N-succinimidyl S-acetylthioacetate (SATA) or NHS-azide, respectively, to create a unique handle for bioconjugation; however, these approaches are also non-site specific, so the protein conjugates are still heterogeneous. Thiolated proteins have the additional shortcoming of being prone to undesirable disulfide formation, aggregation, and precipitation.

Recently, a number of bioconjugation techniques have been established that enable the site-specific labeling of a protein with cargo. These approaches provide control over both the location and number of cargo groups per protein. This can lead to highly homogeneous conjugates with improved functionality. For example, the ability to site-specifically label an antibody such that it is oriented properly when immobilized onto a surface can lead to a 10-1000-fold improvement in immunoassay sensitivity.

Improving the homogeneity of antibody-drug conjugates (ADCs), through site-specific labeling techniques, can also dramatically impact function. Traditionally, drugs have been conjugated to antibodies either through solvent accessible lysines or cysteines that have been made available upon the reduction of interchain disulfide bonds. Both techniques result in highly heterogeneous populations of ADCs, since both the drug load and conjugation site can vary from molecule to molecule. Unfortunately, each species can have distinct therapeutic and pharmacokinetic properties. Some subpopulations can show little, if any, therapeutic activity yet can account for most of the toxicity. These shortcomings can be overcome by implementing methods that allow for the site-specific conjugation of drugs. It has already been demonstrated that site-specific conjugation methods can significantly improve efficacy and safety profiles. For example, antibodies that were site-specifically labeled with two drugs performed equally as well as antibodies that were randomly labeled with an average of 3.5 drugs or even 8 drugs.

Currently, there are four general approaches that have been utilized for the site-specific labeling of antibodies (and other proteins) with drugs. These approaches entail: (i) using unnatural amino acids (UAAs), (ii) introducing cysteine-tags into the genetic code of IgG, (iii) adding peptide tags that are recognized and modified with enzymes (e.g., formylglycine generating enzyme or transglutaminase), and (iv) enzymatically modifying glycans (i.e. glycotransferase).

The use of unnatural amino acids (UAA) to create site-specific ADCs (or other protein-conjugates) offer the most flexibility in terms of selecting an optimal drug location. Unnatural amino acids lead to minimal structural perturbation and therefore can be inserted nearly anyway along the antibody. However, antibody production can be technically complicated, with final conjugation steps that can take up to 4 days. Moreover, since amber stop codon usage in mammalian cells is relatively high, a heterogeneous mixture of antibodies with falsely-incorporated natural amino acids is produced, which makes purification very complicated. One of the most significant limitations of introducing UAAs is that IgG production yields can be significantly lower than wild-type antibodies. Cell-free systems have been developed to avoid some of the complexity issues, but antibody titers are even lower and the resultant antibodies are aglycosylated. Therefore, they are likely to have reduced effector function and less structural stability.

ADCs that require introducing thiols have the advantage of being compatible with maleimide chemistry (and variations thereof), which is well established and can result in highly stable and hydrophilic drug linkages, which has been shown to improve pharmacokinetics and therapeutic index. The challenge with introducing thiols is that these approaches require careful handling to prevent intermolecular crosslinks, triple light chain species, and aggregates from forming. Working with proteins that possess free thiols can therefore be very challenging.

There are a number of site-specific ADC approaches that require introducing a short genetic sequence into the antibody that once translated acts as a substrate for a modifying enzyme. For example, the peptide substrate for formylglycine generating enzyme (FGE) can be introduced to guide the site-specific incorporation of a free aldehyde onto IgG, which can subsequently be labeled with a drug. The peptide substrate for transglutaminase allows for site-specific transamination, and sortase can form an amide-bond between its peptide-substrate and any molecule with an N-terminal glycine. For each of these methods, except sortase, a tag can be inserted at various sites within the antibody backbone and labeled with a drug using the aforementioned enzymes. Sortase is limited to the C-terminus. Unfortunately, enzyme conversion efficiency can be quite variable with these techniques and the conversion efficiency, structural stability, and pharmacokinetics are site-dependent. In the case of FGE, the drug must be attached via an aldehyde, which typically creates an unstable linkage. Pictet-Spengler-reacting tryptamines can be more stable, but these linkages are more hydrophobic and can negatively impact pharmacokinetics and efficacy. In the case of sortase, the efficiency of antibody labeling could be well below 100%, typically ~60%.

Methods that are used to modify the glycans on IgG represent the last major approach that has been adopted to make site-specific ADCs. Most of these methods do not require any antibody engineering, thus any off-the-shelf IgG can be used. However, since glycosylation is a heterogeneous modification, it is very challenging to produce homogeneous ADCs via this approach. Moreover, changing the glycosylation pattern of antibodies can lead to an immunogenic response in humans, which has already been found to be the case for several unnatural sialic acid derivatives.

Intein-mediated expressed protein ligation (EPL) is a technique developed to attach a short synthetic peptide, which can be labeled with the desired cargo, to the N or C-terminus of a recombinantly expressed protein. Unfortunately, intein-mediated EPL's dependence on thioesters prohibits using the technique with proteins that contain disulfides, a significant limitation. Another problem with intein-mediated EPL is that the ligated and unligated proteins remain in the same mixture and additional purification is often required to obtain the protein-conjugate in high purity.

Sortase (Srt) has already been used for a number of protein engineering tasks, including protein purifications and conjugations, including the preparation of ADCs. Sortase A (SrtA) is a calcium-assisted transpeptidase that is responsible for anchoring surface proteins to the peptidoglycan cell wall of Gram-positive bacteria. The enzyme cleaves the peptide bond between the amino acids T and G, within the motif, LPXTG. The products remain transiently attached to SrtA, until the N-terminal glycine of another protein displaces the C-terminal fragment and forms a new peptide bond between the two peptide chains.

By placing an LPXTG motif between a sortase (e.g., sortase A [SrtA]) and a protein of interest (SrtA is upstream of the protein in this case—i.e. at the N-terminus), a calcium triggered self-cleaving peptide can be created, leaving only an N-terminal glycine behind on the protein of interest.

Another common use of SrtA involves expressing a protein of interest with a C-terminal LPXTG tag. The transpeptidase is then added to this sample and used to link a short peptide, beginning with glycine and containing a cargo, to the LPXTG tag. Unfortunately, this reaction is inefficient, resulting in a ligation efficiency that is typically ~60%, even if the sortase is added in a large molar excess of the LPXTG substrate.

More recently, a conjugation method, sortase-tag expressed protein ligation (STEPL), has been developed for simultaneous purification or ligation. STEPL utilizes a single-construct nucleic acid having a coding sequence of a ligand in series with a sortase recognition (e.g., LPXTG), a sortase (e.g., SrtA), and an affinity tag (e.g., a histidine tag [His tag]). After expressing and capturing the protein on an affinity column, calcium and a peptide or protein with an N-terminal glycine (and cargo, if desired) allows the sortase to catalyze ligand release and conjugation of the released ligand to the peptide or protein with an N-terminal glycine, as described in U.S. Pat. No. 9,631,218, issued Apr. 25, 2017, and which is incorporated by reference herein in its entirety. The STEPL protocol was used to conjugate targeting ligands to fluorophores for imaging and/or an azide for subsequent copper-free click chemistry reactions with azadibenzocyclooctyne (ADIBO)-functionalized superparamagnetic iron oxide nanoparticles, demonstrating the system's flexibility, efficacy, and utility.

Using a sortase fused directly to the expressed protein works well with shorter proteins. However, in some instances, the sortase interferes with the proper folding of larger or more complex proteins (e.g., scFv proteins), thereby disrupting secondary structure. In addition, this approach may be incompatible with protein expression systems where calcium is present (e.g., yeast and mammalian systems). Accordingly, there exists a need for improved techniques for protein purification and conjugation.

SUMMARY OF THE INVENTION

According to one aspect, provided herein are conjugate protein compositions comprising a first component protein and a second component protein, wherein: (i) the first component protein comprises a protein of interest in series with a sortase recognition sequence and a first binding pair partner; and (ii) the second component protein comprises a second binding pair partner in series with a sortase and a second component affinity tag having a selective affinity for a second component affinity tag resin, wherein the first binding pair partner and the second binding pair partner comprise two protein moieties that form a first heterodimer. In some embodiments, the second binding pair partner is N-terminal to the sortase and the sortase is N-terminal to the second component affinity tag. In some embodiments, the sortase is N-terminal to the second binding pair partner and the second binding pair partner is N-terminal to the second component affinity tag.

According to another aspect, provided herein are vectors encoding the proteins (e.g., the first and second component proteins) described herein and cells for expressing the same.

According to still another aspect, provided herein are conjugation methods, the methods comprising: (a) providing a first component protein comprising a protein of interest in series with a sortase recognition sequence and a first binding pair partner; (b) providing a second component protein comprising a second binding pair partner in series with a sortase and a second component affinity tag having a selective affinity for a second component affinity tag resin, wherein the first binding pair partner and the second binding pair partner comprise two protein moieties that form a first heterodimer; (c) contacting the first binding pair partner with the second binding pair partner to form a heterodimer of the first component protein and the second component protein; and (d) adding calcium and glycine or a peptide/protein with an N-terminal glycine, under conditions where the sortase catalyzes release of the protein of interest and conjugation of it to the glycine, or a peptide/protein with an N-terminal glycine. In some embodiments, the second binding pair partner is N-terminal to the sortase and the sortase is N-terminal to the second component affinity tag. In some embodiments, the sortase is N-terminal to the second binding pair partner and the second binding pair partner is N-terminal to the second component affinity tag. In some embodiments, the following steps are performed sequentially: contacting the first binding pair partner with the second component binding pair partner to form a heterodimer; adding calcium and glycine, or a peptide/protein with an N-terminal glycine, under conditions in which the sortase catalyzes release of the protein of interest and conjugation of it to the glycine, or peptide/protein with an N-terminal glycine.

According to yet another aspect, provided herein are methods for purifying a protein of interest, the methods comprising: (a) providing a first component protein comprising the protein of interest in series with a sortase recognition sequence and a first binding pair partner; (b) providing a second component protein comprising a second binding pair partner in series with a sortase and a second component affinity tag having a selective affinity for a second component affinity tag resin, wherein the first binding pair partner and the second binding pair partner comprise two protein moieties that form a first heterodimer; (c) contacting the first binding pair partner with the second binding pair partner to form a heterodimer of the first component protein and the second component protein; (d) adding calcium and glycine or a peptide/protein with an N-terminal glycine, under conditions where the sortase catalyzes release of the protein of interest and conjugation of it to the glycine, or peptide/protein with an N-terminal glycine to form a conjugated protein; and (e) separating the conjugated protein. In some embodiments, the second binding pair partner is N-terminal to the sortase and the sortase is N-terminal to the second component affinity tag. In some embodiments, the sortase is N-terminal to the second binding pair partner and the second binding pair partner is N-terminal to the second component affinity tag. In some embodiments, the protein of interest is N-terminal to the sortase recognition sequence and the sortase recognition sequence is N-terminal to the first binding pair partner. In some embodiments, the first binding pair partner is N-terminal to the sortase recognition sequence and the sortase recognition sequence is N-terminal to the protein of interest. In some embodiments, the following steps are performed sequentially: contacting the first binding pair partner with the second component binding pair partner to for the first heterodimer; adding calcium and glycine, or a peptide/protein with an N-terminal glycine, under conditions in which the sortase catalyzes release of the protein of interest.

Other features and advantages of this invention will become apparent from the following detailed description examples and figures. It should be understood, however, that the detailed description and the specific examples while indicating preferred embodiments are given by way of illustration only, since various changes and modifications within the spirit and scope of the invention will become apparent to those skilled in the art from this detailed description.

BRIEF DESCRIPTION OF THE DRAWINGS

(FIG. 2A) A biomolecule of interest is expressed in frame with a sortase recognition motif (e.g., LPXTG) and one member of a binding pair (Binding Partner A). In parallel, a sortase enzyme is expressed in frame with a second member of a binding pair (Binding Partner B) and an affinity tag. The sortase construct can be bound to an affinity column or beads. The biomolecule is captured by the sortase construct via interaction of the binding pairs. The biomolecule is subsequently released from the affinity column upon ligation to any peptide/protein with an N-terminal glycine. If desired, the peptide/protein can be labeled with a chemical or biological moiety (e.g., imaging agent, drug, click chemistry group, hapten, oligonucleotide, etc.), indicated by the green star. (FIG. 2B) Proximity-based sortase ligation can also be performed if sortase is expressed between the second member of a binding pair and the affinity tag.

FIGS. 14A and 14B. PBSL vs. Traditional Sortase vs. Sortase Tag Expressed Protein Ligation (STEPL). (FIG. 14A) SDS-PAGE showing scFv constructs before and after sortase-mediated ligation to the fluorescent peptide GGGSK-TMR, using the PBSL approach (lanes 1 and 2), the traditional sortase approach (lanes 3 and 4-9), and STEPL (lane 10). The traditional sortase reaction was carried out using a sortase:scFv molar ratio ranging from 1:1 to 100:1. (FIG. 14B) Fluorescent image of the SDS-PAGE gel. Ligation of the scFv to the peptide GGGSK-TMR is easily detectable via TMR fluorescence. Even with the enormous excess of sortase used in the traditional reaction, only 50-60% of the scFv was fluorescently labeled (i.e. scFv-TMR). In contrast, with PBSL, the efficiency of ligation was ~100%, with no noticeable scFv still linked to the SpyCatcher-Sortase-HisTag construct. With STEPL, the direct fusion of the scFv to sortase interfered with normal protein expression and/or folding. As a result, no labeled protein, scFv-TMR, was detectable. (The scFv-TMR produced by the traditional sortase reaction runs slightly higher than the same product produced via PBSL due to the presence of an additional GGGS linker, prior to LPETG, in the expression plasmid.)

(FIG. 16A) LgBiT, the large half of split NanoLuc luciferase, and (FIG. 16B) an anti-CD3 scFv were purified with either His-tag and $Co^{2+}$ resin or PBSL and SpyCatcher-SrtA-His$_{12}$ resin. The resins were washed with PBS+0, 20, or 40 mM imidazole prior to elution. For both proteins, not only does PBSL result in significantly greater purity when washing with just PBS, but PBSL is also much more resistant to decreases in yield when using more stringent washes containing imidazole.

DETAILED DESCRIPTION OF THE INVENTION

Figure 1:
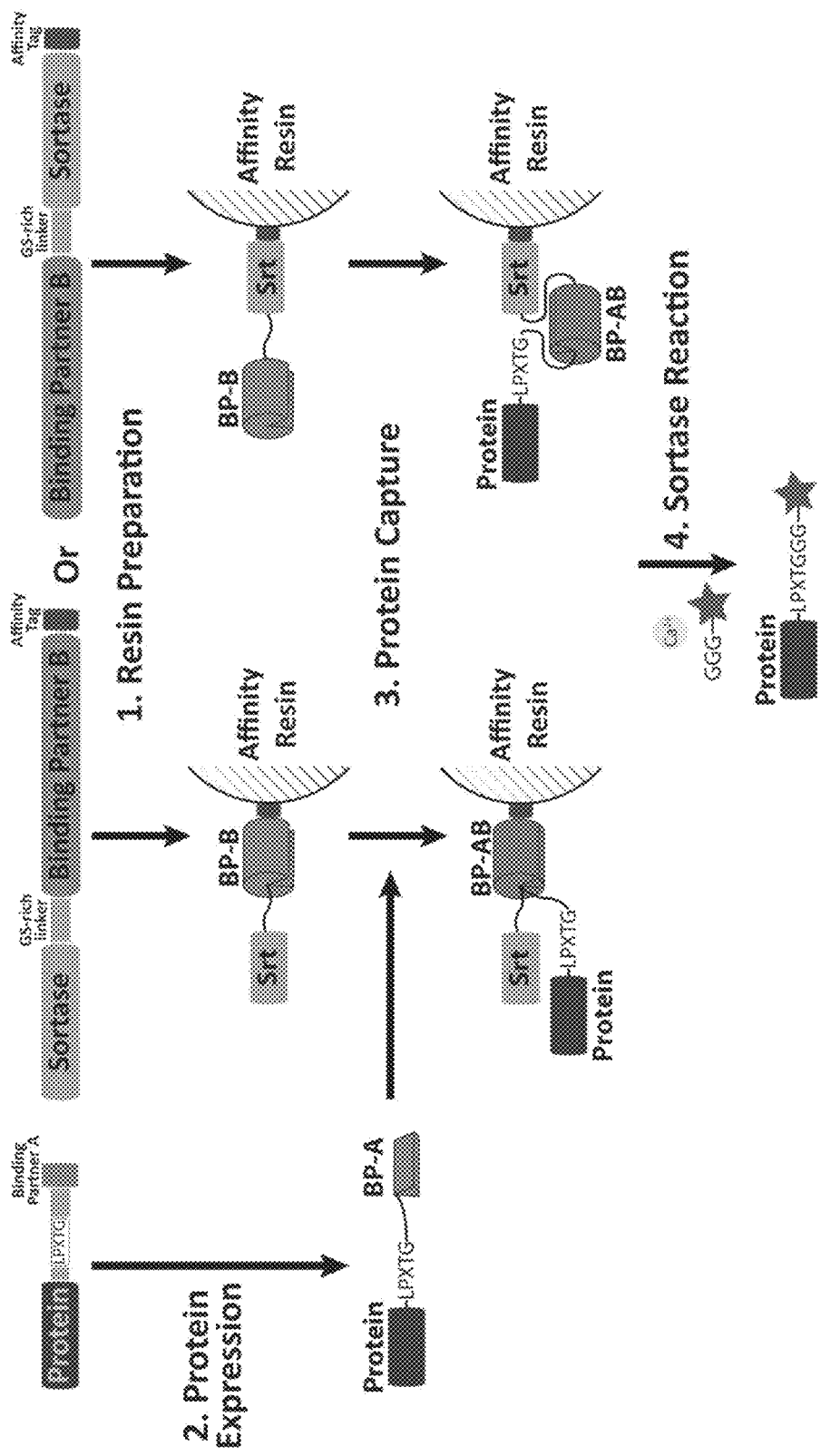
FIG. 1. Proximity-Based Sortase Ligation Schematic. To generate the capture fusion protein, sortase (Srt) is placed in frame either N-terminal (A) or C-terminal (B) to binding partner B (BP-B), with a linker (e.g. a GS-rich linker, such as $(GGS)_2$) between the two proteins. This fusion protein is then (1.) expressed and isolated on an affinity resin. (2.) The protein of interest is cloned in series and in frame with the sortase recognition motif (e.g., LPXTG), and binding partner A (BP-A). (3.) The protein of interest is expressed and then captured onto the affinity resin through the interaction between binding partners A and B. (4.) Adding both calcium and a peptide with an N-terminal glycine or polyglycine (e.g., GGG) allows sortase simultaneously to cleave the protein from the affinity resin and to ligate the peptide onto the protein, which can then be isolated.

The invention relates to a proximity-based sortase-mediated protein purification and ligation. Specifically, the invention relates to nucleic acid and protein conjugates and proximity-based techniques that link protein expression/purification with conjugation to therapeutic agents, imaging agents, or linkers.

Previously, a number of methods had been developed to link a ligand or protein of interest to its cargo, based on maleimide, N-hydroxysuccinimide, carbodiimide, and click chemistries. However, many of these suffer from poor reaction efficiencies and all of them label at random residues on the ligand. A few techniques have been developed to address these problems, including expressed protein ligation (EPL), but they have shortcomings of their own.

Examples for obtaining antibody conjugates, including bispecific antibody conjugates, can be found in WO2016/183387, filed May 12, 2016, which is incorporated by reference herein in its entirety. This approach, for example, comprises an antibody-binding domain (AbBD) operably linked to a photoreactive amino acid, and in turn, being operably linked to cargo or an antibody or a fragment thereof. Where the AbBD is fused in frame with a peptide tag or a protein that is a member of a binding pair and a second construct is provided comprising a second antibody or a fragment thereof and a peptide tag or a protein that is the corresponding member of the binding pair, the site-specific linkage of the binding pair moieties on the two constructs can be used to form a bispecific antibody. However, it would be desirable to be able to apply improved directed conjugation methods to antibodies and fragments thereof, such as antigen-binding domains or tags.

Combining the concepts behind expressed protein ligation (EPL) with a sortase enzyme, a single-step/single-construct sortase-tag expressed protein ligation (STEPL) technique had also been developed linking protein expression/purification with conjugation to therapeutic agents, imaging agents, or linkers that can be used for subsequent conjugations (e.g. biotin, click chemistry groups such as azides or alkynes). Specifically, the coding sequence for the desired protein (e.g. a targeting ligand) was cloned in series with the coding sequence for a sortase recognition sequence (e.g. LPXTG) followed by Sortase A and an affinity tag (e.g. Histidine Tag), as described in U.S. Pat. No. 9,631,218, issued Apr. 25, 2017, and which is incorporated by reference herein in its entirety.

Unexpectedly and surprisingly, however, it has been found that a two-construct, proximity-based sortase-mediated protein purification and ligation method can yield improved results over the single-step/single-construct method in which sortase is fused directly to the expressed protein. Although this latter method works well with shorter proteins, in some instances, the sortase interferes with the proper folding of larger or more complex proteins (e.g., scFv proteins), thereby disrupting the secondary structure of the protein of interest, and additionally, this approach may be incompatible with protein expression systems where calcium is present (e.g., yeast and mammalian systems).

The present methods utilize the affinity of a pair of binding partners to achieve protein capture of a protein of interest, followed by subsequent cleavage of the protein and ligation of the sortase recognition peptide onto the protein. By commencing with the sortase and the protein of interest on separate fusion protein constructs, the secondary structure folding of the protein of interest can be achieved prior to interaction with the sortase on the capture fusion protein construct. In addition, in expression systems in which calcium is present, the two constructs can be maintained separately until the time when the interaction is set to take place.

Accordingly, the present invention provides conjugate protein compositions comprising a first component protein and a second component protein, wherein: (i) the first component protein comprises a protein of interest in series with a sortase recognition sequence and a first binding pair partner; and (ii) the second component protein comprises a second binding pair partner in series with a sortase and a second component affinity tag having a selective affinity for a second component affinity tag resin, wherein the first binding pair partner and the second binding pair partner comprise two protein moieties that form a first heterodimer. In some embodiments, the second binding pair partner is N-terminal to the sortase and the sortase is N-terminal to the second component affinity tag. In some embodiments, the sortase is N-terminal to the second binding pair partner and the second binding pair partner is N-terminal to the second component affinity tag. In some embodiments, the affinity tag is N-terminal to the second binding pair partner and the second binding pair partner is N-terminal to the sortase. In some embodiments, the affinity tag is N-terminal to the sortase and the sortase is N-terminal to the second binding pair partner.

In some embodiments, the first component protein further comprises a first component affinity tag. In some embodiments, the first component affinity tag has a selective affinity for the second component affinity tag resin. In other embodiments, the first component affinity tag is distinct from the second component affinity tag and has a selective affinity for a first component affinity tag resin. In some embodiments, said sortase recognition sequence of said first component protein is C-terminal to said protein of interest and N-terminal to said first binding pair partner. In some embodiments, said sortase recognition sequence of said first component protein is N-terminal to said protein of interest and C-terminal to said first binding pair partner.

In some embodiments, said first component protein comprises an antibody of interest or a fragment thereof in series with at least one sortase recognition construct comprising the sortase recognition sequence and the first binding pair partner. In some embodiments, the sortase recognition construct is C-terminal to at least one light chain or heavy chain of the antibody of interest or the fragment thereof and wherein said binding pair partner is C-terminal to said sortase recognition sequence. In some embodiments, said sortase recognition construct is C-terminal to at least one light chain of said antibody of interest. In some embodiments, said sortase recognition construct is C-terminal to at least one heavy chain of said antibody of interest.

In some embodiments, the composition comprises a first component protein, a second component protein, and a third component protein. In some embodiments, (i) the first component protein comprises an antibody of interest or fragment thereof with (A) a first antibody sortase recognition construct C-terminal to at least one heavy chain of the antibody or fragment thereof and comprising a first antibody sortase recognition sequence and a first antibody binding pair partner; and (B) a second antibody sortase recognition construct C-terminal to at least one light chain of said antibody or fragment thereof and comprising a second antibody sortase recognition sequence and a second antibody binding pair partner; (ii) the second component protein comprises a second component binding pair partner in series with a second component sortase and a second component affinity tag having a selective affinity for a second component affinity tag resin, wherein the first antibody binding pair partner and the second component binding pair partner form the first heterodimer; (iii) a third component protein comprising a third component binding pair partner in series with a third component sortase and a third component affinity tag, wherein said second antibody binding pair partner and said third component binding pair partner comprise two protein moieties that form a second heterodimer. In some embodiments, the second component binding pair partner is N-terminal to the second component sortase, and the second component sortase is N-terminal to the second component affinity tag. In some embodiments, the second component sortase is N-terminal to the second component binding pair partner and the second component binding pair partner is N-terminal to the second component affinity tag. In some embodiments, said third component binding pair partner is N-terminal to said third component sortase and said third component sortase is N-terminal to said third component affinity tag. In some embodiments, said third component sortase is N-terminal to the third component binding pair partner and the third component binding pair partner is N-terminal to the third component affinity tag. In some embodiments, the third component affinity tag has a selective affinity for the second component affinity tag resin. In other embodiments, the third component affinity tag is distinct from the second component affinity tag and has a selective affinity for a third component affinity tag resin.

In some embodiments, each binding pair partner comprises a peptide tag or a protein that is a member of a binding pair. In some embodiments, the binding pair consists of a split adhesin domain. In some embodiments, one of the binding pair partners comprises SpyCatcher and the other binding pair partner comprises SpyTag. In some embodiments, one of the binding pair partners comprises Snoop-Catcher and the other binding pair partner comprises SnoopTag. In some embodiments, one of the binding pair partners comprises one half of a split intein and the other binding pair partner comprises the other half of the split intein.

In some embodiments, a binding pair comprises two proteins that form a heterodimer. In some embodiments, one of the binding pair partners comprises a first dimerization domain and the other binding pair partners comprises a second dimerization domain, wherein the two dimerization domains form a heterodimer. In one embodiment, one of the binding pair partners comprises c-Jun and the other binding pair partner comprises c-Fos. In another embodiment, a binding pair comprises a leucine zipper. In still another embodiment, a binding pair comprises peptide Velcro, i.e., two peptides that are predominantly unfolded in isolation but which, when mixed, associate preferentially to form a stable, parallel, coiled-coil heterodimer, such as a leucine zipper (See O'Shea et al. (1993) Curr. Biol. 3:658-667). In other embodiments, one of the binding pair partners comprises SpyCatcher and the other binding pair partner comprises SpyTag. In another embodiment, one of the binding partners comprises a portion of a split adhesin domain, while the other binding pair partner comprises the remaining portion. In other embodiments, one of the binding pair partners comprises SnoopCatcher and the other binding pair partner comprises SnoopTag. In some embodiments, one of the binding pair partners comprises S-protein and the other binding pair partner comprises S-tag. In some embodiments, one of the binding pair partners comprises Strep-tag or Strep-tag II and the other binding pair partner comprises Streptavidin or Streptactin. In some embodiments, one of the binding pair partners comprises calmodulin-binding peptide and the other binding pair partner comprises Calmodulin.

In some embodiments, the protein of interest is a recombinant protein, a fusion protein, and enzyme, and/or a bispecific antibody.

In one embodiment, said conjugate protein composition comprises a dock-and-lock system in which the binding pair partners fuse and further comprise a third peptide or protein covalently linking one binding pair partner to the other. In some embodiments, the binding pair partners are chemically linked, in some cases, further comprising a chemical moiety to link one binding pair partner to the other.

In some embodiments said conjugate protein composition is specifically attached in a suitable orientation to a surface, polypeptide, a particle, or a drug. In some embodiments, said additional polypeptide is a drug or a toxin.

In some embodiments, said sortase is selected from the group consisting of sortase A (SrtA), sortase B (SrtB), sortase C (SrtC), sortase D (SrtD), sortase E (SrtE) and sortase F (SrtF). In one embodiment, said sortase is from a Gram-positive bacteria. In one embodiment, said sortase is sortase A from *Staphylococcus aureus* or sortase A from *Streptococcus pyogenes*. In some embodiments, the sortase can be engineered or modified to possess unique substrate specificity. In some embodiments, the sortase can be engineered or modified to be exhibit improved or increased catalytic activity. In some embodiments, the sortase can be engineered or modified to be insensitive to calcium.

In some embodiments, said sortase recognition sequence is selected from the group consisting of LPXTG (SEQ ID NO: 1), LPKTG (SEQ ID NO: 2), LPATG (SEQ ID NO: 3), LPNTG (SEQ ID NO: 4), LPETG (SEQ ID NO: 5), LPXAG (SEQ ID NO: 6), LPNAG (SEQ ID NO: 7), LPXTA (SEQ ID NO: 8), LPNTA (SEQ ID NO: 9), LGXTG (SEQ ID NO: 10), LGATG (SEQ ID NO: 11), IPXTG (SEQ ID NO: 12), IPNTG (SEQ ID NO: 13), IPETG (SEQ ID NO: 14), NPQTN (SEQ ID NO: 15), LAXTG (SEQ ID NO: 16), LPXSG (SEQ ID NO: 17), LSETG (SEQ ID NO: 18), LPXCG (SEQ ID NO: 19), LPXAG (SEQ ID NO: 20), and XPETG (SEQ ID NO: 21).

In some embodiments, an affinity tag is selected from the group consisting of a histidine tag (His tag), a chitin-binding domain, a calmodulin tag, a polyglutamate tag, a maltose binding protein, glutathione-S-transferase, an S-tag, a peptide that binds avidin/streptavidin/neutravidin (e.g. SBP-tag, Strep-tag, etc.), green fluorescent protein-tag, thioredoxin tag, Nus-tag, Fc-tag, Halo-tag. In some embodiments the affinity tag is selected from the group consisting of FLAG-tag, V5-tag, VSV-tag, Xpress tag, E-tag, Myc-tag, HA-tag, Softag, and NE-tag. On some embodiments, a protein tag may allow for specific enzymatic modification into an affinity tag, such as biotinylation by biotin ligase or BirA (e.g. AviTag, BCCP (biotin carboxyl carrier protein)). In some embodiments, the affinity tag is selected from covalent peptide tags such as isopeptag, SpyTag, SnoopTag. Some embodiments, further comprising a first or second affinity tag resin to which said first or second affinity tag, respectively, selectively binds. In some embodiments, the resin is an immobilized metal affinity chromatography (IMAC) resin. In some embodiments, the resin is selected from the group consisting of nickel resin, cobalt resin, TALON® resin, chitin resin, and streptavidin resin. In some embodiments, said affinity tag and said resin is selected from the group of combinations consisting of a histidine tag (His tag) in combination with a nickel or cobalt resin, a chitin-binding domain affinity tag in combination with a chitin resin, and biotinylated biotin acceptor peptide affinity tag in combination with a streptavidin resin. In one embodiment, said affinity tag is a histidine tag and said resin is a nickel resin or a cobalt resin. In some embodiments, the resin is bound to an antibody capable of binding the affinity tag. In some embodiments, the resin is bound to a protein capable of binding an affinity tag, such as avidin/streptavidin/neutravidin, streptactin, calmodulin, Protein A or G, or S-protein. In some embodiments, the resin is HaloLink resin. In some embodiments, the resin is amylose agarose. In some embodiments glutathione is bound to the resin.

In some embodiments, said N-terminal glycine comprises a single glycine. In some embodiments, said N-terminal glycine comprises a plurality of N-terminal glycines or an N-terminal polyglycine, such as an N-terminal triglycine. In some embodiments, the glycine, polyglycine, or peptide/protein (including enzymes) with an N-terminal glycine further comprises a functional group or label. In some embodiments, the glycine, polyglycine, or peptide/protein with an N-terminal glycine is fused or linked to a protein, an enzyme, a drug molecule, an imaging agent, a metal chelate, a polyethylene glycol, a click chemistry group, an alkyne, an azide, a hapten, a biotin, a photocrosslinker, an oligonucleotide, a small molecule, azodibenzocyclooctyne (ADIBO), DIG, DBCO, TCO, tetrazine, a nanoparticle, or an antibody binding domain (AbBD).

In some embodiments, the peptide/protein with an N-terminal glycine is fused or linked to the protein of interest to permit circularization with the protein of interest. In some embodiments, the N-terminal glycine is fused or linked to the protein of interest, thereby allowing for circularization and purification of the protein in a single step. In one embodiment, said click chemistry group comprises GGG-K (azide) or an azodibenzocyclooctyne (ADIBO)-functionalized superparamagnetic iron oxide (SPIO) nanoparticle. In one embodiment, said imaging agent comprises a fluorophore or a ligand, capable of chelating a metal or radioisotope. In one embodiment, said drug molecule comprises an antibiotic. In some embodiments, said protein of interest is an antibody binding domain (AbBD) that comprises Protein A, Protein G, Protein L, CD4, or a subdomain thereof. In some embodiments, said subdomain is an engineered subdomain, such as to include a non-natural amino acid, a photoreactive group, or a crosslinker. In some embodiments, said antibody-binding domain (AbBD) is operably linked to a photoreactive amino acid and is operably linked to an antibody or a fragment thereof. In one embodiment, said antibody-binding domain (AbBD) is operably linked to an immunoglobulin Fc region, such as an IgG. In one embodiment, said photoreactive amino acid is a UV-active non-natural amino acid or benzoylphenylalaine (BPA). In some embodiments, said antibody-binding domain is a domain of Protein G, Protein A, Protein L, or CD4 or is hyperthermophilic variant of the B1 domain of protein G (HTB1). In some embodiments, BPA is incorporated into a protein Z comprising SEQ ID NO: 22, such as to replace F5, F13, L17, N23, Q32, or K35 of SEQ ID NO: 22. In some embodiments, BPA is incorporated into a protein G domain comprising SEQ ID NO: 23, such as to replace A24 or K28 of SEQ ID NO: 23.

Generally, said conjugate protein composition may be specifically attached in the proper orientation to a surface or a particle.

In some embodiments, the first component protein, the second component protein, and/or the third component protein further comprise at least one linker. In some embodiments, said protein of interest, or said antibody or fragment thereof, is operably linked to said sortase recognition sequence via said linker; and/or said sortase recognition sequence is operably linked to said first binding pair partner via said linker. In one embodiment, said sortase is operably linked to said second binding pair partner via said linker. In some embodiments, the second affinity tag is operably linked to said second binding pair partner or to said sortase via said linker. In some embodiments, the first affinity tag is operably linked to said first binding pair partner via said linker. In one embodiment, said linkers comprises a glycine-serine (GS)-rich linker. In one embodiment, a glycine-serine (GS)-rich linker is a (GGS)n linker, where n is an integer indicating the number of (GGS) repeats, such as where n is an integer greater or equal to 2 and or where n is an integer between 2 and 5, both inclusive. In some embodiments, the linker is a (GGS)5 linker.

In some embodiments, said antibody or antibody fragment comprises an immunoglobulin G (IgG), an immunoglobulin M (IgM), an immunoglobulin D (IgD), an immunoglobulin E (IgE), or an immunoglobulin A (IgA). In some embodiments, said IgG is selected from the group consisting of IgG1, IgG2, IgG3, and IgG4. In some embodiments, said antibody fragment comprises an Fc domain or an Fab domain. In some embodiments, said antibody fragment comprises an Fv, Fab, Fab', or (Fab')2 domain. In some embodiments, said antibody fragment comprises a variable region of said antibody or a single-chain antibody, or an scFv. In some embodiments, said antibody or fragment thereof comprises an scFv-Fc or other fusion antibody.

In another aspect, the present invention provides vectors encoding a first component protein, a second component protein, or a third component protein described herein. In some embodiments, said vector is an expression vector. In some embodiments, said vector comprises a coding sequence for a protein of interest in frame with a coding sequence for a sortase recognition sequence and a coding sequence for a first binding pair partner. In some embodiments, said coding sequence for said protein of interest is 5' to said coding sequence for said sortase recognition sequence, and said coding sequence for said sortase recognition sequence is 5' to said coding sequence for said binding pair partner. In some embodiments, the vector may further comprise a coding sequence for said binding pair partner and said coding sequence for said binding pair partner is 5' to said sortase recognition sequence, and said coding sequence for said sortase recognition sequence is 5' to said protein of interest. In some embodiments, the vector may further comprise a coding sequence for an affinity tag, wherein said coding sequence for said protein of interest is 5' to said coding sequence for said sortase recognition sequence, and said coding sequence for said sortase recognition sequence is 5' to said coding sequence for said binding pair partner and said coding sequence for said binding pair partner is 5' to said affinity tag. In some embodiments, the vector may further comprise a coding sequence for an affinity tag, wherein said coding sequence for said affinity tag is 5' to said coding sequence for said binding pair partner and said coding sequence for said binding pair partner is 5' to said sortase recognition sequence, and said coding sequence for said sortase recognition sequence is 5' to said protein of interest. In some embodiments, said vector comprises a coding sequence for a second binding pair partner in frame with a coding sequence for a sortase, wherein: said coding sequence for said second binding pair partner is 5' to said coding sequence for said sortase; or said coding sequence for said second binding pair partner is 3' to said coding sequence for said sortase. In some embodiments, the vector may further comprise a coding sequence for an affinity tag, wherein said coding sequence for said second binding pair partner is 5' to said coding sequence for said sortase and said coding sequence for said sortase is 5' to said coding sequence for said affinity tag; or said coding sequence for said sortase is 5' to said coding sequence for said second binding pair partner and said coding sequence for said second binding pair partner is 5' to said affinity tag. In some embodiments, said coding sequence for said affinity tag is 5' to said second binding pair partner and said second binding pair partner is 5' to said coding sequence for said sortase; or said coding sequence for said affinity tag is 5' to said coding sequence for said sortase and said coding sequence for said sortast is 5' to said coding sequence for said second binding pair partner. In some embodiments, said coding sequence for said sortase recognition sequence of said vector for said first component protein is 3' to said coding sequence for said protein of interest and 5' to said coding sequence for said first binding pair partner. In some embodiments, a coding sequence encodes at least one linker. In some embodiments, said coding sequence for said protein of interest is in frame with a coding sequence for said linker, which is in frame with said coding sequence for said sortase recognition sequence via a linker; or said coding sequence for said sortase recognition sequence is in frame with a coding sequence for said linker, which is in frame with said coding sequence for said first binding pair partner. In some embodiments, said coding sequence for said sortase is in frame with a coding sequence for said linker, which is in frame with said coding sequence for said second binding pair partner. In some embodiments, said coding sequence for said affinity tag is in frame with a coding sequence for said linker, which is in frame with said coding sequence for said second binding pair partner or with said coding sequence for said sortase. In some embodiments, said linkers comprise a glycine-serine (GS)-rich linker. In some embodiments, a glycine-serine (GS)-rich linker comprises a (GGS)n linker, where n is an integer indicating the number of (GGS) repeats. In some embodiments, n is an integer greater or equal to 2; n is an integer greater or equal to 3; or n is an integer between 2 and 5, both inclusive. In one embodiment, at least one of said linkers is a (GGS)5 linker.

In still another aspect, the present invention provides a cell for recombinantly expressing said first component protein and/or said second component protein, wherein said cell is a bacterial cell, a yeast cell, an insect cell, or a mammalian cell. In some embodiments, the cell is transformed with an expression vector described herein.

In yet another aspect, the present invention provides conjugation methods, the methods comprising: (a) providing a first component protein comprising a protein of interest in series with a sortase recognition sequence and a first binding pair partner; (b) providing a second component protein comprising a second binding pair partner in series with a sortase and a second component affinity tag having a selective affinity for a second component affinity tag resin, wherein the first binding pair partner and the second binding pair partner comprise two protein moieties that form a first heterodimer; (c) contacting the first binding pair partner with the second binding pair partner to form a heterodimer of the first component protein and the second component protein; and (d) adding calcium and glycine or a peptide/protein with an N-terminal glycine, under conditions where the sortase catalyzes release of the protein of interest and conjugation of it to the glycine, or peptide/protein with an N-terminal glycine. In some embodiments, the second binding pair partner is N-terminal to the sortase and the sortase is N-terminal to the second component affinity tag. In some embodiments, the sortase is N-terminal to the second binding pair partner and the second binding pair partner is N-terminal to the second component affinity tag. In some embodiments, the first component protein further comprises a first component affinity tag. In some embodiments, the first component affinity tag has a selective affinity for the second component affinity tag resin. In other embodiments, the first component affinity tag is distinct from the second component affinity tag and has a selective affinity for a first component affinity tag resin.

In a preferred embodiment, the sortase recognition sequence includes the motif LPXTG (Leu-Pro-any-Thr-Gly—SEQ ID NO: 1) (wherein the occurrence of X represents independently any amino acid residue). Sortase cleaves between the Gly and Thr of the LPXTG motif. Other variant sortase recognition sequences, known in the art, can also be used. Variant sortase recognition sequences are known and described in PCT international patent application WO 2013/003555, U.S. Pat. No. 7,238,489 and US Publ. 2014/0030697, which are fully incorporated by reference herein in their entirety. Examples of other sortase recognition sequences, include, but are not limited to LPKTG (SEQ ID NO: 2), LPATG (SEQ ID NO: 3), LPNTG (SEQ ID NO: 4), LPETG (SEQ ID NO: 5), LPXAG (SEQ ID NO: 6), LPNAG (SEQ ID NO: 7), LPXTA (SEQ ID NO: 8), LPNTA (SEQ ID NO: 9), LGXTG (SEQ ID NO: 10), LGATG (SEQ ID NO: 11), IPXTG (SEQ ID NO: 12), IPNTG (SEQ ID NO: 13), IPETG (SEQ ID NO: 14). Additional suitable sortase recognition motifs, such as NPQTN (SEQ ID NO: 15), will be apparent to those of skill in the art, and the invention is not limited in this respect. It will be appreciated that the terms "recognition motif" and "recognition sequence", with respect to sequences recognized by a transamidase or sortase, are used interchangeably.

The coding sequence of any suitable sortase enzyme can be used. Sortases are well known in the art. Sortases are also referred to as transamidases, and typically exhibit both a protease and a transpeptidation activity. Sortases have been classified into 6 classes, designated A, B, C, and D; designated sortase A (SrtA), sortase B (SrtB), sortase C (SrtC), sortase D (SrtD), sortase E (SrtE), and sortase F (SrtF), respectively, based on sequence alignment and phylogenetic analysis of 73 sortases from Gram-positive bacterial genomes. In a preferred embodiment, sortase is sortase A. In some embodiments, the sortase A is from *Staphylococcus aureus* or from *Streptococcus pyogenes*.

The coding sequences of sortases, including sortase A, are well known in the art and publicly available in biological sequence databases and U.S. Pat. No. 7,238,489, which are incorporated by reference herein in their entirety.

In some embodiments, the coding sequence of the protein of interest is operably linked to the coding sequence of sortase recognition sequence via a linker, and the coding sequence of the sortase recognition sequence is operably linked to the coding sequence of the binding pair partner A via a linker. In some embodiments, the coding sequence for the sortase is operably linked to the coding sequence of the binding pair partner B, and the affinity tag is linked to the coding sequence for the sortase or to the coding sequence of the binding pair partner B via a linker.

Any suitable linker known to one of skilled in the art can be used. In one embodiment, the linker is a glycine-serine (GS)-rich linker, particularly a flexible GS-rich linker. In one embodiment, the flexible GS-rich linker is a (GGS)n linker, where n is an integer indicating the number of (GGS) repeats. In one embodiment, the linker is a (GGS)5 linker. The (GGS)5 linker facilitates the sortase domain to have the conformational freedom to recognize the sortase recognition motif. Alternatively, the linker is a (GGS)2 or (GGS)3 linker.

Notably, five GGS repeats may be chosen for the fusion construct because the crystal structure reports a length of 26.2 Å between the N-terminus of the sortase domain and its active site, corresponding to the length of approximately 3 GGS repeats (8.8 Å each). Thus, a (GGS)5 linker may be expected to provide sufficient spatial flexibility for the sortase domain to recognize and bind the LPXTG motif.

Any suitable affinity tag known to one skilled in the art can be used. In one embodiment, the affinity tag is a histidine tag (His tag).

Also provided herein are vectors comprising a conjugate described herein. Any suitable expression vector known to one of skilled in the art can be used. The expression protocol can be optimized based on the chosen vector.

Following protein expression and capture through interaction between the binding pair partners, the protein of interest can be released from the sortase and affinity tag by administration of calcium and glycine. Peptides or proteins with one or more N-terminal glycines are possible. During this process glycine, the glycine-peptide/protein is specifically ligated to the C-terminus of the protein of interest. This method therefore allows for the facile conjugation of a peptide/protein specifically to the C-terminus of the expressed protein.

For example, the use of the peptide GGG-K(FAM) allows for the attachment of the fluorescent dye fluorescein (FAM) to the C-terminus of the expressed protein. This dye can be ligated, for example, in a 1:1 stoichiometric ratio with the expressed protein. Therefore, it is site-specific and can be used for quantitative analysis of fluorescence.

Any suitable molecule that can be attached to a peptide with an N-terminal glycine can be specifically attached to the C-terminus of the expressed protein (e.g. dyes, drugs, haptens such as biotin, polymers such as PEG, etc.).

In one example, a peptide is ligated with an azide group (e.g. GGG-K(azide)), which is subsequently used for click conjugations reactions. For example, after ligation the click chemistry could be used to attach the expressed protein onto surfaces (e.g., for ELISA assays and nanoparticle surfaces). Importantly, the conjugation in this case is site-specific, so all of the proteins are oriented in the same direction on the surface. Moreover, there is only a single attachment point—the azide—which was ligated to the C-terminus of the express protein in a 1:1 ratio. One could also click drug molecules or other agents to the expressed protein, in a site-specific manner.

Following protein expression and capture through interaction between the binding pair partners, the protein of interest can be released from the sortase and affinity tag by administration of calcium and glycine. Peptides or proteins with one or more N-terminal glycines are preferred. If the sortase recognition sequence is N-terminal to the protein of interest, the released protein will possess a glycine that is N-terminal to the protein of interest.

A general vector for bacterial expression has been produced. The expression protocol has been optimized. The cleavage reaction has been studied quantitatively and modeled to allow for optimization based on the user's needs. The system has been successfully used to express and conjugate a number of proteins including eGFP (EGFP), affibodies, IgG, antibody fragments (e.g. scFv's), natural extracellular matrix binding domains, and cytokines. The conjugated peptides have included visible and near-IR fluorophores, drugs (e.g. MMAE), haptens (e.g. biotin), polymers (e.g. PEG), and bio-orthogonal reactive groups (e.g., azide).

In addition to calcium for cleavage, any suitable agent known to one skilled in the art can be used. For example, one can reengineer the sortase domain to be calcium independent or to depend on a transition metal or small molecule rather than calcium for cleavage.

The purification or conjugation systems described here have a number of advantages over expressed protein ligation and other sortase-mediated purification or conjugation systems. First, the techniques here link the final purification step to conjugation, ensuring that recovered protein is conjugated. This eliminates the difficult separation of conjugated and unconjugated peptides or proteins. Second, placing the protein of interest N-terminal to the LPXTG motif allows the first, glycine-free step in the sortase mechanism to occur without releasing any protein. Because the sortase retains the protein during this step, the crippling W194A mutation (which is required in other sortase purification techniques) is unnecessary and the more efficient wild-type Sa-SrtA can be used. The system also avoids chemistry based on functional groups generally found in biology, such as amines and thiols, greatly expanding the classes of proteins that can be expressed.

The methods and compositions described herein can be used in recombinant protein expression and other applications. These applications include, for example, efficient and economic production of targeting ligands that have been conjugated to imaging and therapeutic agents. Another use is PEGylation of a biologic drug to help improve circulation time. Additionally, one use is the ligation of unique chemical moieties (e.g., click groups such as azides or alkynes, biotin, DIG, etc), at the C-terminus of the expressed protein that allows for facile and site-specific conjugation to surfaces, drugs, imaging agents, nanoparticles, etc. Applications also include protein purification. Proteins can be produced with extremely high levels of purity because the sortase reaction triggers the release of only the protein of interest. Other proteins that are non-specifically bound to the affinity column are not released upon the addition of glycine and/or calcium. Moreover, affinity tags with superior affinity (e.g. His12 vs. His6) can used, since protein purification does not requires stripping the protein of interest from the affinity column. The protein of interest is released via the sortase reaction. This is important because it allows the protein of interest to be subjected to more stringent washing conditions when bound to the affinity column, prior to sortase-mediated release. This is not possible with other systems because when affinity tags are too tightly bound to the affinity column, the harsh conditions that are necessary to eventually release the protein of interest from the affinity column can be damaging to the protein of interest.

In addition, the techniques described here can be used to functionalize targeting ligands with chemical groups useful for molecular imaging. For example, a ligand can be used to chelate metals (e.g. Gd) or radioisotopes (e.g. Cu-64) for magnetic resonance, CT, or nuclear imaging. As another example, a near-IR fluorophore can be utilized to optically differentiate between cells expressing and lacking a proto-oncogene, such as Her2/neu. In one example, the NIR-dyed affibody would be used to quantify Her2/neu expression differences between different cells (e.g., T6-17 cells, NIH/3T3 cells, cancerous or non-cancerous cells from patient samples), which demonstrates its utility for in-cell Western techniques. Additionally, proximity-based sortase-mediated expressed protein ligation could be used to conjugate a bio-orthogonal reactive group (e.g., an azide) to the Her2/neu affibody of this example. For example, the azide ability to react to the presence of a strained alkyne on the surface of superparamagnetic iron oxide nanoparticles could be observed. Due to the site-specific nature of proximity-based sortase-mediated expressed protein ligation, the affibody can be linked in a specific orientation, which would increase the particle's efficacy in distinguishing between cells expressing and lacking Her2/neu. Proximity-based sortase-mediated expressed protein ligation can also be used to conjugate many other moieties to its target protein, such as biotin, poly(ethylene-glycol), antibiotics, metal chelates, and photocrosslinkers, all of which have been proven compatible with the sortase enzyme.

In one embodiment, the protocol is modified, optimized, modeled, and used to conjugate the Her2/neu and EGFR-targeting affibody to fluorophores for imaging and/or an azide for subsequent copper-free click chemistry reactions with azadibenzocyclooctyne (ADIBO)-functionalized superparamagnetic iron oxide nanoparticles, demonstrating the system's flexibility, efficacy, and utility.

Provided herein are protein or antibody conjugates (e.g., a bispecific antibody), drug and nanoparticle compositions and methods and compositions for generating them. Further provided herein are methods of using these compositions for imaging, diagnosing or treating a disease, such as cancer.

All types of antibodies are contemplated. In one embodiment, provided herein are methods to site-specifically label an antibody with a chemical or biological moiety. In one aspect, provided herein are methods to site-specifically attach an antibody onto a surface. In another aspect, provided herein are methods of producing a bispecific antibody. The inventors have developed facile methods for the efficient production of bispecific antibodies from full-length IgG, by ligating a second targeting ligand with an N-terminal glycine. More broadly, the inventors have developed facile methods for the efficient production of bispecific targeting ligands with the protein of interest being the first targeting ligand, which can be ligated to a second targeting ligand with an N-terminal glycine.

The term "Protein Z," as used herein, refers to the Z domain based on B domain of Staphylococcal aureus Protein A. The amino acid sequence of wild-type Protein Z is: VDNKFNKEQQNAFYEILHLPNLNEEQR-NAFIQSLKDDPSQSANLLAEAKKLNDAQAP KMRM (SEQ ID NO: 22). Photoreactive Protein Z includes those where an amino acid in protein Z has been replaced with benzoylphenylalanine (BPA), such as F13BPA and F5BPA (see underlined amino acids in bold in SEQ ID NO: 22). Examples of other BPA-containing mutants of Protein Z include, for example, but are not limited to, Q32BPA, K35BPA, N28BPA, N23BPA, and L17BPA. Examples of Protein Z variants or mutants include, F5I, such as F5I K35BPA. The Protein Z amino acid sequence may also include homologous, variant, and fragment sequences having Z domain function. In some embodiments, the Protein Z amino acid sequence may include an amino acid sequence which is 60, 65, 70, 75, 80, 85, 90, 95, or 99% identity to the sequence set forth in SEQ ID NO: 22.

The term "Protein G," as used herein, refers to a B1 domain based of Streptococcal Protein G. Preferably, the Protein G is a hypothermophilic variant of a B1 domain based of Streptococcal Protein G. The amino acid sequence of Protein G preferably is: MTFKLI-INGKTLKGEITIEAVDAAEAEKIFKQYANDYGIDGEW-TYDDATKTFTVTE (SEQ ID NO: 23). Nine Protein G variants were successfully designed and expressed, each having an Fc-facing amino acid substituted by BPA: V21, A24, K28, I29, K31, Q32, D40, E42, W42 (see underlined amino acids in bold in SEQ ID NO: 23). Two variants, A24BPA and K28BPA, allowed ~100% of all human IgG subtypes to be labeled. The Protein G amino acid sequence may also include homologous, variant, and fragment sequences having B1 domain function. In some embodiments, the Protein G amino acid sequence may include an amino acid sequence which is 60, 65, 70, 75, 80, 85, 90, 95, or 99% identity to the sequence set forth in SEQ ID NO: 23.

As used herein, the term "Fc domain" encompasses the constant region of an immunoglobulin molecule. The Fc region of an antibody interacts with a number of Fc receptors and ligands, imparting an array of important functional capabilities referred to as effector functions, as described herein. For IgG the Fc region comprises Ig domains CH2 and CH3. An important family of Fc receptors for the IgG isotype are the Fc gamma receptors (FcγRs). These receptors mediate communication between antibodies and the cellular arm of the immune system.

As used herein, the term "Fab domain" encompasses the region of an antibody that binds to antigens. The Fab region is composed of one constant and one variable domain of each of the heavy and the light chains.

As used herein, the term "immunoglobulin G" or "IgG" refers to a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. As used herein, the term "modified immunoglobulin G" refers to a molecule that is derived from an antibody of the "G" class. As used herein, the term "antibody" refers to a protein consisting of one or more polypeptides substantially encoded by all or part of the recognized immunoglobulin genes. The recognized immunoglobulin genes, for example in humans, include the kappa (κ) lambda (λ) and heavy chain genetic loci, which together comprise the myriad variable region genes, and the constant region genes mu (μ) delta (δ), gamma (γ), sigma (σ) and alpha (α) which encode the IgM, IgD, IgG, IgE, and IgA isotypes or classes, respectively. The term "antibody" is meant to include full-length antibodies, and may refer to a natural antibody from any organism, an engineered antibody, or an antibody generated recombinantly for experimental, therapeutic, or other purposes as further defined below. Furthermore, full-length antibodies comprise conjugates as described and exemplified herein. As used herein, the term "antibody" comprises monoclonal and polyclonal antibodies. Antibodies can be antagonists, agonists, neutralizing, inhibitory, or stimulatory. Specifically included within the definition of "antibody" are full-length antibodies described and exemplified herein. By "full length antibody" herein is meant the structure that constitutes the natural biological form of an antibody, including variable and constant regions.

The "variable region" of an antibody contains the antigen binding determinants of the molecule, and thus determines the specificity of an antibody for its target antigen. The variable region is so named because it is the most distinct in sequence from other antibodies within the same isotype. The majority of sequence variability occurs in the complementarity determining regions (CDRs). There are 6 CDRs total, three each per heavy and light chain, designated VH CDR1, VH CDR2, VH CDR3, VL CDR1, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens.

Furthermore, antibodies may exist in a variety of other forms including, for example, Fv, Fab, and (Fab')2, as well as bi-functional (i.e. bi-specific) hybrid antibodies (e.g., Lanzavecchia et al., Eur. J. Immunol. 17:105 (1987)) and in single chains (e.g., Huston et al., Proc. Natl. Acad. Sci. U.S.A., 85:5879-5883 (1988) and Bird et al., Science, 242: 423-426 (1988), which are incorporated herein by reference). (See, generally, Hood et al., "Immunology", Benjamin, N.Y., 2nd ed. (1984), and Hunkapiller and Hood, Nature, 323:15-16 (1986)).

The term "epitope" as used herein refers to a region of an antigen that binds to the antibody or antigen-binding fragment. It is the region of an antigen recognized by a first antibody wherein the binding of the first antibody to the region prevents binding of a second antibody or other bivalent molecule to the region. The region encompasses a particular core sequence or sequences selectively recognized by a class of antibodies. In general, epitopes are comprised by local surface structures that can be formed by contiguous or noncontiguous amino acid sequences.

As used herein, the terms "selectively recognizes", "selectively bind" or "selectively recognized" mean that binding of the antibody, antigen-binding fragment or other bivalent molecule to an epitope is at least 2-fold greater, preferably 2-5 fold greater, and most preferably more than 5-fold greater than the binding of the molecule to an unrelated epitope or than the binding of an antibody, antigen-binding fragment or other bivalent molecule to the epitope, as determined by techniques known in the art and described herein, such as, for example, ELISA or cold displacement assays.

As used herein, the term "antibody" encompasses the structure that constitutes the natural biological form of an antibody. In most mammals, including humans, and mice, this form is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In each pair, the light and heavy chain variable regions (VL and VH) are together responsible for binding to an antigen, and the constant regions (CL, Cγ1, Cγ2, and Cγ3, particularly Cγ2, and Cγ3) are responsible for antibody effector functions. In some mammals, for example in camels and llamas, full-length antibodies may consist of only two heavy chains, each heavy chain comprising immunoglobulin domains VH, Cγ2, and Cγ3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains including but not limited to VH, Cγ1, Cγ2, Cγ3, VL, and CL.

Depending on the amino acid sequence of the constant domain of their heavy chains, intact antibodies can be assigned to different "classes". There are five-major classes (isotypes) of intact antibodies: IgA, IgD, IgE, IgG, and IgM, and several of these may be further divided into "sub-classes", e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known to one skilled in the art.

In one embodiment, the term "antibody" or "antigen-binding fragment" respectively refer to intact molecules as well as functional fragments thereof, such as Fab, a scFv-Fc bivalent molecule, F(ab')2, and Fv that are capable of specifically interacting with a desired target. In some embodiments, the antigen-binding fragments comprise:

(1) Fab, the fragment which contains a monovalent antigen-binding fragment of an antibody molecule, which can be produced by digestion of whole antibody with the enzyme papain to yield an intact light chain and a portion of one heavy chain;
(2) Fab', the fragment of an antibody molecule that can be obtained by treating whole antibody with pepsin, followed by reduction, to yield an intact light chain and a portion of the heavy chain; two Fab' fragments are obtained per antibody molecule;
(3) (Fab')2, the fragment of the antibody that can be obtained by treating whole antibody with the enzyme pepsin without subsequent reduction; F(ab')2 is a dimer of two Fab' fragments held together by two disulfide bonds;
(4) Fv, a genetically engineered fragment containing the variable region of the light chain and the variable region of the heavy chain expressed as two chains; and
(5) Single chain antibody ("SCA"), a genetically engineered molecule containing the variable region of the light chain and the variable region of the heavy chain, linked by a suitable polypeptide linker as a genetically fused single chain molecule.
(6) scFv-Fc, is produced in one embodiment, by fusing single-chain Fv (scFv) with a hinge region from an immunoglobulin (Ig) such as an IgG, and Fc regions.

In some embodiments, an antibody provided herein is a monoclonal antibody. In some embodiments, the antigen-binding fragment provided herein is a single chain Fv (scFv), a diabody, a tandem scFv, a scFv-Fc bivalent molecule, an Fab, Fab', Fv, F(ab')2 or an antigen binding scaffold (e.g., affibody, monobody, anticalin, DARPin, Knottin, etc.). "Affibodies" are small proteins engineered to bind to a large number of target proteins or peptides with high affinity, often imitating monoclonal antibodies, and are antibody mimetics.

As used herein, the terms "bivalent molecule" or "BV" refer to a molecule capable of binding to two separate targets at the same time. The bivalent molecule is not limited to having two and only two binding domains and can be a polyvalent molecule or a molecule comprised of linked monovalent molecules. The binding domains of the bivalent molecule can selectively recognize the same epitope or different epitopes located on the same target or located on a target that originates from different species. The binding domains can be linked in any of a number of ways including, but not limited to, disulfide bonds, peptide bridging, amide bonds, and other natural or synthetic linkages known in the art (Spatola et al., "Chemistry and Biochemistry of Amino Acids, Peptides and Proteins," B. Weinstein, eds., Marcel Dekker, New York, p. 267 (1983) (general review); Morley, J. S., "Trends Pharm Sci" (1980) pp. 463-468 (general review); Hudson et al., Int J Pept Prot Res (1979) 14, 177-185; Spatola et al., Life Sci (1986) 38, 1243-1249; Hann, M. M., J Chem Soc Perkin Trans I (1982) 307-314; Almquist et al., J Med Chem (1980) 23, 1392-1398; Jennings-White et al., Tetrahedron Lett (1982) 23, 2533; Szelke et al., European Application EP 45665; Chemical Abstracts 97, 39405 (1982); Holladay, et al., Tetrahedron Lett (1983) 24, 4401-4404; and Hruby, V. J., Life Sci (1982) 31, 189-199).

As used herein, the terms "binds" or "binding" or grammatical equivalents, refer to compositions having affinity for each other. "Specific binding" is where the binding is selective between two molecules. A particular example of specific binding is that which occurs between an antibody and an antigen. Typically, specific binding can be distinguished from non-specific when the dissociation constant (KD) is less than about $1\times10^{-5}$ M or less than about $1\times10^{-6}$ M or $1\times10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding.

In some embodiments, the present invention comprises a first component protein comprising a first binding pair partner and a second component protein comprising a second binding pair partner, wherein the binding pair partners comprise two protein moieties that form a heterodimer.

A "dimer" is a macromolecular complex formed by two macromolecules, usually proteins (or portions thereof) or nucleic acids (or portions thereof). A "homodimer" is formed by two identical macromolecules ("homodimerization"), while a "heterodimer" is formed by two distinct macromolecules ("heterodimerization"). Many dimers are non-covalently linked, but some (e.g., NEMO homodimers) can link via, e.g., disulfide bonds. Some proteins comprise regions specialized for dimerization, known as "dimerization domains." In some instances, a truncated protein containing or comprising a dimerization domain (or two truncated proteins containing or comprising corresponding dimerization domains) may be able to interact in the absence of one or both complete protein sequence(s). Similarly, a fusion protein comprising a dimerization domain (or two fusion proteins comprising corresponding dimerization domains) may be able to interact in the absence of one or both complete protein sequence(s). Mutations to these domains may increase, or alternatively reduce, the formation of a dimer. Examples of macromolecules that can form dimers include, but are not limited to, proteins, nucleic acids, antibodies, receptor tyrosine kinases, proteins with leucine zippers, peptide Velcro, nuclear receptors, 14-3-3 proteins, G proteins, G protein-coupled receptors, transcription factors, kinesin, triosephosphate isomerase (TIM), alcohol dehydrogenase, Toll-like receptors, fibrinogen, tubulin, some glycoproteins, and some clotting factors. Additional examples of particular pairs include, but are not limited to, c-Jun/c-Fos, RelA (or c-Rel or RelB)/p50 (or p51) (Rel/NF-kappaB), AP-1, C/EBP, ATF/CREB, c-Myc, and NF-1

In one embodiment, the antibody or antigen-binding fragment binds its target with a KD of 0.1 nM-10 mM. In one embodiment, the antibody or antigen-binding fragment binds its target with a KD of 0.1 nM-1 mM. In one embodiment, the antibody or antigen-binding fragment binds its target with a KD within the 0.1 nM range. In one embodiment, the antibody or antigen-binding fragment binds its target with a KD of 0.1-2 nM. In another embodiment, the antibody or antigen-binding fragment binds its target with a KD of 0.1-1 nM. In another embodiment, the antibody or antigen-binding fragment binds its target with a KD of 0.05-1 nM. In another embodiment, the antibody or antigen-binding fragment binds its target with a KD of 0.1-0.5 nM. In another embodiment, the antibody or antigen-binding fragment binds its target with a KD of 0.1-0.2 nM.

In some embodiments, the antibody or antigen-binding fragment thereof provided herein comprises a modification. In another embodiment, the modification minimizes conformational changes during the shift from displayed to secreted forms of the antibody or antigen-binding fragment. It is to be understood by a skilled artisan that the modification can be a modification known in the art to impart a functional property that would not otherwise be present if it were not for the presence of the modification. Encompassed are antibodies which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

In some embodiments, the modification is one as further defined herein below. In some embodiments, the modification is an N-terminus modification. In some embodiments, the modification is a C-terminal modification. In some embodiments, the modification is an N-terminus biotinylation. In some embodiments, the modification is an C-terminus biotinylation. In some embodiments, the secretable form of the antibody or antigen-binding fragment comprises an N-terminal modification that allows binding to an Immunoglobulin (Ig) hinge region. In some embodiments, the Ig hinge region is from but is not limited to, an IgA hinge region. In some embodiments, the secretable form of the antibody or antigen-binding fragment comprises an N-terminal modification that allows binding to an enzymatically biotinylatable site. In some embodiments, the secretable form of the antibody or antigen-binding fragment comprises an C-terminal modification that allows binding to an enzymatically biotinylatable site. In some embodiments, biotinylation of said site functionilizes the site to bind to a surface coated with streptavidin, avidin, avidin-derived moieties, or a secondary reagent.

It will be appreciated that the term "modification" can encompass an amino acid modification such as an amino acid substitution, insertion, and/or deletion in a polypeptide sequence.

In one embodiment, a variety of radioactive isotopes are available for the production of radioconjugate antibodies and other proteins and can be of use in the methods and compositions provided herein. Examples include, but are not limited to, At211, Cu64, I131, I125, Y90, Re186, Re188, Sm153, Bi212, P32, Zr89 and radioactive isotopes of Lu.

In an alternate embodiment, enzymatically active toxin or fragments thereof that can be used in the compositions and methods provided herein include, but are not limited, to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

A chemotherapeutic or other cytotoxic agent may be conjugated to the protein, according to the methods provided herein, as an active drug or as a prodrug. The term "prodrug" refers to a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; and Stella et al., "Prodrugs: A Chemical Approach to Targeted Drug Delivery," Directed Drug Delivery, Borchardt et al., (ed.): 247-267, Humana Press, 1985. The prodrugs that may find use with the compositions and methods as provided herein include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies and Fc fusions of the compositions and methods as provided herein include but are not limited to any of the aforementioned chemotherapeutic.

In one embodiment, a combination of the protein with the biological active agents specified above, i.e., a cytokine, an enzyme, a chemokine, a radioisotope, an enzymatically active toxin, or a chemotherapeutic agent can be applied.

In one embodiment, a variety of other therapeutic agents may find use for administration with the antibodies and conjugates of the compositions and methods provided herein. In one embodiment, the conjugate comprising an antibody is administered with an anti-angiogenic agent. As used herein, the term "anti-angiogenic agent" refers to a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. In an alternate embodiment, the conjugate is administered with a therapeutic agent that induces or enhances adaptive immune response. In an alternate embodiment, the conjugate is administered with a tyrosine kinase inhibitor. The term "tyrosine kinase inhibitor" refers to a molecule that inhibits to some extent tyrosine kinase activity of a tyrosine kinase as known in the art.

In one embodiment, the conjugates provided herein may be used for various therapeutic purposes. In one embodiment, the conjugates are administered to a subject to treat an antibody-related disorder. In another embodiment, the conjugate proteins are administered to a subject to treat a tumor or a cancer tumor. A "subject" for the purposes of the compositions and methods provided herein includes humans and other animals, preferably mammals and most preferably humans. Thus the conjugates provided herein have both human therapy and veterinary applications. In another embodiment the subject is a mammal, and in yet another embodiment the subject is human. By "condition" or "disease" herein are meant a disorder that may be ameliorated by the administration of a pharmaceutical composition comprising the conjugate of the compositions and methods provided herein. Antibody related disorders include but are not limited to autoimmune diseases, immunological diseases, infectious diseases, inflammatory diseases, neurological diseases, and oncological and neoplastic diseases including cancer.

In another embodiment, provided herein is a nucleic acid construct encoding the conjugate provided herein. In some embodiments, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotides. This term includes oligonucleotides composed of naturally occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, provided herein are primers used for amplification and construction of the vectors and nucleic acids provided herein. It is to be understood by a skilled artisan that other primers can be used or designed to arrive at the vectors, nucleic acids and conjugates provided herein.

In one embodiment, provided herein is a vector comprising the nucleic acid encoding for the conjugate components provided herein. In another embodiment, the vector comprises nucleic acid encoding the protein, polypeptides, peptides, antibodies, and recombinant fusions provided herein.

In another embodiment, the nucleic acid can be expressed in a variety of different systems, in vitro and in vivo, according to the desired purpose. For example, a nucleic acid can be inserted into an expression vector, introduced into a desired host, and cultured under conditions effective to achieve expression of a polypeptide coded for by the nucleic acid. Effective conditions include culture conditions which are suitable for achieving production of the polypeptide by the host cell, including effective temperatures, pH, medusa, additives to the media in which the host cell is cultured (e.g., additives which amplify or induce expression such as butyrate, or methotrexate if the coding nucleic acid is adjacent to a dhfr gene), cycloheximide, cell densities, culture dishes, etc. In another embodiment, a nucleic acid can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which the nucleic acid provided herein has been introduced is a transformed host cell. The nucleic acid can be extrachromosomal or integrated into a chromosome(s) of the host cell. It can be stable or transient. An expression vector is selected for its compatibility with the host cell. Host cells include, mammalian cells (e.g., COS-7, CVI, BHK, CHO, HeLa, LTK, NIH 3T3, 293, PAE, human, human fibroblast, human primary tumor cells, testes cells), insect cells, such as Sf9 (*S. frugipeda*) and *Drosophila*, bacteria, such as *E. coli, Streptococcus, bacillus*, yeast, such as *S. cerevisiae* (e.g., cdc mutants, cdc25, cell cycle and division mutants, such as ATCC Nos. 42563, 46572, 46573, 44822, 44823, 46590, 46605, 42414, 44824, 42029, 44825, 44826, 42413, 200626, 28199, 200238, 74155, 44827, 74154, 74099, 201204, 48894, 42564, 201487, 48893, 28199, 38598, 201391, 201392), fungal cells, plant cells, embryonic stem cells (e.g., mammalian, such as mouse or human), fibroblasts, muscle cells, neuronal cells, etc. Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, promoters of other genes in the cell signal transduction pathway, MMTV, SV40, trp, lac, tac, or T7 promoters for bacterial hosts; or alpha factor, alcohol oxidase, or PGH promoters for yeast.

In one embodiment, reporter genes may be incorporated within expression constructs to facilitate identification of transcribed products. Accordingly and in one embodiment of the compositions and methods provided herein, reporter genes utilized are selected from the group consisting of β-galactosidase, chloramphenicol acetyl transferase, luciferase and a fluorescent protein.

In one embodiment, the conjugates are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of conjugates. For example, the bacterial proteins A and G bind to the Fc region. Likewise, the bacterial protein L binds to the Fab region of some antibodies, as of course does the antibody's target antigen. Purification can often be enabled by a particular fusion partner. For example, proteins may be purified using glutathione resin if a GST fusion is employed, Ni+2 affinity chromatography if a His-tag is employed, or immobilized anti-flag antibody if a flag-tag is used. The degree of purification necessary will vary depending on the screen or use of the conjugates. In some instances no purification is necessary. For example in one embodiment, if the conjugates are secreted, screening may take place directly from the media. As is well known in the art, some methods of selection do not involve purification of proteins. Thus, for example, if a library of conjugates is made into a phage display library, protein purification may not be performed.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, when referring to a measurable value such as an amount, a temporal duration, a concentration, and the like, may encompass variations of ±20% or ±10%, more preferably ±5%, even more preferably ±1%, and still more preferably ±0.1% from the specified value, as such variations are appropriate to perform the disclosed methods.

There are many options for linking modules. A variety of linkers may find use in the compositions and methods provided herein to generate conjugates. The term "linker," "linker sequence," "spacer," "tethering sequence" or grammatical equivalents thereof refer to a molecule or group of molecules (such as a monomer or polymer) that connects two molecules and often serves to place the two molecules in a preferred configuration. A number of strategies may be used to covalently link molecules together. These include, but are not limited to polypeptide linkages between N- and C-terminus of proteins or protein domains, linkage via disulfide bonds, and linkage via chemical cross-linking reagents. In one aspect of this embodiment, the linker is a peptide bond, generated by recombinant techniques or peptide synthesis. In another embodiment the linker is a cysteine linker. In yet another embodiment, it is a multi-cysteine linker. Choosing a suitable linker for a specific case where two polypeptide chains are to be connected depends on various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 30 amino acid residues. In one embodiment, the linker is from about 1 to 30 amino acids in length. In another embodiment, the linker is from about 1 to 15 amino acids in length. In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers, glycine-alanine polymers, alanine-serine polymers, and other flexible linkers such as the tether for the shaker potassium channel, and a large variety of other flexible linkers, as will be appreciated by those in the art. Suitable linkers may also be identified by screening databases of known three-dimensional structures for naturally occurring motifs that can bridge the gap between two polypeptide chains. In one embodiment, the linker is not immunogenic when administered in a human subject. Thus linkers may be chosen such that they have low immunogenicity or are thought to have low immunogenicity. Another way of obtaining a suitable linker is by optimizing a simple linker, e.g., (Gly4Ser)n, through random mutagenesis. Alternatively, once a suitable polypeptide linker is defined, additional linker polypeptides can be created to select amino acids that more optimally interact with the domains being linked. Other types of linkers that may be used in the compositions and methods provided herein include artificial polypeptide linkers and inteins. In another embodiment, disulfide bonds are designed to link the two molecules. In another embodiment, linkers are chemical cross-linking agents. For example, a variety of bifunctional protein coupling agents may be used, including but not limited to N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene). In another embodiment, chemical linkers may enable chelation of an isotope. For example, Carbon-14-labeled 1-isothiocyanatobenzyl-3-methyldiethylene triaminepentaacetic acid (MX-DTPA) is an exemplary chelating agent for conjugation of radionucleotide to the antibody. The linker may be cleavable, facilitating release of the cytotoxic drug in the cell. For example, an acid-labile linker, peptidase-sensitive linker, dimethyl linker or disulfide-containing linker (Chari et al., 1992, Cancer Research 52: 127-131) may be used. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the components of the conjugates of the compositions and methods provided herein.

In one aspect, provided herein are binding pair partners.

SpyCatcher and SpyTag. One component protein can be fused to SpyCatcher and a second component protein can be fused to SpyTag. See Zakeri et al., "Peptide tag forming a rapid covalent bond to a protein, through engineering a bacterial adhesin" PNAS (2012) vol. 109 no. 12, pgs. E690-E697, doi: 10.1073/pnas.1115485109, which is hereby incorporated by reference in its entirety.

Split inteins (or other intein-based systems). One component protein can be fused to one half of the split intein and the other can be fused to the other half.

Heterodimeric proteins that have an affinity for each other (e.g., c-Fos and c-Jun, leucine zippers, peptide velcro, etc.) can also be used.

Dock-and-lock. This system involves two docking proteins, which are fused to the component proteins. These proteins bring together the two component proteins. Then a third peptide is used to covalently link the two docking proteins together.

Click chemistries. One component protein can be modified with an azide and the other with an alkyne or constrained alkyne (e.g., ADIBO or DBCO). Other popular click chemistries exist (e.g. tetrazine and TCO). Click chemistries can be incorporated using various techniques, e.g. intein-mediated expressed protein ligation, sortase, sortase-tag expressed protein ligation, non-natural amino acid incorporation, maleimide chemistry, carbodiimide chemistry, NHS chemistry, aldehyde chemistry, chemoenzymatic approaches (e.g. lipoic acid ligase, formylglycine), etc.

Pharmaceutical compositions are contemplated wherein the compositions and methods provided herein and one or more therapeutically active agents are formulated. Formulations of the conjugates of the compositions and methods provided herein are prepared for storage by mixing said a conjugated protein having the desired degree of purity with optional pharmaceutically acceptable carriers, excipients or stabilizers, in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants or polyethylene glycol (PEG). In another embodiment, the pharmaceutical composition that comprises the conjugate of the compositions and methods provided herein is in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

The conjugate molecules disclosed herein may also be formulated as immunoliposomes. A liposome is a small vesicle comprising various types of lipids, phospholipids and/or surfactant that is useful for delivery of a therapeutic agent to a mammal. Liposomes containing the conjugates are prepared by methods known in the art, such as described in Epstein et al., 1985, PNAS, 82:3688; Hwang et al., 1980, PNAS, 77:4030; U.S. Pat. Nos. 4,485,045; 4,544,545; and PCT WO 97/38731. Liposomes with enhanced circulation time are disclosed in U.S. Pat. No. 5,013,556. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, J National Cancer Inst 81:1484).

The conjugate molecules provided herein may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethylmethacrylate), or poly(vinylalcohol)), polylactides (U.S. Pat. No. 3,773,919), copolymers of L-glutamic acid and gamma ethyl-L-glutamate, non-degradable ethylene-vinyl acetate, degradable lactic acid-glycolic acid copolymers (which are injectable microspheres composed of lactic acid-glycolic acid copolymer and leuprolide acetate), and poly-D-(−)-3-hydroxybutyric acid) which is a microsphere-based delivery system composed of the desired bioactive molecule incorporated into a matrix of poly-DL-lactide-co-glycolide (PLG).

The conjugate molecules may also be linked to the surfaces of nanoparticles using the linking methods provided herein. In one embodiment, the nanoparticles can be used for imaging or therapeutic purposes.

Administration of the pharmaceutical composition comprising the conjugates provided herein, preferably in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. As is known in the art, the pharmaceutical composition may be formulated accordingly depending upon the manner of introduction.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

As used herein, the singular forms "a," "an," and "the" include plural references unless the context clearly dictates otherwise. For example, the term "a molecule" can also include a plurality of molecules.

This proximity-based sortase-mediated expressed protein ligation system offers a number of features that make it a very favorable approach for bioconjugation reactions. First and foremost, proximity-based sortase-mediated expressed protein ligation combines release of recombinant proteins from the affinity column and bioconjugation into a single step. This greatly simplifies the entire bioconjugation procedure, saving time, money, and complexity. Second, proximity-based sortase-mediated expressed protein ligation allows for the site-specific conjugation of cargo. Site-specific functionalization has been shown to be beneficial in a number of applications including the preparation of protein-drug conjugates, which often exhibit higher efficacy than randomly labeled targeting ligands. It has also been shown that the site-specific attachment of targeting ligands to nanoparticles can improve nanoparticle avidity. Third, proximity-based sortase-mediated expressed protein ligation conjugates the peptide-to-ligand in a 1:1 stoichiometric manner. This can be important when labeling targeting ligands with imaging agents, since it allows for precise quantitative imaging. It is also beneficial for characterizing nanoparticle bioconjugations. Fourth, the conditions used to release protein from the affinity column can be manipulated to ensure that essentially all of the recovered protein is conjugated with the desired cargo. This eliminates the often-difficult process of purifying conjugated products from unconjugated proteins. Since in many applications a large protein is labeled with low molecular weight drugs or imaging agents, the conjugated and unconjugated forms of the protein can differ by as little as a few hundred to a few thousand Da, potentially without a significant change to hydrophobicity or charge. A slight excess of peptide is required to achieve complete ligation; however, excess peptide is easily removed via dialysis or gel chromatography. This purification step is analogous to the removal of, e.g., imidazole from His-tagged protein samples that have been affinity purified using a nickel column. Fifth, in contrast to STEPL, construction of the proximity-based sortase-mediated expressed protein ligation system as a two-construct, proximity-based sortase-mediated protein purification and ligation method can yield improved results over the single-step/single-construct method in which sortase is fused directly to the expressed protein. Although this latter method works well with shorter proteins, in some instances, the sortase interferes with the proper folding of larger or more complex proteins (e.g., scFv proteins), thereby disrupting the secondary structure of the protein of interest, and additionally, this approach may be incompatible with protein expression systems where calcium is present (e.g., yeast and mammalian systems).

In sum, provided herein is a flexible and efficient system for molecular imaging and targeted therapeutics. Moreover, because it has the ability to link virtually any bacterially expressible protein with any cargo that can be attached, e.g., to a triglycine peptide, it has applications in many fields.

Any patent, patent application publication, or scientific publication, cited herein, is incorporated by reference herein in its entirety.

The following examples are presented in order to more fully illustrate the preferred embodiments of the invention. They should in no way be construed, however, as limiting the broad scope of the invention.

EXAMPLES

Example 1: Proximity-Based Sortase-Tag Expressed Protein Ligation (STEPL): Combining Protein Purification and Site-Specific Bioconjugation Using Bindings Partners Generally, in one embodiment, proximity-based sortase ligation is an expressed protein ligation technique with 2 components. The first comprises a fusion protein containing sortase (Srt), a calcium-dependent transpeptidase, as well as one member of a binding partner protein pair (BP-B) (FIG. 1). The binding partner protein entity can be placed either N-terminal (FIG. 1—upper right) or C-terminal (FIG. 1—upper center) to sortase. Either protein is connected via a glycine/serine-rich linker. An affinity tag is placed at the C-terminal end of the fusion protein.

For the first portion of the technique (FIG. 1—1.), the fusion protein is expressed and then isolated on an affinity resin corresponding to the affinity tag (FIG. 1—middle center or FIG. 1—middle right). Possible affinity tag/resin pairings include, but are not limited to, His tag/nickel or cobalt resin, chitin-binding domain/chitin resin, and biotinylated biotin acceptor peptide/streptavidin.

The second component is the protein of interest followed by a sortase recognition motif (shown here as LPXTG) and the other member of a binding partner protein pair (BP-A) (FIG. 1—upper left). Possible binding partner protein pairs include, but are not limited to, SpyCatcher/SpyTag, SnoopCatcher/SnoopTag, c-Fos/c-Jun, split inteins, S-protein/S-tag, and Strep-tag or stre-tag II/streptavidin or streptactin, as well as other binding partner protein pairs described above. The protein of interest with the sortase recognition motif and BP-A is first expressed (e.g., in an E. coli, yeast, or mammalian system) (FIG. 1—2.).

Incubation (e.g., of the bacterial lysate for an E. coli system) with affinity resin containing the sortase-BP-B fusion protein then not only isolates the protein of interest, via the pairing of the binding partner protein elements (FIG. 1—3.), but also brings the sortase recognition motif in close proximity to sortase. Next, adding calcium and a peptide with an N-terminal glycine catalyzes the sortase reaction (FIG. 1—4.). Sortase first cleaves the peptide bond between the threonine and glycine of the LPXTG sortase recognition motif and then ligates the threonine to the N-terminal glycine containing peptide (e.g., GGG). The peptide can consist solely of glycine or may include additional amino acids or chemical groups to further functionalize the protein of interest.

This expressed protein ligation technique results in a minimal final footprint, namely, the protein of interest can be followed immediately by LPXT, and an N-terminal glycine-containing peptide of the researcher's own choosing (FIG. 1—bottom). Alternatively, an amino acid linker (e.g. glycine/serine linker) can be inserted between the protein of interest and the amino acids LPXTG.

Proximity-based sortase ligation utilizes the affinity of a pair of binding partners to achieve protein capture of a protein of interest, followed by subsequent cleavage of the protein and ligation of the sortase recognition peptide onto the protein. By commencing with the sortase and the protein of interest on separate fusion protein constructs, the secondary structure folding of the protein of interest can be achieved prior to interaction with the sortase on the capture fusion protein construct. In addition, in expression systems in which calcium is present, the two constructs can be maintained separately until the time when the interaction is set to take place.

A flexible GS-rich linker (e.g., (GGS)5) between the sortase domain and the binding partner B domain gives the sortase domain the conformational freedom to recognize a sortase recognition motif (e.g., LPXTG), which in turn is flexibly linked to the domain of a protein of interest, in a bimolecular reaction. The flexible link between the domain of the protein of interest and the binding partner A domain provides further conformation freedom and also reduces or prevents inhibition of conformational folding on the part of the domain of the protein of interest. Adding calcium and a protein/peptide with an N-terminal glycine or polyglycine (and attached cargo, if desired) activates the sortase domain, ligating the protein of interest to the peptide while simultaneously cleaving it from the binding partner A domain.

Thus, the conjugate is released while the sortase enzyme and the paired binding partners A and B are retained on the column via the affinity tag (e.g., His-tag). By making purification and conjugation codependent, proximity-based STEPL remains site-specific and stoichiometric in nature, but does not require additional steps to remove Srt or the paired binding partners from the purified protein sample. Further, large excesses of peptide are not essential since only correctly ligated product is released from the affinity column and conditions can be optimized to nearly exhaust any added peptide.

Example 2: Proximity-Based Sortase-Tag Expressed Protein Ligation (STEPL): Combining Protein Purification and Site-Specific Bioconjugation Using Binding Partners In this study, a bacterial sortase enzyme is utilized for targeting ligand purification and site-specific conjugation. This method utilizes two protein constructs, each of which includes a binding sequence for one member of a pair of binding partners (e.g., binding partner A and binding partner B).

Figure 2B:
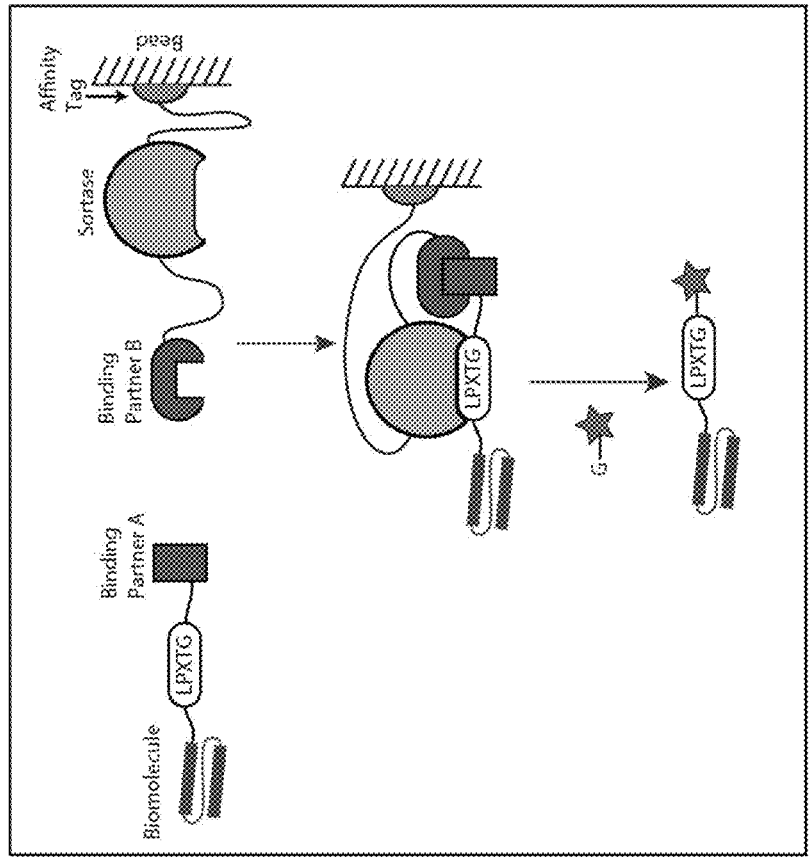
FIG. 2A-2B. Schematics of Proximity-based Sortase Ligation on a Solid Support.
Figure 2A:
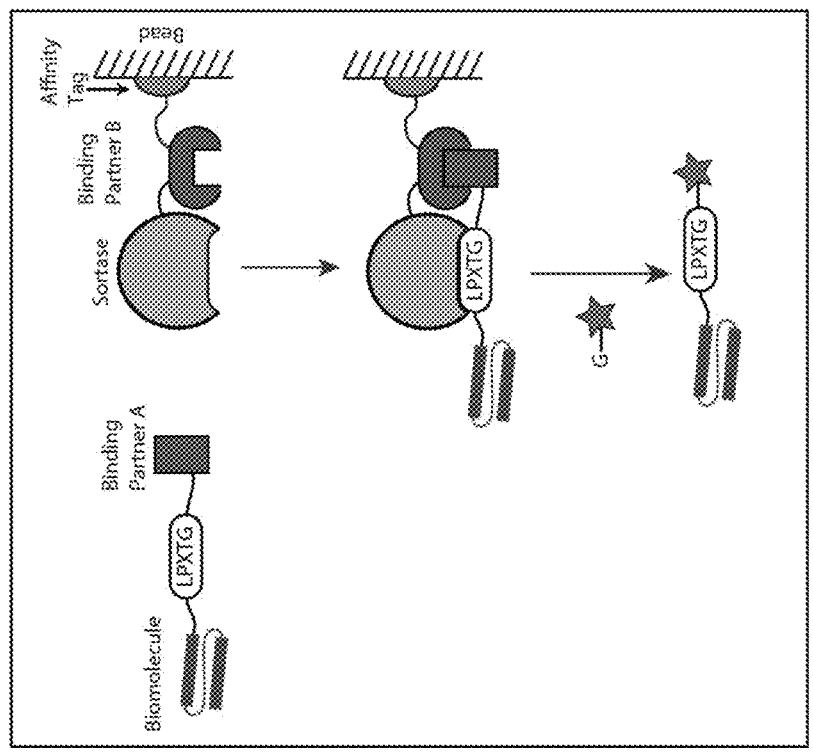

In this Example, to generate the construct for the capture fusion protein, sortase (Srt) (e.g., SrtA) is cloned in frame and in series so that it is placed, with an intervening linker (e.g., a flexible GS-rich linker), N-terminal to binding partner B (BP-B), which, in turn, is N-terminal to an affinity tag (e.g., a His tag) (FIG. 1—center (1.) and FIG. 2A—upper right). This fusion protein is then expressed and isolated on an affinity resin (e.g., an affinity column or beads) via the affinity tag (FIG. 1—center (1.) and FIG. 2A—upper right).

In parallel, for the second protein construct, a protein of interest is cloned in frame and in series with a sortase recognition motif (e.g., LPXTG), and binding partner A (BP-A) (FIG. 1—left (2.) and FIG. 2A—upper left). The fusion protein comprising the protein of interest is then expressed (FIG. 1—left (2.) and FIG. 2A—upper left).

The fusion protein comprising the protein of interest is captured onto the affinity resin through the interaction between binding partners A and B (FIG. 1—center (3.) and FIG. 2A—middle right). Adding both calcium and a peptide with an N-terminal glycine or polyglycine (e.g., GGG) (and attached cargo, if desired) allows sortase simultaneously to cleave the protein of interest from the affinity resin and to ligate the peptide onto the protein (FIG. 1—center (4.) and FIG. 2A—bottom right). If desired, the peptide/protein is labeled with a chemical or biological moiety (e.g., imaging agent, drug, click chemistry group, hapten, oligonucleotide, etc.) (indicated by stars in FIG. 1—center (4.) and FIG. 2A—bottom right).

Example 3: Proximity-Based Sortase-Tag Expressed Protein Ligation (STEPL): Combining Protein Purification and Site-Specific Bioconjugation Using Binding Partners Similar to the study of Example 2, in this study, a bacterial sortase enzyme is also utilized for purification and site-specific conjugation of a protein of interest. This method also utilizes two protein constructs, each of which includes a binding sequence for one member of a pair of binding partners (e.g., binding partner A and binding partner B).

In this Example, to generate the construct for the capture fusion protein, sortase (Sr) (e.g., SrtA) is cloned in frame and in series so that it is placed, with an intervening linker (e.g., a flexible GS-rich linker), C-terminal to binding partner B (BP-B) and N-terminal to an affinity tag (e.g., a His tag) (FIG. 1—right (1.) and FIG. 2B—upper right). This fusion protein is then expressed and isolated on an affinity resin (e.g., an affinity column or beads) via the affinity tag (FIG. 1—right (1.) and FIG. 2B—upper right).

In parallel, for the second protein construct, a protein of interest is cloned in frame and in series with a sortase recognition motif (e.g., LPXTG), and binding partner A (BP-A) (FIG. 1—left (2.) and FIG. 2B—upper left). The fusion protein comprising the protein of interest is then expressed (FIG. 1—left (2.) and FIG. 2B—upper left).

The fusion protein comprising the protein of interest is captured onto the affinity resin through the interaction between binding partners A and B (FIG. 1—right (3.) and FIG. 2B—middle right). Adding both calcium and a peptide with an N-terminal glycine or polyglycine (e.g., GGG) (and attached cargo, if desired) allows sortase simultaneously to cleave the protein of interest from the affinity resin and to ligate the peptide onto the protein (FIG. 1—right (4.) and FIG. 2B—bottom right). If desired, the peptide/protein can be labeled with a chemical or biological moiety (e.g., imaging agent, drug, click chemistry group, hapten, oligonucleotide, etc.) (indicated by stars in FIG. 1—center (4.) and FIG. 2B—bottom right).

Examples 4 and 5: Proximity-Based Sortase-Tag Expressed Protein Ligation (STEPL): Additional Purification of the Construct with the Domain of the Protein of Interest In Example 4, to generate the construct for the capture fusion protein, sortase (Srt) is cloned in frame and in series so that it is placed, with an intervening linker (e.g., a flexible GS-rich linker) N-terminal to binding partner B (BP-B), which, in turn, is N-terminal to a first affinity tag (FIG. 3—upper right; see also Examples 1 and 2 and FIGS. 1 and 2A), and the capture fusion protein is expressed and isolated on a first affinity resin.

Alternatively, in Example 5, to generate the construct for the capture fusion protein, sortase (Srt) is cloned in frame and in series so that it is placed, with an intervening linker (e.g., a flexible GS-rich linker) C-terminal to binding partner B (BP-B) and N-terminal to a first affinity tag (see also Example 1 and 3 and FIGS. 1 and 2B), and the capture fusion protein is expressed and isolated on a first affinity resin.

Figure 3:
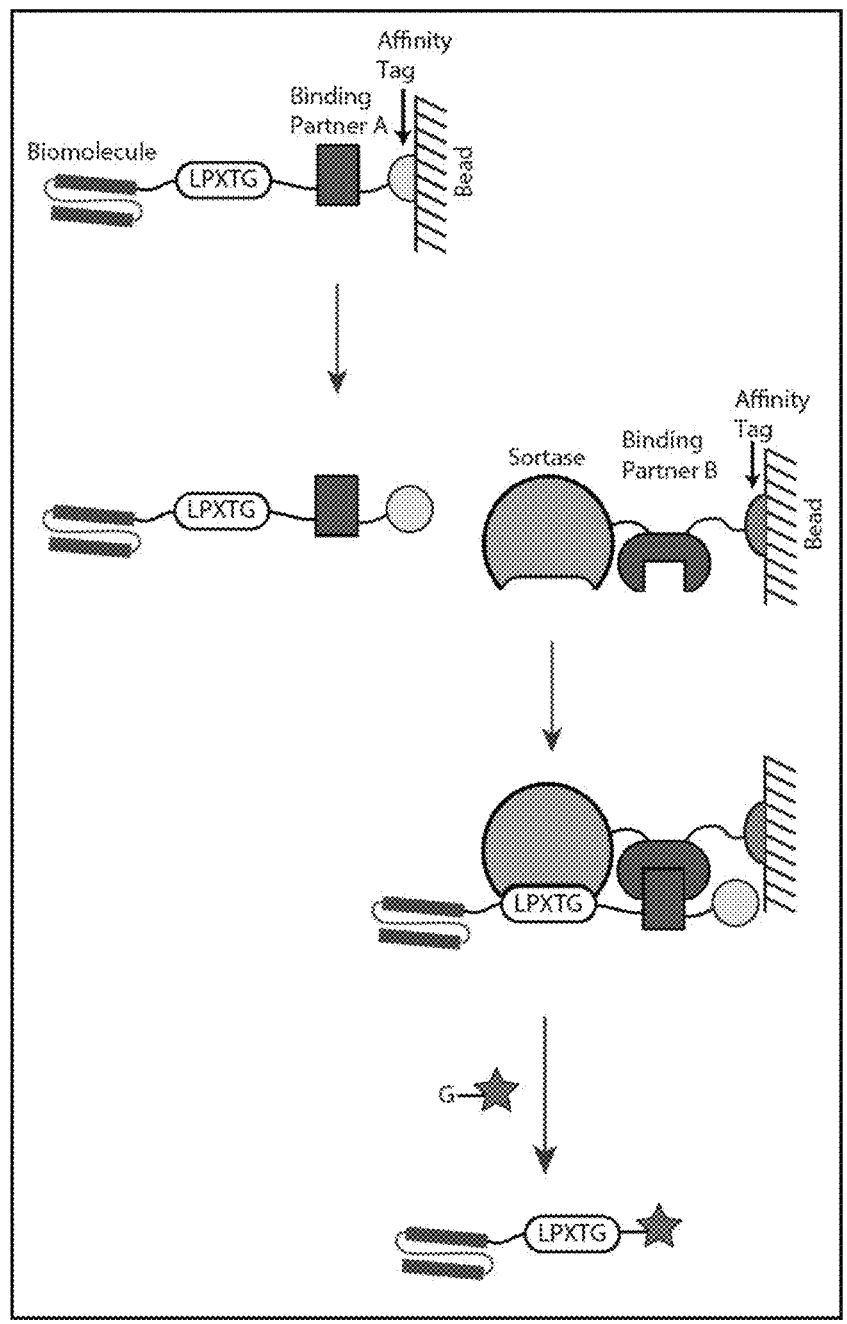
FIG. 3. Schematic of Proximity-based Sortase Ligation on a Solid Support after Pre-purification of the Biomolecule of Interest. A sortase enzyme is expressed in frame with one member of a binding pair (Binding Partner B) and a first affinity tag. The resulting sortase fusion protein is bound to a first affinity column or other solid support. In parallel, a biomolecule of interest is expressed in frame with a sortase recognition motif, the other member of a binding pair (Binding Partner A), and a second affinity tag. The affinity tag may be the same or distinct from the first affinity tag. The resulting biomolecule fusion protein is bound to a second affinity column or other solid support and is then purified by standard affinity purification. Subsequently, the biomolecule can be captured by the Sortase-Binding Partner B-Second Affinity Tag construct via interaction of the binding pairs. (Alternatively, the biomolecule is captured prior to the binding of the sortase fusion protein to the affinity column or other solid support.) The biomolecule is then released from the affinity column upon sortase-based cleavage and ligation to any peptide/protein with an N-terminal glycine. If desired, the peptide/protein can be labeled with a chemical or biological moiety (e.g. imaging agent, drug, click chemistry group, hapten, oligonucleotide, etc.), indicated by the green star. The sortase construct can then be removed from the sample via an affinity column/beads.

In parallel, for the second fusion protein construct, a protein of interest is cloned in frame and in series with a sortase recognition motif (e.g., LPXTG), a binding partner A (BP-A), and a second affinity tag, which may be different than the first affinity tag (FIG. 3—upper left). The second fusion protein construct, comprising the domain of the protein of interest, is expressed and purified on a second affinity resin (FIG. 3—upper left). Linkers can optionally be placed between the protein of interest and sortase recognition motif, between the sortase recognition motif and BP-A, and/or between BP-A and the second affinity tag.

Following purification and release, the second fusion protein is captured on the first affinity resin through the interaction between binding partners A and B (FIG. 3—middle right). (Alternatively, the biomolecule is captured prior to the binding of the sortase fusion protein to the affinity column or other solid support.) Adding both calcium and a peptide with an N-terminal glycine or polyglycine (e.g., GGG) (and attached cargo, if desired) allows sortase simultaneously to cleave the protein of interest from the first affinity resin and to ligate the peptide onto the protein (FIG. 3—bottom right). If desired, the peptide/protein is labeled with a chemical or biological moiety (e.g. imaging agent, drug, click chemistry group, hapten, oligonucleotide, etc.) (indicated by the green star in FIG. 3—bottom right). The sortase construct can then be removed from the sample via an affinity column/beads.

Examples 6 and 7: Proximity-Based Sortase Protein Ligation: Purification of the Construct with the Domain of the Protein of Interest on the Capture Fusion Protein In these reverse Examples, the capture fusion protein comprises the domain of the protein of interest. To generate the construct for the capture fusion protein, the coding sequence for the protein of interest is cloned in frame and in series with a sortase recognition motif (e.g., LPXTG), a binding partner A (BP-A), and an affinity tag, and is then expressed and isolated on an affinity resin.

In Example 6, to generate the construct for the sortase fusion protein, sortase (Srt) is cloned in frame and in series so that it is placed, with an intervening linker (e.g., a flexible GS-rich linker), N-terminal to binding partner B (BP-B), and the sortase fusion protein is expressed.

Alternatively, in Example 7, to generate the construct for the sortase fusion protein, sortase (Srt) is cloned in frame and in series so that it is placed, with an intervening linker (e.g., a flexible GS-rich linker), C-terminal to binding partner B (BP-B), and the sortase fusion protein is expressed.

In these Examples, the sortase fusion protein is captured on the affinity resin through the interaction between binding partners A and B. Adding both calcium and a peptide with an N-terminal glycine or polyglycine (e.g., GGG) (and attached cargo, if desired) allows sortase simultaneously to cleave the protein of interest from the affinity resin and ligate the peptide onto the protein, which is then purified away from the affinity resin. If desired, the peptide/protein is labeled with a chemical or biological moiety (e.g. imaging agent, drug, click chemistry group, hapten, oligonucleotide, etc.).

Examples 8 and 9: Proximity-Based Sortase Protein Ligation: Purification of the Construct with the Domain of the Protein of Interest on the Capture Fusion Protein and Additional Purification of the Construct with the Sortase Domain In these reverse Examples, the capture fusion protein comprises the domain of the protein of interest.

In Example 8, to generate the construct for the sortase fusion protein, sortase (Srt) is cloned in frame and in series so that it is placed, with an intervening linker (e.g., a flexible GS-rich linker), N-terminal to binding partner B (BP-B), which, in turn, is N-terminal to a first affinity tag, and the sortase fusion protein is expressed and isolated on a first affinity resin.

Alternatively, in Example 9, to generate the construct for the capture fusion protein, sortase (Srt) is cloned in frame and in series so that it is placed, with an intervening linker (e.g., a flexible GS-rich linker), C-terminal to binding partner B (BP-B) and N-terminal to a first affinity tag, and the sortase fusion protein is expressed and isolated on a first affinity resin.

To generate the construct for the capture fusion protein, the coding sequence for the protein of interest is cloned in frame and in series with a sortase recognition motif (e.g., LPXTG), a binding partner A (BP-A), and a second affinity tag and is then expressed and isolated on a second affinity resin.

Following purification and release, the sortase fusion protein is captured on the second affinity resin through the interaction between binding partners A and B. Adding both calcium and a peptide with an N-terminal glycine or polyglycine (e.g., GGG) (and attached cargo, if desired) allows sortase simultaneously to cleave the protein of interest from the second affinity resin and ligate the peptide onto the protein. If desired, the peptide/protein is labeled with a chemical or biological moiety (e.g., imaging agent, drug, click chemistry group, hapten, oligonucleotide, etc.).

Examples 10 and 11: Proximity-Based Sortase Protein Ligation: Reaction in the Absence of Affinity Resin and Subsequent Separation of the Construct with the Sortase Domain In these Examples, the binding partners bind and the reaction takes place in the absence of an affinity resin.

Figure 4:
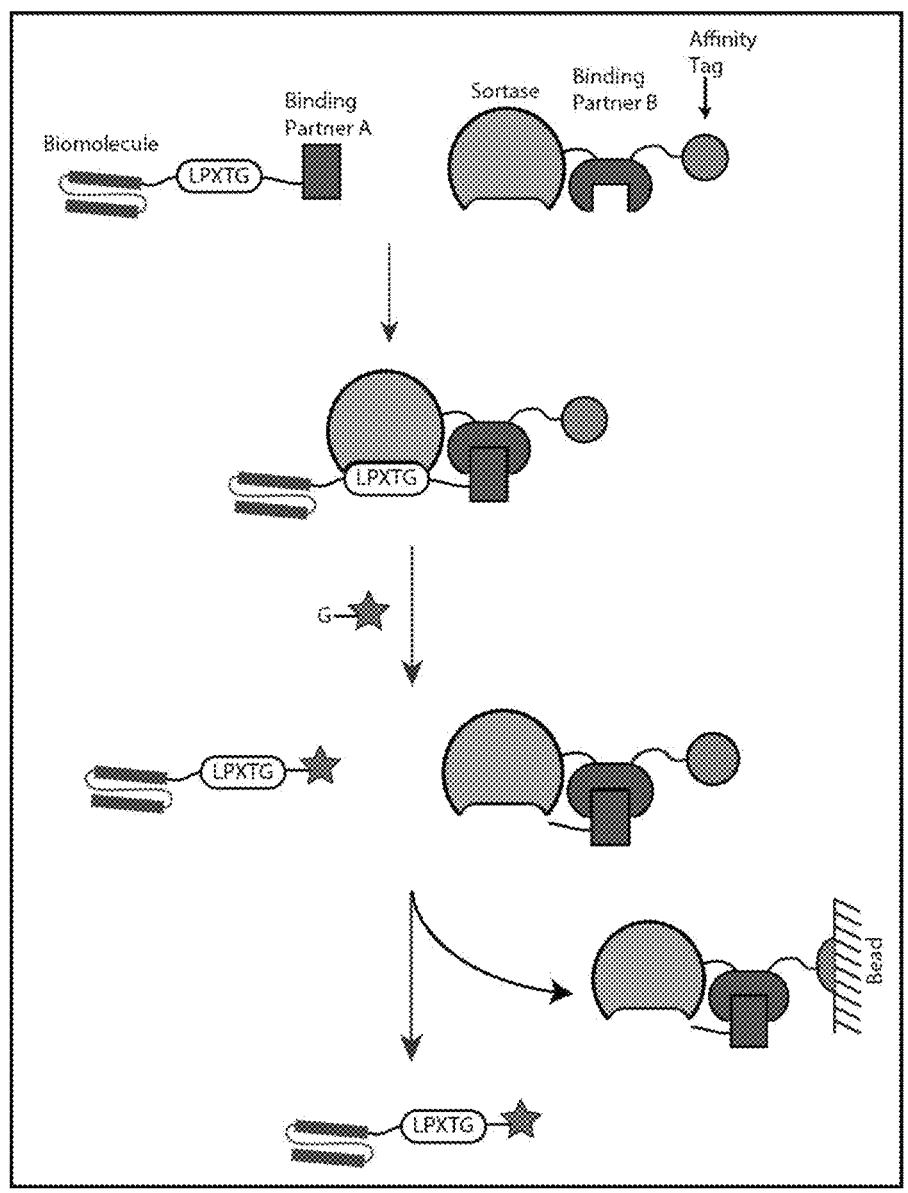
FIG. 4. Schematic of Proximity-Based Sortase Ligation in Solution Phase. A biomolecule of interest is expressed in frame with a sortase recognition motif and one member of a binding pair (Binding Partner A). In parallel, a sortase enzyme is expressed in frame with a second member of a binding pair (Binding Partner B) and an affinity tag. The biomolecule can be bound by the sortase construct, in solution, and ligated to any peptide/protein with an N-terminal glycine. If desired, the peptide/protein can be labeled with a chemical or biological moiety (e.g. imaging agent, drug, click chemistry group, hapten, oligonucleotide, etc.), indicated by the green star. The sortase construct can then be removed from the sample via an affinity column/beads.

In Example 10, to generate the construct for the sortase fusion protein, sortase (Srt) is cloned in frame and in series so that it is placed, with an intervening linker (e.g., a flexible GS-rich linker), N-terminal to binding partner B (BP-B), which, in turn, is N-terminal to an affinity tag, and the sortase fusion protein is expressed (FIG. 4—upper right).

Alternatively, in Example 11, to generate the construct for the capture fusion protein, sortase (Srt) is cloned in frame and in series so that it is placed, with an intervening linker (e.g., a flexible GS-rich linker), C-terminal to binding partner B (BP-B) and N-terminal to an affinity tag, and the sortase fusion protein is expressed.

In parallel, for the second protein construct, the coding sequence of a protein of interest is cloned in frame and in series a sortase recognition motif (e.g., LPXTG), and binding partner A (BP-A). The fusion protein comprising the protein of interest is then expressed (FIG. 4—upper left).

In the absence of the appropriate affinity resin, the fusion protein comprising the protein of interest is bound to the sortase fusion protein, in solution, through the interaction between binding partners A and B (FIG. 4—center). Adding both calcium and a peptide with an N-terminal glycine or polyglycine (e.g., GGG) (and attached cargo, if desired) allows sortase to simultaneously cleave the protein of interest from the binding partner complex and ligate the peptide onto the protein of interest (FIG. 4—center). If desired, the peptide/protein is labeled with a chemical or biological moiety (e.g. imaging agent, drug, click chemistry group, hapten, oligonucleotide, etc.) (indicated by the green star in FIG. 4—bottom). The peptide/protein of interest is subsequently purified by removal of the binding partner complex and sortase on an affinity resin (FIG. 4—bottom).

Examples 12 and 13: Proximity-Based Sortase Ligation of an Antibody: Combining Purification and Site-Specific Bioconjugation Using Binding Partners on Heavy Chains In these Examples, the proximity-based sortase method is applied to an antibody or to a moiety thereof. The reaction optionally takes place in the absence of an affinity resin.

In Example 12, to generate the construct for the capture fusion protein, sortase (Srt) is cloned in frame and in series so that it is placed, with an intervening linker (e.g., a flexible GS-rich linker), N-terminal to binding partner B (BP-B), which, in turn, is N-terminal to a first affinity tag (FIG. 5—upper right), and the capture fusion protein is expressed.

Alternatively, in Example 13, to generate the construct for the capture fusion protein, sortase (Srt) is cloned in frame and in series so that it is placed, with an intervening linker (e.g., a flexible GS-rich linker), C-terminal to binding partner B (BP-B) and N-terminal to a first affinity tag, and the capture fusion protein is expressed.

Figure 5:
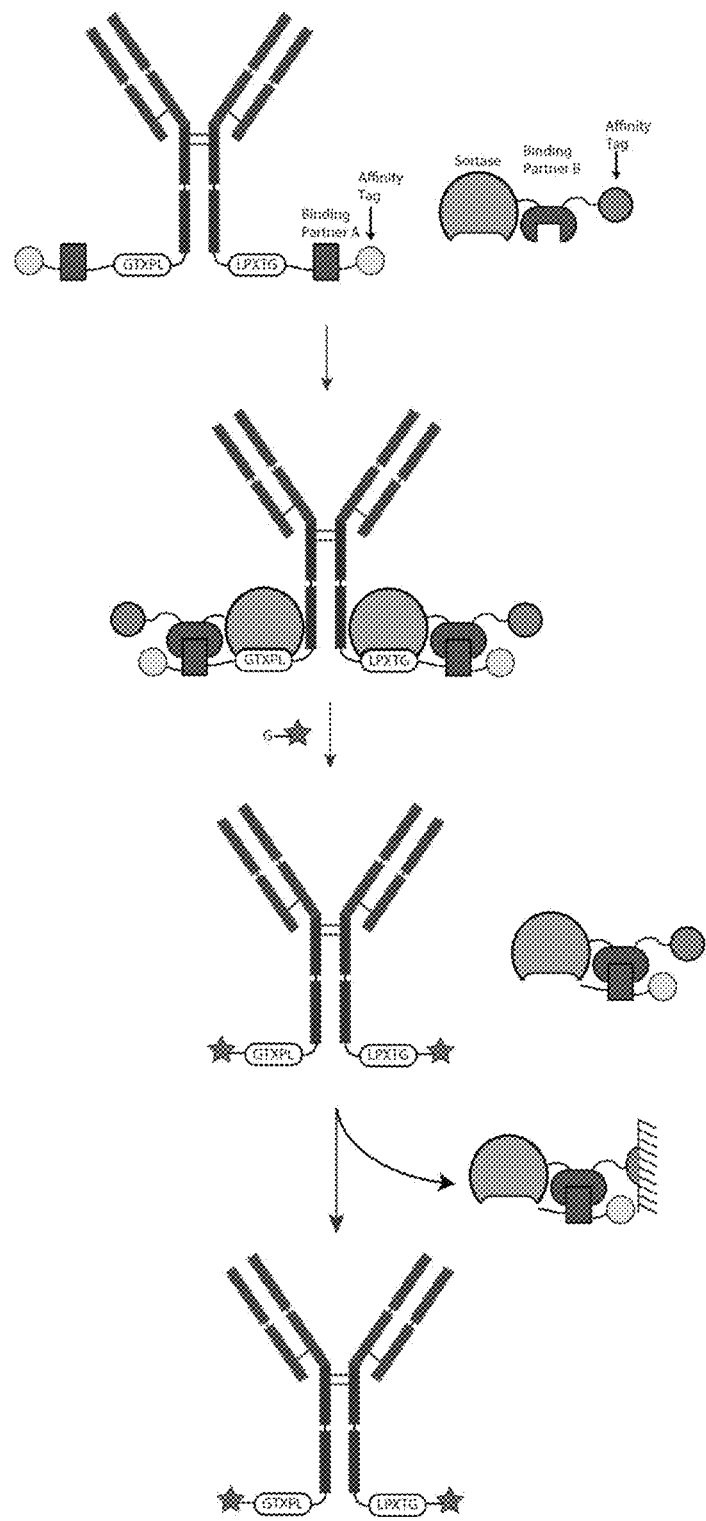
FIG. 5. Schematic of Proximity-Based Sortase Ligation of an Antibody. An antibody is expressed with a sortase recognition motif and one member of a binding pair (Binding Partner A) at the C-terminus of each heavy chain and/or each light chain, followed by a first affinity tag. In parallel, a sortase enzyme is expressed in frame with a second member of a binding pair (Binding Partner B) and a second affinity tag. The second affinity tag may be the same or different than the first affinity tag. The antibody can be bound by the sortase construct and ligated to any peptide/protein with an N-terminal glycine. If desired, the peptide/protein can be labeled with a chemical or biological moiety (e.g. imaging agent, drug, click chemistry group, hapten, oligonucleotide, etc.), indicated by the green star. The sortase construct can then be removed from the sample via an affinity column/beads.

In parallel, for the antibody-fusion construct, at the C-terminus of the heavy chain(s) of an antibody, there is a fusion protein in frame and in series comprising a sortase recognition motif (e.g., LPXTG), a binding partner A (BP-A), and a second affinity tag, which may be the same or different than the first affinity tag on the capture fusion protein (FIG. 5—upper left). Where there is a second unique affinity tag, the antibody may be optionally purified on the appropriate second affinity resin. Linkers can optionally be placed between the antibody and sortase recognition motif, between the sortase recognition motif and BP-A, and/or between BP-A and the second affinity tag. Alternatively, the fusion protein is linked to the C-terminus of a moiety of an antibody, such as an antigen-binding protein.

The antibody-fusion construct is bound to the capture fusion protein through the interaction between binding partners A and B (FIG. 5—center), optionally in solution. Adding both calcium and a peptide with an N-terminal glycine or polyglycine (e.g., GGG) (and attached cargo, if desired) allows sortase simultaneously to cleave the antibody from the binding partner complex and to ligate the peptide onto the C-terminus of the antibody (FIG. 5—center). If desired, the peptide/antibody is labeled with a chemical or biological moiety (e.g. imaging agent, drug, click chemistry group, hapten, oligonucleotide, etc.) (indicated by the green star in FIG. 5—bottom). The peptide/antibody is subsequently purified by isolation of the binding partner complex and sortase on an affinity resin (a first or second affinity resin corresponding, respectively to the first or second affinity tag) via one of the affinity tags.

Examples 14 and 15: Proximity-Based Sortase Ligation of an Antibody: Combining Purification and Site-Specific Bioconjugation Using Binding Partners on Light Chains In these Examples, the proximity-based sortase method is applied to an antibody or to a moiety thereof. The reaction optionally takes place in the absence of an affinity resin.

In Example 14, to generate the construct for the capture fusion protein, sortase (Srt) is cloned in frame and in series so that it is placed, with an intervening linker (e.g., a flexible GS-rich linker), N-terminal to binding partner B (BP-B), which, in turn, is N-terminal to a first affinity tag (see FIG. 5—upper right), and the capture fusion protein is expressed.

Alternatively, in Example 15, to generate the construct for the capture fusion protein, sortase (Srt) is cloned in frame and in series so that it is placed, with an intervening linker (e.g., a flexible GS-rich linker), C-terminal to binding partner B (BP-B) and N-terminal to a first affinity tag, and the capture fusion protein is expressed.

In these Examples (and similar to Examples 12 and 13), for the antibody-fusion construct, at the C-terminus of the light chain(s) of an antibody, there is a fusion protein in frame and in series comprising a sortase recognition motif (e.g., LPXTG), a binding partner A (BP-A), and a second affinity tag, which may be the same or different than the affinity tag on the capture fusion protein. Where there is a second affinity tag, the antibody may be optionally purified on the appropriate second affinity resin. Linkers can optionally be placed between the antibody and sortase recognition motif, between the sortase recognition motif and BP-A, and/or between BP-A and the second affinity tag. Alternatively, the fusion protein is linked to the C-terminus of a moiety of an antibody, such as an antigen-binding protein.

The antibody-fusion construct is bound to the capture fusion protein via the interaction between binding partners A and B, optionally in solution. Adding both calcium and a peptide with an N-terminal glycine or polyglycine (e.g., GGG) (and attached cargo, if desired) allows sortase simultaneously to cleave the antibody from the binding partner complex and to ligate the peptide onto the C-terminus of the antibody. If desired, the peptide/antibody is labeled with a chemical or biological moiety (e.g. imaging agent, drug, click chemistry group, hapten, oligonucleotide, etc.). The peptide/antibody is subsequently purified by isolating the binding partner complex and sortase on an affinity resin (a first or second affinity resin corresponding, respectively to the first or second affinity tag) via one of the affinity tags.

Examples 16 and 17: Proximity-Based Sortase Ligation of an Antibody: Combining Purification and Site-Specific Bioconjugation Using Binding Partners on Both Heavy Chains and Light Chains In these Examples, the proximity-based sortase method is applied to an antibody or to a moiety thereof. The reaction optionally takes place in the absence of an affinity resin.

In Example 16, to generate the construct for the capture fusion protein, sortase (Srt) is cloned in series so that it is placed, with an intervening linker (e.g., a flexible GS-rich linker), N-terminal to binding partner B (BP-B), which, in turn, is N-terminal to a first affinity tag (FIG. 6—middle right), and the capture fusion protein is expressed.

Alternatively, in Example 17, to generate the construct for the capture fusion protein, sortase (Srt) is cloned in series so that it is placed, with an intervening linker (e.g., a flexible GS-rich linker), C-terminal to binding partner B (BP-B) and N-terminal to a first affinity tag, and the capture fusion protein is expressed.

Figure 6:
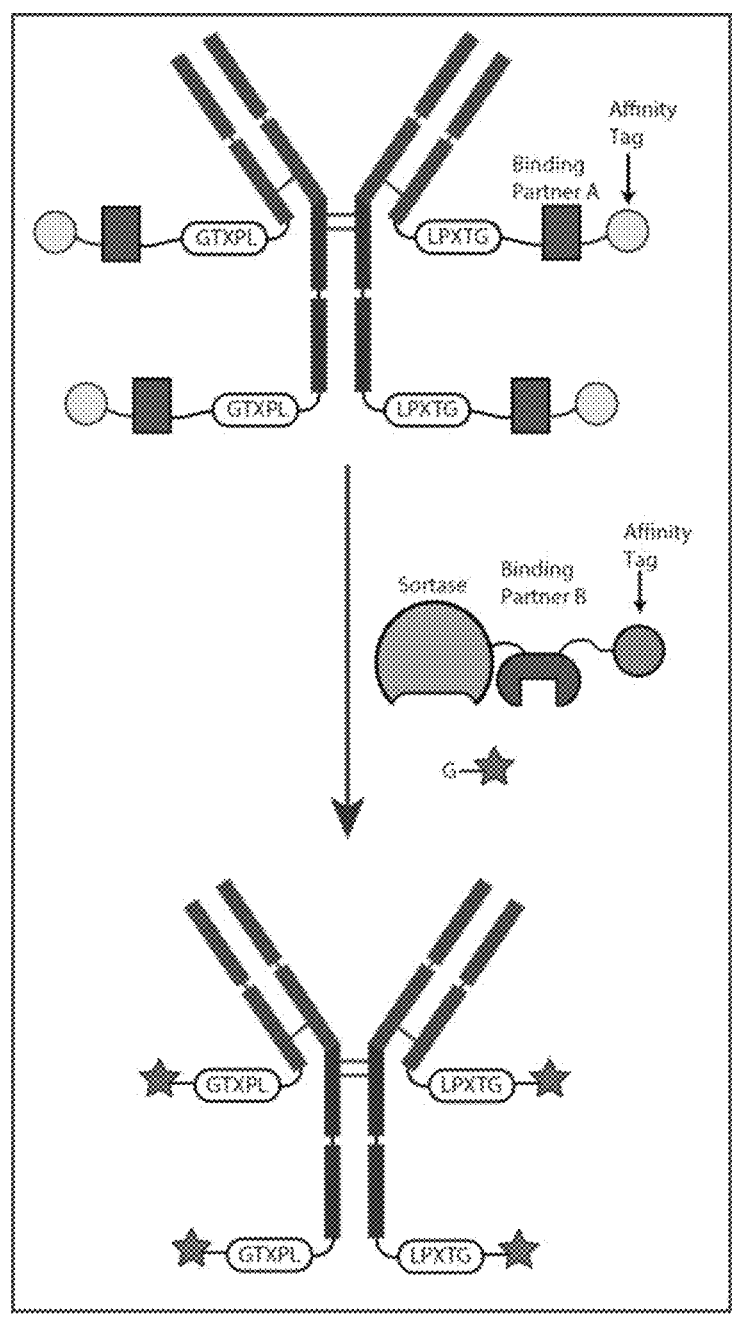
FIG. 6. Schematic of an Antibody Being Labeled with Four Compounds via Proximity-Based Sortase Ligation. (A) An antibody is expressed with a sortase recognition motif and one member of a binding pair (Binding Partner A) at the C-terminus of each heavy chain and each light chain, followed by a first affinity tag. In parallel, a sortase enzyme is expressed in frame with a second member of a binding pair (Binding Partner B) and a second affinity tag. The second affinity tag may be the same or different than the first affinity tag. The antibody can be bound by the sortase construct and ligated to any peptide/protein with an N-terminal glycine. If desired, the peptide/protein can be labeled with four chemical or biological moieties (e.g. imaging agent, drug, click chemistry group, hapten, oligonucleotide, etc.), indicated by the green star. The sortase construct can then be removed from the sample via an affinity column/beads.

In parallel, for the antibody-fusion construct, at the C-termini of both the heavy chain(s) and light chain(s) of an antibody, there is a fusion protein in series comprising a sortase recognition motif (e.g., LPXTG), a binding partner A (BP-A), and a second affinity tag, which may be the same or different than the first affinity tag on the capture fusion protein (FIG. 6—top). Where there is a second affinity tag, the antibody may be optionally purified on the appropriate second affinity resin. Linkers can optionally be placed between the antibody and sortase recognition motif, between the sortase recognition motif and BP-A, and/or between BP-A and the second affinity tag. Alternatively, the fusion protein is linked to the C-terminus of a moiety of an antibody, such as an antigen-binding protein.

The antibody-fusion construct is bound to the capture fusion protein through the interaction between binding partners A and B (FIG. 6—center), optionally in solution. Adding both calcium and a peptide with an N-terminal glycine or polyglycine (e.g., GGG) (and attached cargo, if desired) allows sortase simultaneously to cleave the antibody from the binding partner complex and to ligate the peptide onto the C-terminus of the antibody (FIG. 6—center). If desired, the peptide/antibody is labeled with a chemical or biological moiety (e.g. imaging agent, drug, click chemistry group, hapten, oligonucleotide, etc.) (indicated by the green star in FIG. 6—bottom). The peptide/antibody is subsequently purified by isolation of the binding partner complex and sortase on an affinity resin (a first or second affinity resin corresponding, respectively to the first or second affinity tag) via one of the affinity tags.

Examples 18-20: Proximity-Based Sortase Ligation of an Antibody: Combining Purification and Site-Specific Bioconjugation Using Different Binding Partners with Unique Specificities on Both Heavy Chains and Light Chains In these Examples, the proximity-based sortase method is applied to an antibody or to a moiety thereof. The reaction optionally takes place in the absence of an affinity resin. In these Examples, heavy chains and light chains are labeled with two different chemical/biological moieties, respectively, where two binding pairs with unique specificities, and two sortases with optionally distinct specificities, are used.

Figure 7:
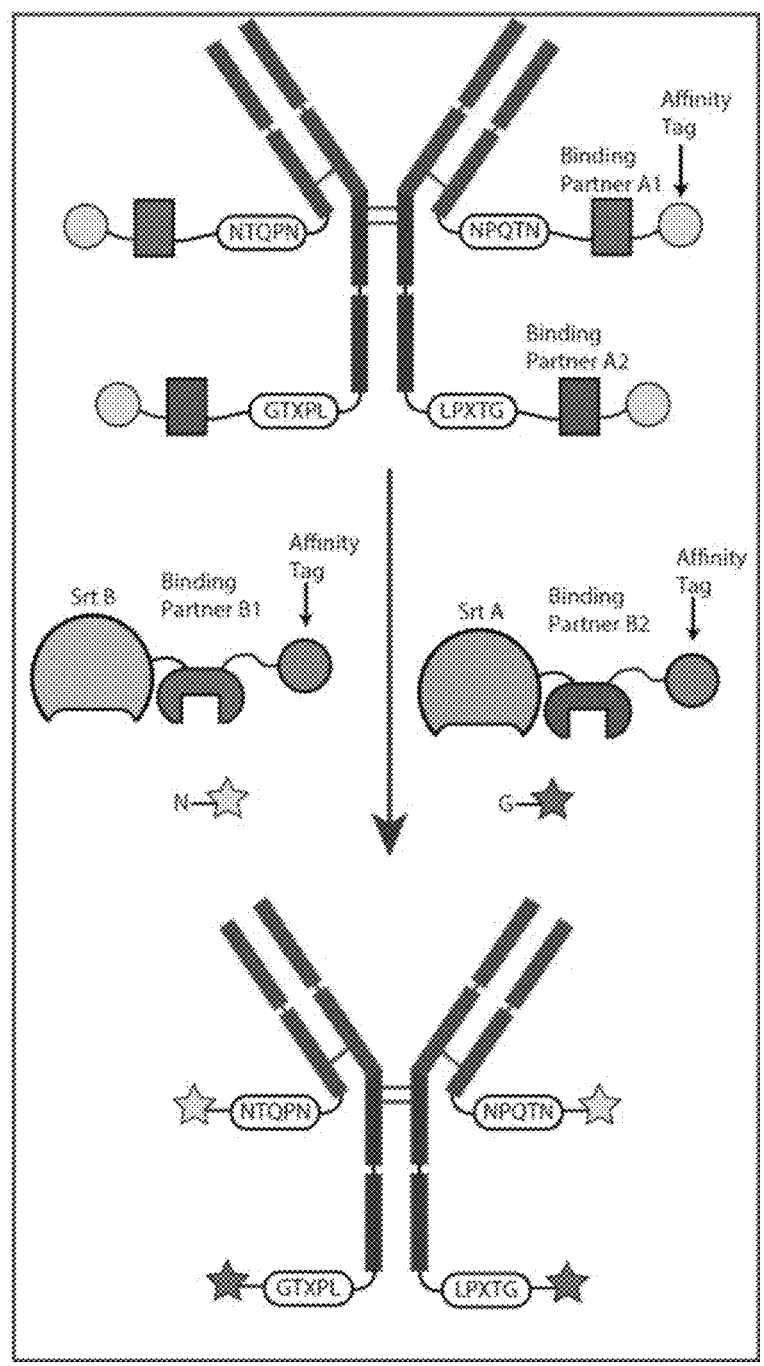
FIG. 7. Schematic of an Antibody Being Labeled with Four Compounds via Proximity-Based Sortase Ligation: Labeling with Two Different Compounds. An antibody is expressed with a first sortase recognition motif (e.g., NPQTN) and one member of a first binding pair (Binding Partner A1) at the C-terminus of each light chain. In tandem, an antibody is expressed with a second sortase recognition motif (e.g., LPXTG) and one member of a second binding pair (Binding Partner A2), which is distinct from the first binding pair and which does not cross-react with the first binding pair, at the C-terminus of each heavy chain. In parallel, a first sortase enzyme is expressed in in frame with a second member of a first binding pair (Binding Partner B1) and an affinity tag, and a second sortase enzyme is expressed in in frame with a second member of a second binding pair (Binding Partner B2). Therefore, the heavy chains and light chains are labeled with two different chemical/biological moieties, respectively, using two binding pairs and two sortases, with unique specificities. The antibody can be bound by the two distinct sortase constructs, each of which can be specifically, and therefore independently, ligated to any peptide/protein with an N-terminal glycine. If desired, the peptide/protein can be labeled with four chemical or biological moieties (e.g. imaging agent, drug, click chemistry group, hapten, oligonucleotide, etc.) of two distinct types, indicated by the green stars and the yellow stars. The first and second sortase constructs can then be removed independently from the sample via an affinity column/beads. Note, it is possible to achieve unique labeling of the light and heavy chains using the same sortase, if unique binding pairs are used and if labeling of the light and heavy chains is done sequentially.

In Example 18, to generate a first construct encoding a first capture fusion protein, sortase (Srt) is cloned in frame and in series so that it is placed, with an intervening linker (e.g., a flexible GS-rich linker), N-terminal to binding partner B1 (BP-B1), which, in turn, is N-terminal to a first affinity tag (FIG. 7—middle left), and a first capture fusion protein is expressed. The process is repeated to generate a second construct encoding a second capture fusion protein in which sortase (Srt) is cloned in frame and in series so that it is placed, with an intervening linker (e.g., a flexible GS-rich linker), N-terminal to binding partner B2 (BP-B2), which, in turn, is N-terminal to a second affinity tag optionally distinct from the first affinity tag (FIG. 7—middle right), and a second capture fusion protein is expressed, having a specificity distinct from that of the first capture fusion protein, in order to provide two capture fusion proteins, each with a distinct specificity (FIG. 7—middle right and left). In some embodiments, the affinity tag on the first capture fusion protein is distinct from the affinity tag on the second capture fusion protein, although this is optional.

Alternatively, in Example 19, to generate a first construct for a first capture fusion protein, sortase (Srt) is cloned in frame and in series so that it is placed, with an intervening linker (e.g., a flexible GS-rich linker), C-terminal to binding partner B1 (BP-B1) and N-terminal to a first affinity tag, and a first capture fusion protein is expressed. The process is repeated to generate a second construct for a second capture fusion protein in which sortase (Srt) is cloned in frame and in series so that it is placed, with an intervening linker (e.g., a flexible GS-rich linker), C-terminal to binding partner B2 (BP-B2) and N-terminal to a second affinity tag optionally distinct from the first affinity tag, and a second capture fusion protein is expressed, having a specificity distinct from that of the first capture fusion protein, in order to provide two capture fusion proteins, each with a distinct specificity. In some embodiments, the affinity tag on the first capture fusion protein is distinct from the affinity tag on the second capture fusion protein, although this is optional.

Alternatively, in Example 20, to generate a first construct encoding a first capture fusion protein, sortase (Srt) is cloned in frame and in series so that it is placed, with an intervening linker (e.g., a flexible GS-rich linker), N-terminal to binding partner B1 (BP-B1), which, in turn, is N-terminal to a first affinity tag (FIG. 7—middle left), and a first capture fusion protein is expressed. In contrast, to generate a second construct for a second capture fusion protein, sortase (Srt) is cloned in frame and in series so that it is placed, with an intervening linker (e.g., a flexible GS-rich linker), C-terminal to binding partner B2 (BP-B2) and N-terminal to a second affinity tag optionally distinct from the first affinity tag, and a second capture fusion protein is expressed, having a specificity distinct from that of the first capture fusion protein, in order to provide two differently ordered capture fusion proteins, each with a distinct specificity. In some embodiments, the affinity tag on the first capture fusion protein is distinct from the affinity tag on the second capture fusion protein, although this is optional.

In parallel, for the antibody-fusion construct, at the C-terminus of the light chain(s), there is a first antibody fusion protein in series comprising a sortase recognition motif (e.g., LPXTG), binding partner A1 (BP-A1), and a third affinity tag, which is optionally distinct from any affinity tag on the capture fusion protein (FIG. 7—top right). Where there is a third affinity tag, the antibody may be optionally purified on the appropriate third affinity resin. Alternatively, the first antibody fusion protein is linked to the C-terminus of a moiety of an antibody, such as an antigen-binding protein. Additionally, at the C-terminus of the heavy chain(s), there is a second antibody fusion protein in series comprising a second sortase recognition motif (e.g., NPQTN) optionally distinct from the first sortase recognition motif, binding partner A2 (BP-A2), and optionally yet another linker and a fourth affinity tag, which is optionally distinct from any affinity tag on the capture fusion protein and which is optionally distinct from the third affinity tag on the first antibody fusion protein (FIG. 7—top right). Where there is a fourth affinity tag, the antibody may be optionally purified on the appropriate fourth affinity resin. Alternatively, the second antibody fusion protein is linked to the C-terminus of a moiety of an antibody, such as an antigen-binding protein. In some embodiments, the affinity tag on the first antibody fusion protein is distinct from the affinity tag on the second antibody fusion protein, although this is optional.

In some embodiments, each affinity tag (i.e., on the first capture fusion protein, on the second capture fusion protein, on the first antibody fusion protein, and on the second antibody fusion protein) is distinct and corresponds to a distinct affinity resin.

The first antibody-fusion construct is bound to the first sortase fusion protein through the interaction between binding partners A1 and B1, while the second antibody-fusion construct is bound to the second sortase fusion protein through the interaction between binding partners A2 and B2, optionally in solution. In each situation, adding both calcium and a peptide with an N-terminal glycine or polyglycine (e.g., GGG) (and attached cargo, if desired) allows sortase simultaneously to cleave the antibody from the corresponding binding partner complex and to ligate the corresponding peptide onto the C-terminus of the antibody. If desired, the peptide/antibody is labeled with a chemical or biological moiety (e.g. imaging agent, drug, click chemistry group, hapten, oligonucleotide, etc.) (indicated by the green and yellow stars in FIG. 7—bottom) with labeling optionally distinct for each reaction. The antibody is subsequently purified by isolation of the binding partner complex and sortase on an appropriate affinity resin via one or more of the affinity tags (FIG. 7—bottom).

Alternatively, the first antibody-fusion construct is bound to the first sortase fusion protein through the interaction between binding partners A1 and B1. Adding calcium and a peptide with an N-terminal glycine or polyglycine (e.g., GGG) (and attached cargo, if desired) allows sortase to cleave the antibody from the corresponding binding partner complex and to ligate the corresponding peptide onto the antibody C-terminus. If desired, the peptide/antibody can be labeled with a chemical or biological moiety (e.g., imaging agent, drug, click chemistry group, hapten, oligonucleotide, etc.) (indicated by the green and yellow stars in FIG. 7—bottom). The first binding partner complex and sortase is then removed via an appropriate affinity resin. The second antibody-fusion construct is then bound to the second sortase fusion protein through the interaction between binding partners A2 and B2, optionally in solution. Adding calcium and a peptide with an N-terminal glycine or polyglycine (e.g., GGG) (and attached cargo, if desired) allows sortase to cleave the antibody from the corresponding binding partner complex and to ligate the corresponding peptide onto the C-terminus of the antibody. If desired, the peptide/antibody is labeled with a chemical or biological moiety (e.g., imaging agent, drug, click chemistry group, hapten, oligonucleotide, etc.) (indicated by the green and yellow stars in FIG. 7—bottom). The chemical or biological moiety can be optionally distinct for each reaction. The antibody is subsequently purified by isolation of the binding partner complex and sortase on an appropriate affinity resin via one or more of the affinity tags (FIG. 7—bottom).

In some embodiments, the antibody chains, or portions thereof, may be separated or cleaved, and then the chains or portions may be isolated separately on one or more appropriate affinity resins via one or more of the affinity tags.

Examples 21 and 22: Proximity-Based Sortase Ligation of an Antibody or a Protein: Antibody or Protein Purification and Separation from Unlabeled or Incompletely Labeled Antibodies or Proteins In these Examples, the proximity-based sortase method is applied to an antibody or to a moiety thereof. The reaction optionally takes place in the absence of an affinity resin.

In Example 21, to generate the construct for the capture fusion protein, sortase (Srt) is cloned in frame and in series so that it is placed, with an intervening linker (e.g., a flexible GS-rich linker), N-terminal to binding partner B (BP-B), which, in turn, is N-terminal to a first affinity tag (FIG. 8—top right), and the capture fusion protein is expressed.

Alternatively, in Example 22, to generate the construct for the capture fusion protein, sortase (Srt) is cloned in frame and in series so that it is placed, with an intervening linker (e.g., a flexible GS-rich linker), C-terminal to binding partner B (BP-B) and N-terminal to a first affinity tag, and the capture fusion protein is expressed.

Figure 8:
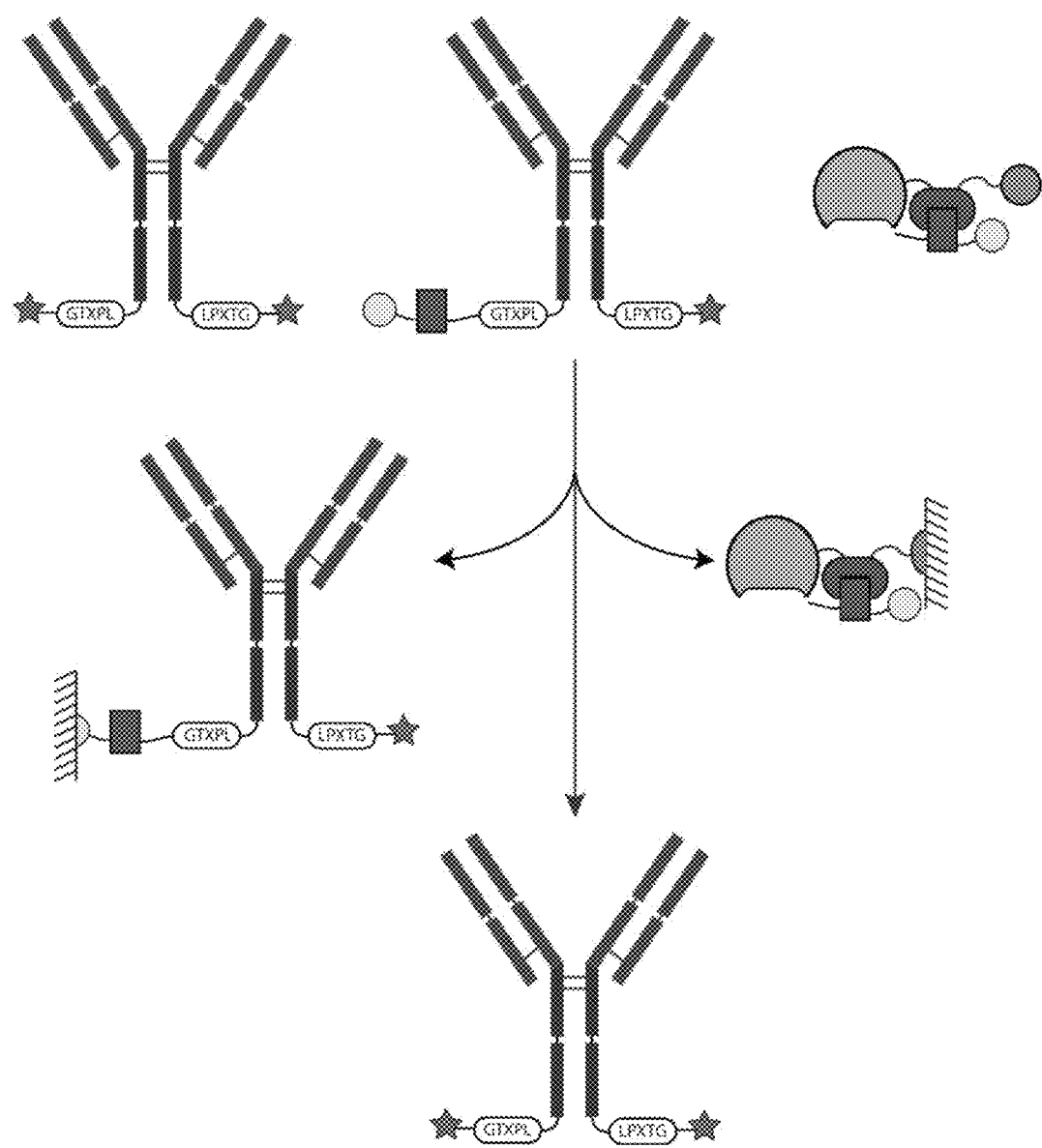
FIG. 8. Schematic of Antibody Purification Following Proximity-Based Sortase Ligation. Following labeling of antibodies via proximity-based sortase ligation, the sortase enzyme and antibodies that have not been completely labeled can be removed via affinity purification. An analogous method can be used to remove unlabeled or incompletely labeled proteins.

In these Examples, for the antibody-fusion construct, at the C-terminus of the heavy chain(s) and/or at the C-terminus of the light chain(s) of an antibody, there is a fusion protein in frame and in series comprising a sortase recognition motif (e.g., LPXTG), a binding partner A (BP-A), and a second affinity tag, which may be the same or distinct from the first affinity tag on the capture fusion protein (FIG. 8—top center). Alternatively, the fusion protein is linked to the C-terminus of a moiety of an antibody, such as an antigen-binding protein.

In some embodiments, there may be more than one capture fusion protein and/or more than one antibody fusion protein (e.g., using distinct binding partner pairs; see, e.g., Examples 18-20), and/or the affinity tags of each type of fusion protein may be distinct and specific for distinct affinity tags.

The antibody-fusion protein is bound to the sortase fusion protein through the interaction between binding partners A and B, optionally in solution. Adding both calcium and a peptide with an N-terminal glycine or polyglycine (e.g., GGG) (and attached cargo, if desired) allows sortase to simultaneously cleave the antibody from the binding partner complex and ligate the peptide onto the C-terminus of the antibody (FIG. 8—top left and top right). If desired, the peptide/antibody is labeled with a chemical or biological moiety (e.g. imaging agent, drug, click chemistry group, hapten, oligonucleotide, etc.) (indicated by the green stars in FIG. 8) with labeling optionally distinct for each reaction. The antibody is subsequently purified by isolation of the binding partner complex and sortase on an appropriate affinity resin via one or more of the affinity tags (FIG. 8—bottom).

However, in some situations, where there is incomplete labeling of the antibodies (e.g., due to a non-stoichiometric amount of a reagent or to an incomplete, inefficient, or partially inhibited reaction), it may be desirable to separate and remove unlabeled or incompletely labeled antibodies (FIG. 8—top center).

The unlabeled or incompletely labeled antibody is subsequently purified by isolation of the binding partner complex and sortase on a second affinity resin corresponding to the second affinity tag, which is attached to at least one chain or moiety of the antibody. Fully labeled antibody is subsequently purified by a combination of (1) isolation of the binding partner complex and sortase on an appropriate first affinity resin via the first affinity tag (FIG. 8—middle right), (2) isolation of the unlabeled or incompletely labeled antibody on the second affinity resin via the second affinity tag (FIG. 8—middle left), and (3) removal of the fully labeled antibody (FIG. 8—bottom).

Similarly, these methods are used to remove unlabeled or incompletely labeled proteins.

Examples 23 and 24: Proximity-Based Sortase Ligation of a Protein: Protein Purification and Separation from Unlabeled Proteins In these Examples, the proximity-based sortase method is applied to an antibody or to a moiety thereof. The reaction optionally takes place in the absence of an affinity resin.

In Example 23, to generate the construct for the capture fusion protein, sortase (Srt) is cloned in frame and in series so that it is placed, with an intervening linker (e.g., a flexible GS-rich linker), N-terminal to binding partner B (BP-B), which, in turn, is N-terminal to a first affinity tag, and the capture fusion protein is expressed.

Alternatively, in Example 24, to generate the construct for the capture fusion protein, sortase (Srt) is cloned in frame and in series so that it is placed, with an intervening linker (e.g., a flexible GS-rich linker), C-terminal to binding partner B (BP-B) and N-terminal to a first affinity tag, and the capture fusion protein is expressed.

In these Examples, for the second protein construct, the coding sequence of a protein of interest is cloned in frame and in series with a sortase recognition motif (e.g., LPXTG), a binding partner A (BP-A), as well as a second affinity tag, which may be the same or distinct from the first affinity tag on the capture fusion protein. The fusion protein comprising the protein of interest is then expressed.

The fusion protein comprising the protein of interest is bound to the sortase capture fusion protein through the interaction between binding partners A and B, optionally in solution. Adding both calcium and a peptide with an N-terminal glycine or polyglycine (e.g., GGG) (and attached cargo, if desired) allows sortase to simultaneously cleave the protein of interest from the binding partner complex and ligate the peptide onto the protein of interest. If desired, the peptide/protein is labeled with a chemical or biological moiety (e.g., imaging agent, drug, click chemistry group, hapten, oligonucleotide, etc.). Subsequently, the peptide/protein of interest is purified by removal of the binding partner complex and sortase on an affinity resin.

However, in some situations, where there is incomplete labeling of the protein of interest constructs (e.g., due to a non-stoichiometric amount of a reagent or to an incomplete, inefficient, or partially inhibited reaction), it may be desirable to separate and remove unlabeled or incompletely labeled constructs.

The unlabeled or incompletely labeled construct is subsequently purified by isolation of the binding partner complex and sortase on a second affinity resin corresponding to the second affinity tag, which is attached to at least one chain or moiety of the antibody. Fully labeled peptide/protein product is subsequently purified by a combination of (1) isolation of the binding partner complex and sortase on an appropriate first affinity resin via the first affinity tag, (2) isolation of the unlabeled or incompletely labeled constructs on the second affinity resin via the second affinity tag, and (3) removal of the fully labeled peptide/protein product.

Example 25: Proximity-Based Sortase-Tag Expressed Protein Ligation (STEPL): Purification of Enhanced Green Fluorescent Protein (eGFP)

A valuable feature of the proximity-based sortase ligation system is that it allows for site-specific labeling of recombinantly expressed proteins without requiring steps in addition to what is normally required for protein purification. Under optimal conditions, all of the recombinant protein that is released from the affinity column would be labeled with the desired cargo as a result of the SrtA-mediated ligation reaction. To evaluate the efficiency of this proximity-based sortase ligation reaction and to assess the extent of any non-specific cleavage of the LPXTG motif, in the absence of ligation, a model system was designed with Enhanced Green Fluorescent Protein (eGFP or EGFP) as the "ligand" (EGFP-STEPL). This allowed for quantitative monitoring of protein release from the affinity column in the presence and absence of triglycine and calcium. Notably, peptides with two or more glycines are typically preferred for SrtA-mediated ligations since they exhibit significantly improved binding and catalysis.

The SpyCatcher/SpyTag binding partner pair was chosen because following SpyTag-SpyCatcher binding, SpyCatcher forms an isopeptide bond with SpyTag, resulting in a covalent linkage between the pair.

This Example followed the protocols of Examples 1 and 3. A vector construct was made encoding a capture fusion protein comprising, in series, Sortase A (SrtA) from *Staphylococcus aureus*, a linker ([GGS]5), SpyCatcher (binding partner protein B), and a His tag (affinity tag), and the capture fusion protein was expressed. A second vector was made encoding a fusion protein comprising, in series, eGFP, a linker ([GGS]2), the LPETG sortase recognition motif, a second linker ([GGS]5) and SpyTag (binding partner A), and the fusion protein was expressed.

Clarified lysate containing eGFP-LPETG-SpyTag was incubated with SortaseA-SpyCatcher-His bound to nickel resin at room temperature for 30 minutes. SpyTag-SpyCatcher isopeptide bond formation results in the formation of a new approximately 60 kDa protein species. Following capture, each resin was washed with 3 column volumes of phosphate-buffered saline (PBS). The sortase reaction was initiated by incubating the resin with PBS containing 50 μM $CaCl_2$) and 2 mM triglycine at 37° C. for 2 hours, resulting in cleavage of the sortase motif and ligation of eGFP to the triglycine peptide to obtain the final approximately 30 kDa eGFP-LPETGGG product.

Figure 9:
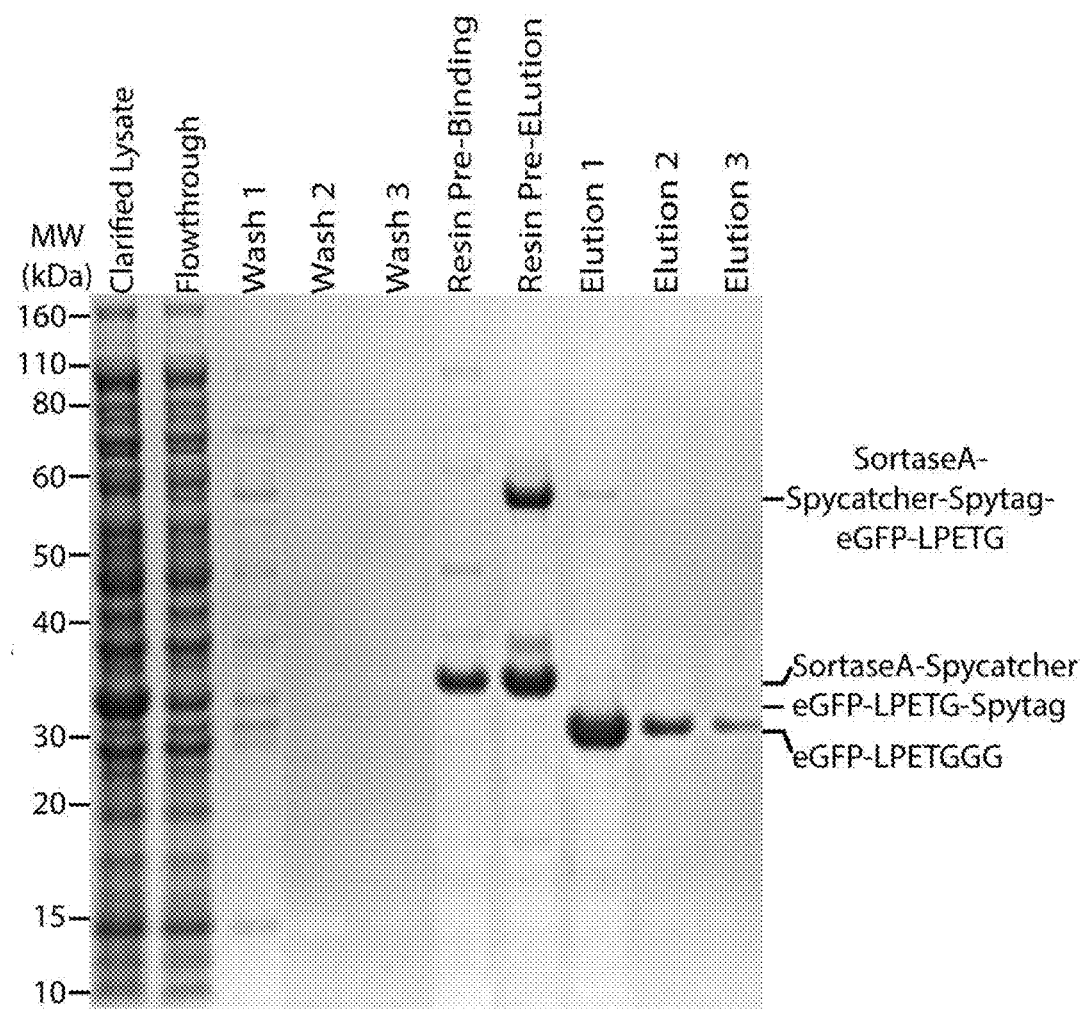
FIG. 9. Proximity-based Sortase Ligation Purification of eGFP Sortase-Spycatcher-His. Purification of eGFP-LPETGGG with Sortase-Spycatcher-His resin analyzed by Coomasie staining. Clarified lysate containing eGFP-LPETG-SpyTag was incubated with the indicated fusion capture protein bound to nickel resin at room temperature for 30 minutes. SpyTag-SpyCatcher isopeptide bond formation results in the formation of a new approximately 60 kDa protein species. Following capture the resin was washed with 3 column volumes of phosphate buffered saline (PBS) containing 50 µM $CaCl_2$ and 2 mM triglycine at 37° C. for 2 hours, resulting in cleavage of the sortase motif and ligation of eGFP to the triglycine peptide to obtain the final approximately 30 kDa eGFP-LPETGGG product.

The results (FIG. 9) were analyzed by protein acrylamide gel electrophoresis (PAGE) with Coomasie staining. A band corresponding to the SortaseA-SpyCatcher-His bound to nickel resin (FIG. 9) is clearly visible in the respective "Resin Pre-Capture" lanes, as well as being visible in the "Resin Pre-Elution" lane (FIG. 9). Also visible in the "Resin Pre-Elution" lane (FIG. 9) is the approximately 60 kDa band corresponding to the captured "SortaseA-SpyCatcher-SpyTag-eGFP-LPETG" complex. A band corresponding to the approximately 30 kDa final product "eGFP-LPETGGG" was eluted in the lanes corresponding to the three consecutive PBS elutions (the "Elution 1," "Elution 2," and "Elution 3" lanes), decreasing in amount with each elution (FIG. 9).

These findings demonstrate that the capture fusion protein (linked to binding pair partner B) on the affinity resin (FIG. 9: "Resin Pre-Binding") captured the fusion protein with the protein of interest (linked to binding pair partner A) (FIG. 9: "Resin Pre-Elution") and that following sortase cleavage and elution, the final product having the protein of interest linked to the sortase recognition site was eluted (FIG. 9: "Elution 1," "Elution 2," and "Elution 3").

Following capture and isopeptide bond formation between eGFP-LPETG-SpyTag and SortaseA-SpyCatcher-His, the final eGFP-LPETGGG product was obtained with greater than 80% yield and greater than 95% peptide ligation efficiency with a 2-hour 37° C. sortase reaction (FIG. 9). Yields for SortaseA-SpyCatcher-His were typically 50-60 mg/L, and 5-6 mg of fusion protein could be bound to 1 mL of nickel resin. Nickel resin containing either protein remained stable for at least 2 months when stored at 4° C.

Example 26: Proximity-Based Sortase-Tag Expressed Protein Ligation (STEPL): Purification of Enhanced Green Fluorescent Protein (eGFP)

Enhanced Green Fluorescent Protein (eGFP) was purified to characterize and demonstrate the utility of proximity-based sortase ligation. The SpyCatcher/SpyTag binding partner pair was chosen because following SpyTag-SpyCatcher binding, SpyCatcher forms an isopeptide bond with SpyTag, resulting in a covalent linkage between the pair.

This Example followed the protocols of Examples 1 and 2. A vector construct was made encoding a capture fusion protein comprising, in series, SpyCatcher (binding partner protein B), a linker ([(GGS)2-SGGGS-(GGS)4), Sortase A (SrtA) from *Staphylococcus aureus*, and a His tag (affinity tag), and the capture fusion protein was expressed. A second vector was made encoding a fusion protein comprising, in series, eGFP, a linker ([GGS]2) the LPETG sortase recognition motif, a second linker ([GGS]5), and SpyTag (binding partner A), and the fusion protein was expressed.

Clarified lysate containing eGFP-LPETG-SpyTag was incubated with SpyCatcher-SortaseA-His bound to nickel resin at room temperature for 30 minutes. SpyTag-SpyCatcher isopeptide bond formation results in the formation of a new approximately 60 kDa protein species. Following capture, each resin was washed with 3 column volumes of phosphate-buffered saline (PBS). The sortase reaction was initiated by incubating the resin with PBS containing 50 µM CaCl2 and 2 mM triglycine at 37° C. for 2 hours, resulting in cleavage of the sortase motif and ligation of eGFP to the triglycine peptide to obtain the final approximately 30 kDa eGFP-LPETGGG product.

Figure 10:
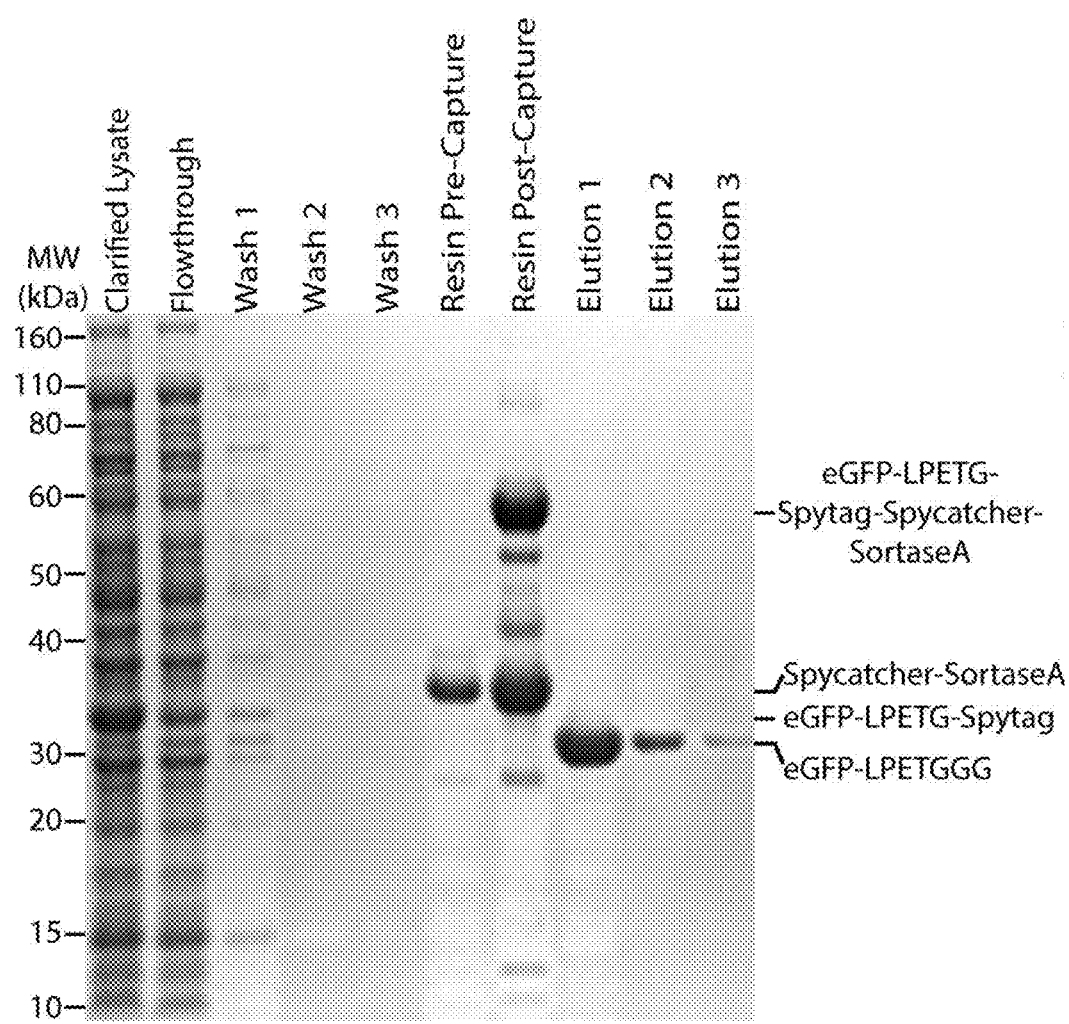
FIG. 10. Proximity-based Sortase Ligation Purification of eGFP with SpyCatcher-Sortase-His. Purification of eGFP-LPETGGG with SpyCatcher-Sortase-His resin analyzed by Coomasie staining. Clarified lysate containing eGFP-LPETG-SpyTag was incubated with the indicated fusion capture protein bound to nickel resin at room temperature for 30 minutes. SpyTag-SpyCatcher isopeptide bond formation results in the formation of a new approximately 60 kDa protein species. Following capture the resin was washed with 3 column volumes of phosphate buffered saline (PBS) containing 50 µM $CaCl_2$ and 2 mM triglycine at 37° C. for 2 hours, resulting in cleavage of the sortase motif and ligation of eGFP to the triglycine peptide to obtain the final approximately 30 kDa eGFP-LPETGGG product.

The results (FIG. 10) were analyzed by protein acrylamide gel electrophoresis (PAGE) with Coomasie staining. Bands corresponding to the SpyCatcher-SortaseA-His bound to nickel resin (FIG. 10) are clearly visible in the respective "Resin Pre-Capture" lanes, as well as being visible in the "Resin Post-Capture" lane (FIG. 10). Also visible in the "Resin Post-Capture" lane (FIG. 10) is the approximately 60 kDa capture band corresponding to the captured "eGFP-LPETG-SpyTag-SpyCatcher-SortaseA" complex. A band corresponding to the approximately 30 kDa final product "eGFP-LPETGGG" was eluted in the lanes corresponding to the three consecutive PBS elutions (the "Elution 1," "Elution 2," and "Elution 3" lanes), decreasing in amount with each elution (FIG. 10).

These findings show that the capture fusion protein (linked to binding pair partner B) on the affinity resin (FIG. 10: "Resin Pre-Binding") captured the fusion protein with the protein of interest (linked to binding pair partner A) (FIG. 10: "Resin Post-Capture") and that following sortase cleavage and elution, the final product with the protein of interest linked to the sortase recognition site was eluted (FIG. 10: "Elution 1," "Elution 2," and "Elution 3").

Following capture and isopeptide bond formation between eGFP-LPETG-SpyTag and SpyCatcher-SortaseA-His, the final eGFP-LPETGGG product was obtained with greater than 80% yield and greater than 95% peptide ligation efficiency with a 2-hour 37° C. sortase reaction (FIG. 10). Yields for SpyCatcher-SortaseA-His were typically 50-60 mg/L, and 5-6 mg of fusion protein could be bound to 1 mL of nickel resin. Nickel resin containing either protein remained stable for at least 2 months when stored at 4° C.

Example 27: Proximity-Based Sortase Ligation Capture Over Time

Figure 11:
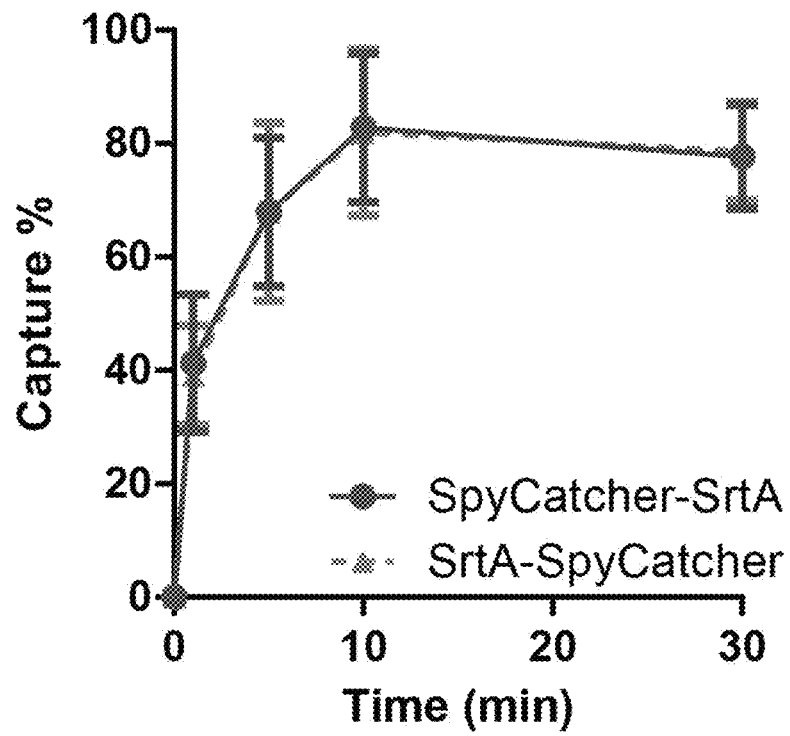
FIG. 11. Proximity-based Sortase Ligation capture over time. 10 µM eGFP-LPETG-SpyTag clarified lysates were incubated with 4 molar equivalents of either SpyCatcher-SrtA-His or SrtA-SpyCatcher-His resin at room temperature for indicated amounts of time. Following capture, the resin was washed with phosphate buffered saline (PBS) and the resin was stripped with PBS+200 mM imidazole to determine the amount of captured of eGFP-LPETG-SpyTag. eGFP concentrations were determined by measuring the absorbance at 488 nm ($\varepsilon$=56,000 $M^{-1}$ $cm^{-1}$). Both resins reached their maximum capture efficiency of ~80% by 10 minutes.

10 µM eGFP-LPETG-SpyTag clarified lysates were incubated with 4 molar equivalents of either SpyCatcher-SrtA-His or SrtA-SpyCatcher-His resin at room temperature for indicated amounts of time. Following capture, the resin was washed with phosphate buffered saline (PBS) and the resin was stripped with PBS+200 mM imidazole to determine the amount of captured of eGFP-LPETG-SpyTag. eGFP concentrations were determined by measuring the absorbance at 488 nm ($\varepsilon=56,000$ $M^{-1}$ $cm^{-1}$). Both resins reached their maximum capture efficiency of ~80% by 10 minutes, as shown in FIG. 11.

Figure 12:
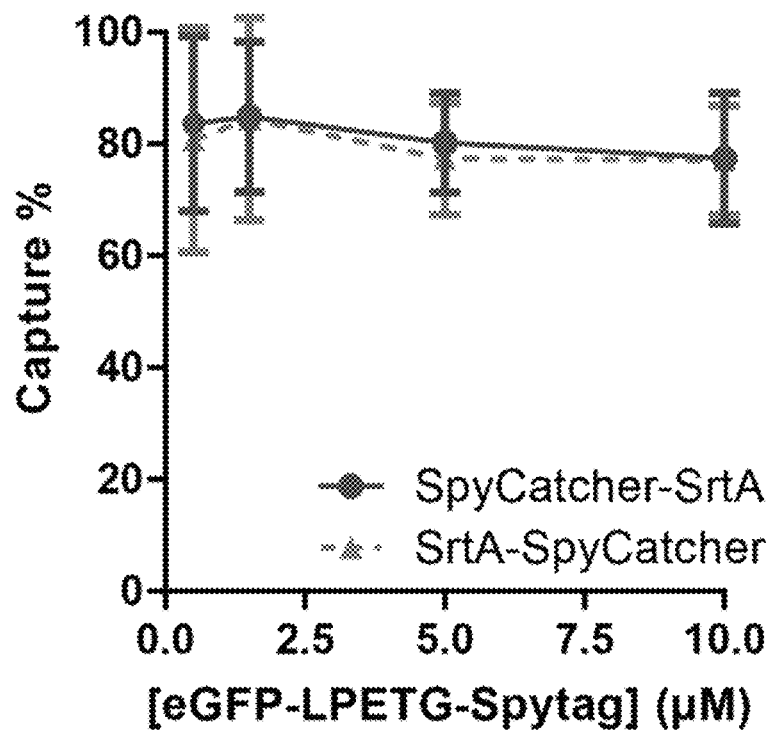
FIG. 12. Proximity-based Sortase Ligation capture with varying concentrations. Indicated concentrations of eGFP-LPETG-SpyTag clarified lysates were incubated with 4 molar equivalents relative to 10 µM eGFP-LPETG-SpyTag of either SpyCatcher-SrtA-His or SrtA-SpyCatcher-His resin at room temperature for 30 minutes. Following capture, the resin was washed with phosphate buffered saline (PBS) and the resin was stripped with PBS+200 mM imidazole to determine the amount of captured of eGFP-LPETG-SpyTag. eGFP concentrations were determined by measuring the absorbance at 488 nm ($\varepsilon$=56,000 $M^{-1}$ $cm^{-1}$). Both resins retained their maximum capture efficiency of ~80% when their target protein concentration was as low as 0.5 µM.

Example 28: Proximity-Based Sortase Ligation Capture with Varying Concentrations Indicated concentrations of eGFP-LPETG-SpyTag clarified lysates were incubated with 4 molar equivalents relative to 10 µM eGFP-LPETG-SpyTag of either SpyCatcher-SrtA-His or SrtA-SpyCatcher-His resin at room temperature for 30 minutes. Following capture, the resin was washed with phosphate buffered saline (PBS) and the resin was stripped with PBS+200 mM imidazole to determine the amount of captured of eGFP-LPETG-SpyTag. eGFP concentrations were determined by measuring the absorbance at 488 nm ($\varepsilon=56,000$ $M^{-1}$ $cm^{-1}$). Both resins retained their maximum capture efficiency of ~80% when their target protein concentration was as low as 0.5 µM, as shown in FIG. 12.

Example 29: Proximity-Based Sortase Ligation Release Over Time

Figure 13A:
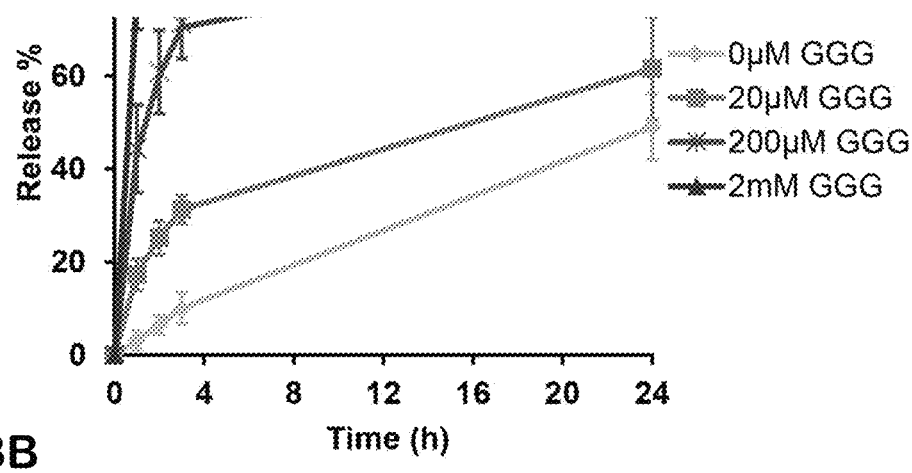
FIGS. 13A and 13B. Proximity-based Sortase Ligation release over time. The sortase reaction was initiated in (FIG. 13A) SpyCatcher-SrtA-His or (FIG. 13B) SrtA-SpyCatcher-His resin containing captured eGFP-LPETG-SpyTag with PBS+50 µM $CaCl_2$+ the indicated GGG concentrations at 37° C. At the indicated time-points, the released eGFP were eluted and then the resin was stripped with PBS+200 mM imidazole to determine the amount of eGFP still on the resin. eGFP concentrations were determined by measuring the absorbance at 488 nm ($\varepsilon$=56,000 $M^{-1}$ $cm^{-1}$). The OpM GGG condition tracks the hydrolysis reaction which results in the unwanted eGFP-LPETG side product. For both the Spy- Catcher-SrtA-His resin and SrtA-Spycatcher-His resin, the estimated ligation efficiency is >95% with 200 µM GGG and 2 mM GGG.
Figure 13B:
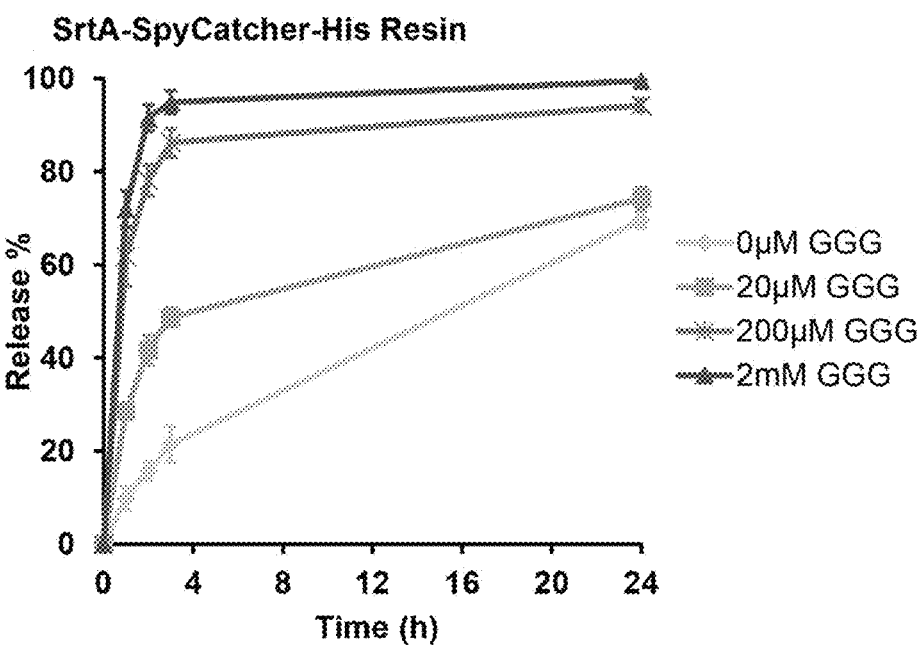

The sortase reaction was initiated in A) SpyCatcher-SrtA-His or B) SrtA-SpyCatcher-His resin containing captured eGFP-LPETG-SpyTag with PBS+50 µM $CaCl_2$+ the indicated GGG concentrations at 37° C. At the indicated timepoints, the released eGFP were eluted and then the resin was stripped with PBS+200 mM imidazole to determine the amount of eGFP still on the resin. eGFP concentrations were determined by measuring the absorbance at 488 nm ($\varepsilon=56,000$ $M^{-1}$ $cm^{-1}$). The 0 µM GGG condition tracks the hydrolysis reaction which results in the unwanted eGFP-LPETG side product. For SpyCatcher-SrtA-His resin (FIG. 13A) and SrtA-Spycatcher-His resin (FIG. 13B), the estimated ligation efficiency is >95% with 200 µM GGG and 2 mM GGG.

Example 30: PBSL vs. Traditional Sortase vs. Sortase Tag Expressed Protein Ligation (STEPL)

FIG. 14A is an SDS-PAGE showing scFv constructs before and after sortase-mediated ligation to the fluorescent peptide GGGSK-TMR, using the PBSL approach (lanes 1 and 2), the traditional sortase approach (lanes 3 and 4-9), and STEPL (lane 10). The traditional sortase reaction was carried out using a sortase:scFv molar ratio ranging from 1:1 to 100:1. FIG. 14B is a fluorescent image of the SDS-PAGE gel. Ligation of the scFv to the peptide GGGSK-TMR is easily detectable via TMR fluorescence. Even with the enormous excess of sortase used in the traditional reaction, only 50-60% of the scFv was fluorescently labeled (i.e. scFv-TMR). In contrast, with PBSL, the efficiency of ligation was ~100%, with no noticeable scFv still linked to the SpyCatcher-Sortase-HisTag construct. With STEPL, the direct fusion of the scFv to sortase interfered with normal protein expression and/or folding. As a result, no labeled protein, scFv-TMR, was detectable. (The scFv-TMR produced by the traditional sortase reaction runs slightly higher than the same product produced via PBSL due to the presence of an additional GGGS linker, prior to LPETG, in the expression plasmid.)

Figure 15:
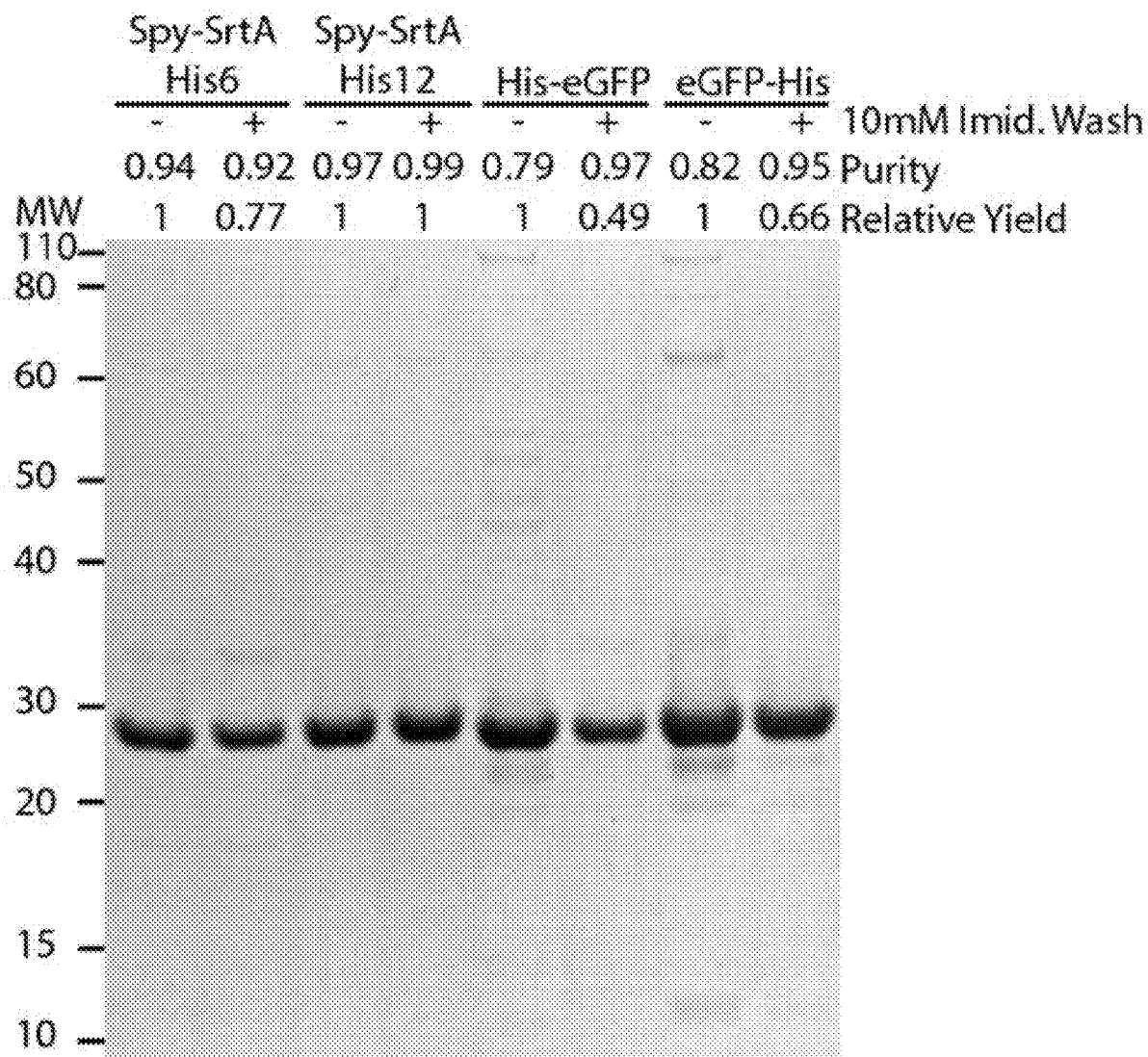
FIG. 15. Comparison of eGFP purity and yield with PBSL versus His-tag and $Co^{2+}$ resin. eGFP-LPETG-SpyTag was purified with PBSL using either SpyCatcher-SrtA-His$_6$ or SpyCatcher-SrtA-His$_{12}$ resin. His$_6$-eGFP or eGFP-His$_6$ was purified using $Co^{2+}$ resin. For all purifications, either PBS or PBS+10 mM imidazole was used to wash the resin prior to elution. As expected, PBS+10 mM imidazole washes improves purity for His-tagged eGFP at the cost of a significant decrease in yield relative to PBS only washes. PBSL using SpyCatcher-SrtA-His$_{12}$, on the other hand, not only had greater purity than His-tagged eGFP with PBS only washes, but also had no decrease in yield after washing with PBS+10 mM imidazole.
Figure 16A:
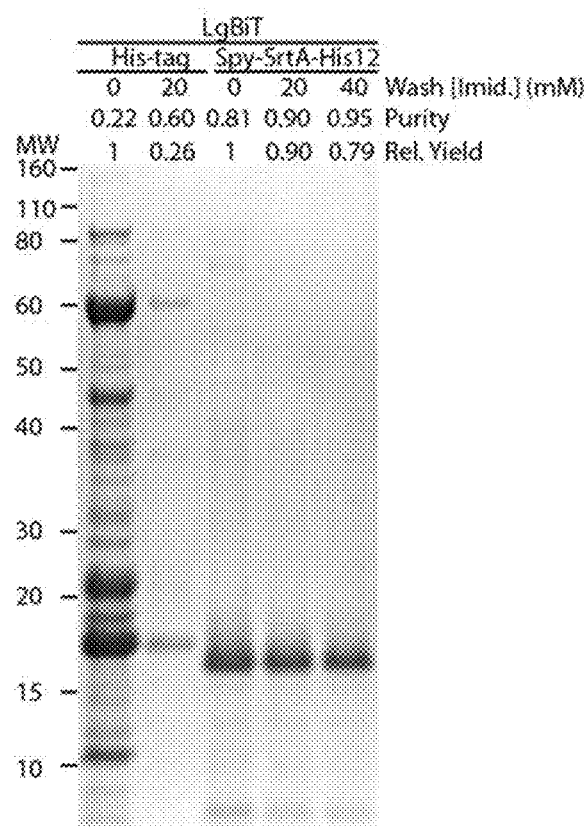
FIG. 16A-16B. Additional comparisons of protein purity and yield between PBSL and His-tag.
Figure 16B:
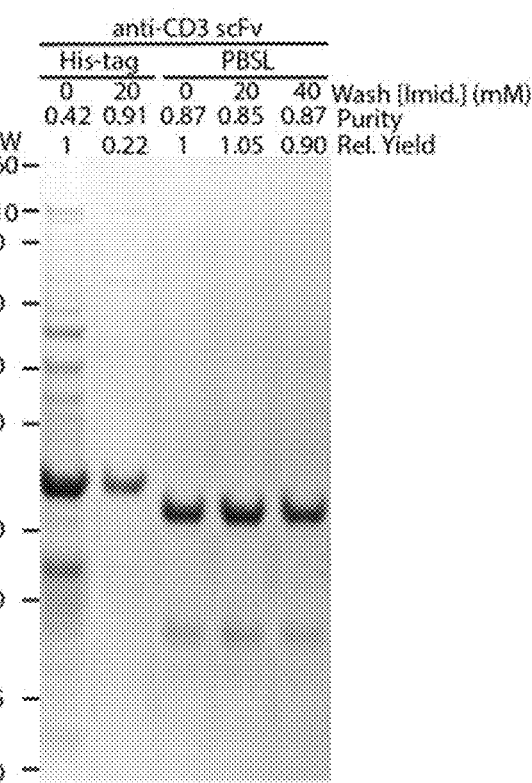

Example 31: Proximity-Based Sortase Mediated Purification of eGFP, with a His12 Affinity Tag The proximity-based sortase system can be used simply for protein purification if ligation to a peptide/protein is not desired. For protein purification applications, the protein of interest can be released from the affinity column upon adding calcium with or without glycine (or a peptide/protein with an N-terminal glycine). The protein of interest is typically of high purity since any other proteins that are non-specifically bound to the affinity column are not released upon sortase-mediated cleavage/hydrolysis. To improve the purity level even further, an affinity tag can be introduced into the proximity-based sortase system that has exceptional affinity (or is covalently bound) to the affinity column. One such example involves using a His12 tag as opposed to a His6 tag. For traditional purification methods, a His6 tag is often used for protein purification applications because a longer His tag (e.g. His12) is not easily released from the affinity column. Therefore, harsh conditions must be used to release the protein of interest from the affinity column, which can damage/denature the protein of interest. The challenge of using the more conventional His6 tag is that only mild washing conditions can be used. As a result, when the protein of interest is released from the column, with imidazole, many proteins that are still non-specifically bound to the resin are also released (FIGS. 15 and 16). Therefore, the purity level is poor. If slightly more stringent washing conditions (i.e. with imidazole) are used, purity is improved, but the relative yield of the purified protein is significantly reduced since a lot of protein of interest is lost during the washing steps.

When a His12 tag was introduced into the proximity-based sortase system, imidazole washes could be used to remove proteins that were non-specifically bound to the affinity column, prior to release of the protein of interest via sortased-mediated cleavage. This led to an improvement in purity of the final recovered protein (FIGS. 15 and 16), compared with conventional HisTag purification. Importantly, no protein of interest was lost during these wash steps, i.e. the yield of the recovered protein of interest remained the same with and without the imidazole washes.

When an imidazole wash was used with the proximity-based system that included a His6 tag, the purity of the final recovered protein of interest was generally higher than when imidazole washes were not performed; however, the relative yield of the recovered protein of interest was significantly reduced (FIGS. 15 and 16).

Figure 17A:
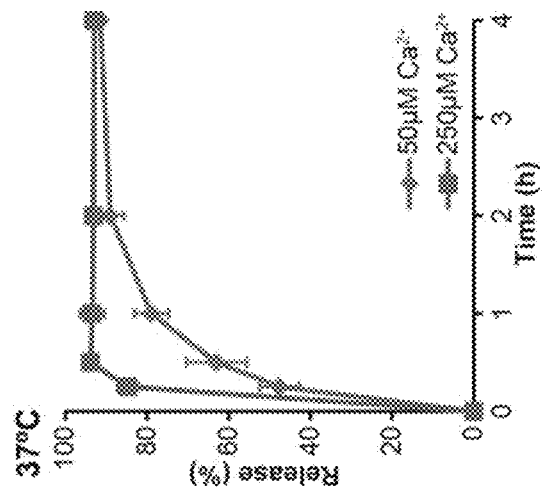
FIG. 17A-17C. PBSL release over time with varying $Ca^{2+}$. The sortase reaction was initiated in SpyCatcher-SrtA-His$_6$ resin containing captured eGFP-LPETG-SpyTag with PBS+2 mM GGG+50 µM or 250 µM $Ca^{2+}$ at (FIG. 17A) 4° C., (FIG. 17B) 25° C., or (FIG. 17C) 37° C. At the indicated time-points, the released eGFP were eluted and then the resin was stripped with PBS+200 mM imidazole to determine the amount of eGFP still on the resin. eGFP concentrations were determined by measuring the absorbance at 488 nm ($\varepsilon$=56,000 $M^{-1}$ $cm^{-1}$). For all temperatures, using 250 µM $Ca^{2+}$ resulted in faster release kinetics. Furthermore, the sortase reaction in PBSL can result in both high release efficiency as well as short reaction times at a broad range of temperatures. ~90% release efficiency can be achieved using PBS+2 mM GGG+250 µM $Ca^{2+}$ within (FIG. 17A) 3 h at 4° C., (FIG. 17B) 30 min at 25° C., and (FIG. 17C) 30 min at 37° C.
Figure 17B:
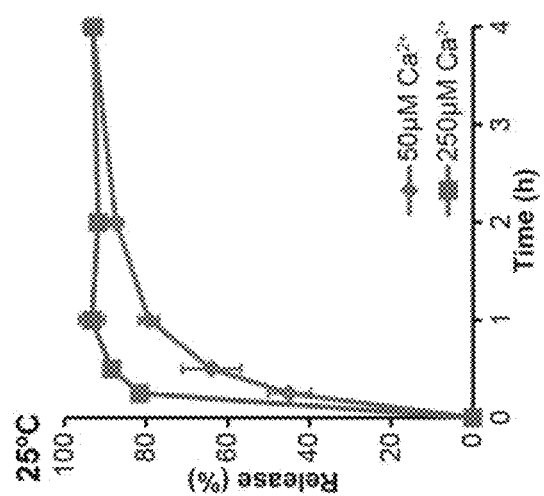
Figure 17C:
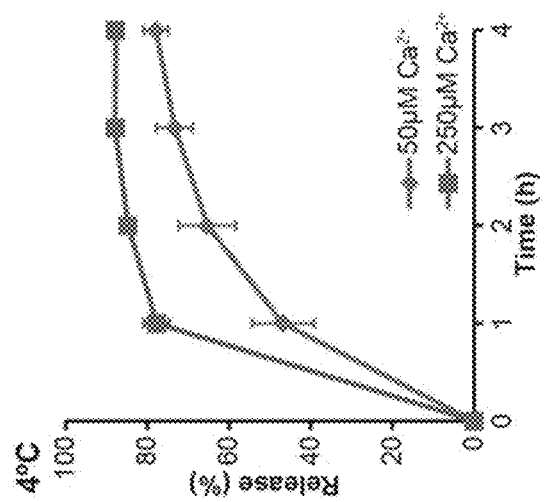

Example 32: Kinetics of Proximity-Based Sortase-Mediated Purification as a Function of Calcium Concentration When purifying proteins from an affinity column, it is often desirable to release and recover the purified protein of interest quickly. It was found that release of a protein of interest from an affinity column in the proximity-based sortase system is dependent on both calcium concentration and temperature (FIG. 17). The protein of interest was released more quickly at higher temperatures and with higher calcium concentrations. More than 80% of the protein of interest was released from the affinity column in just 15 min at both 25° C. and 37° C., when 250 μM of calcium was used. Approximately 80% or more of the protein of interest was released from the affinity column in 1 hour at 4° C. and 250 μM of calcium.

Figure 18:
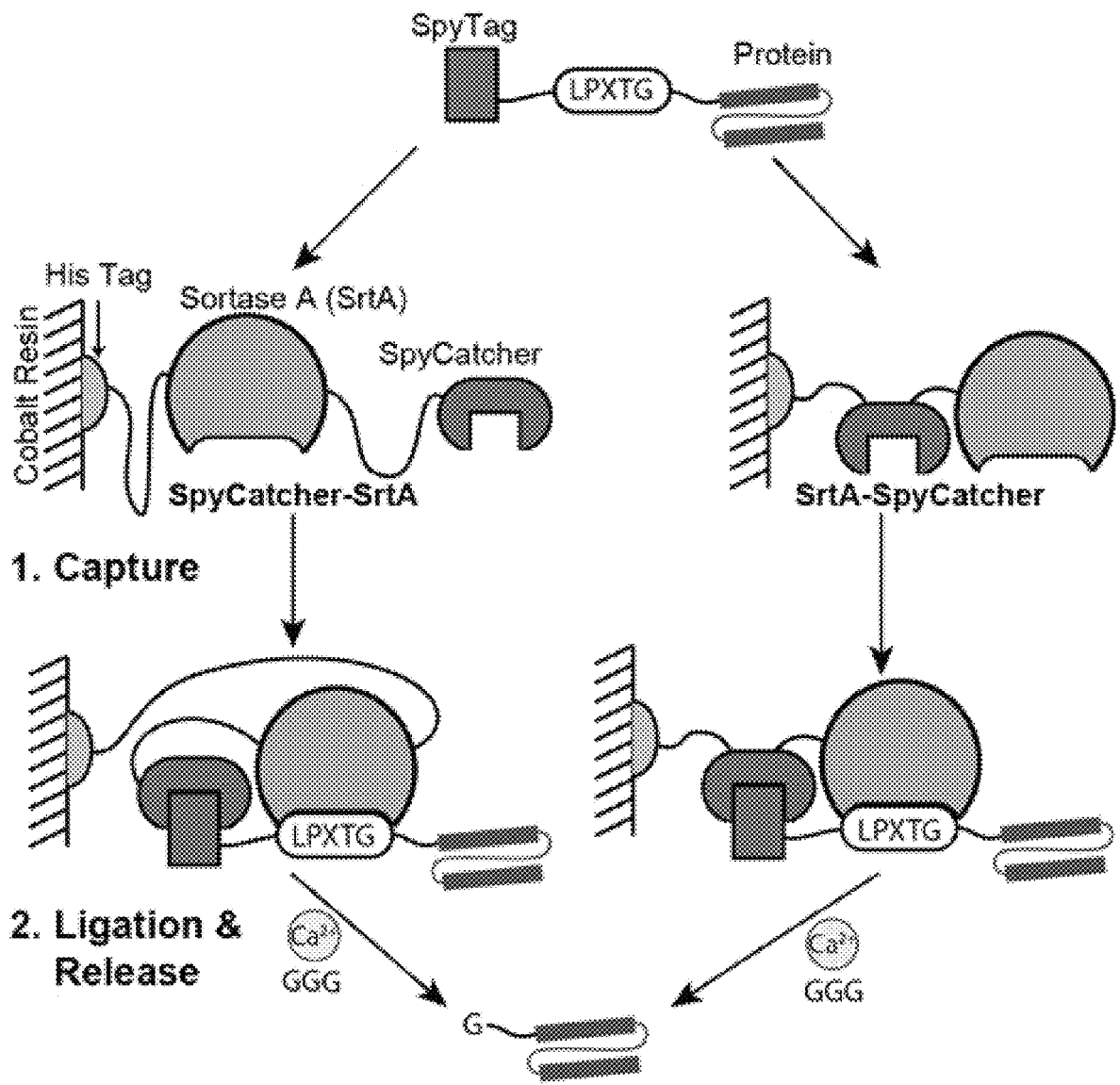
FIG. 18. Schematics of Proximity-based Sortase purification on a Solid Support. (A) A biomolecule of interest is expressed in frame with a sortase recognition motif (e.g., LPXTG) and one member of a binding pair (Binding Partner A). In some embodiments, the first binding pair partner is N-terminal to the sortase recognition sequence and the sortase recognition sequence is N-terminal to the protein of interest. In parallel, a sortase enzyme is expressed in frame with a second member of a binding pair (Binding Partner B) and an affinity tag. The affinity tag can be at the N- or C-terminus of the sortase-binding pair fusion protein (N-terminal affinity tag shown). The sortase construct can be bound to an affinity column or beads. The biomolecule is captured by the sortase construct via interaction of the binding pairs. The biomolecule is subsequently released from the affinity column upon adding glycine or a peptide/protein with an N-terminal glycine. Proximity-based sortase purification can be performed when sortase is expressed between the second member of a binding pair and the affinity tag or when the second member of the binding pair is expressed between sortase and the affinity tag.
Figure 19:
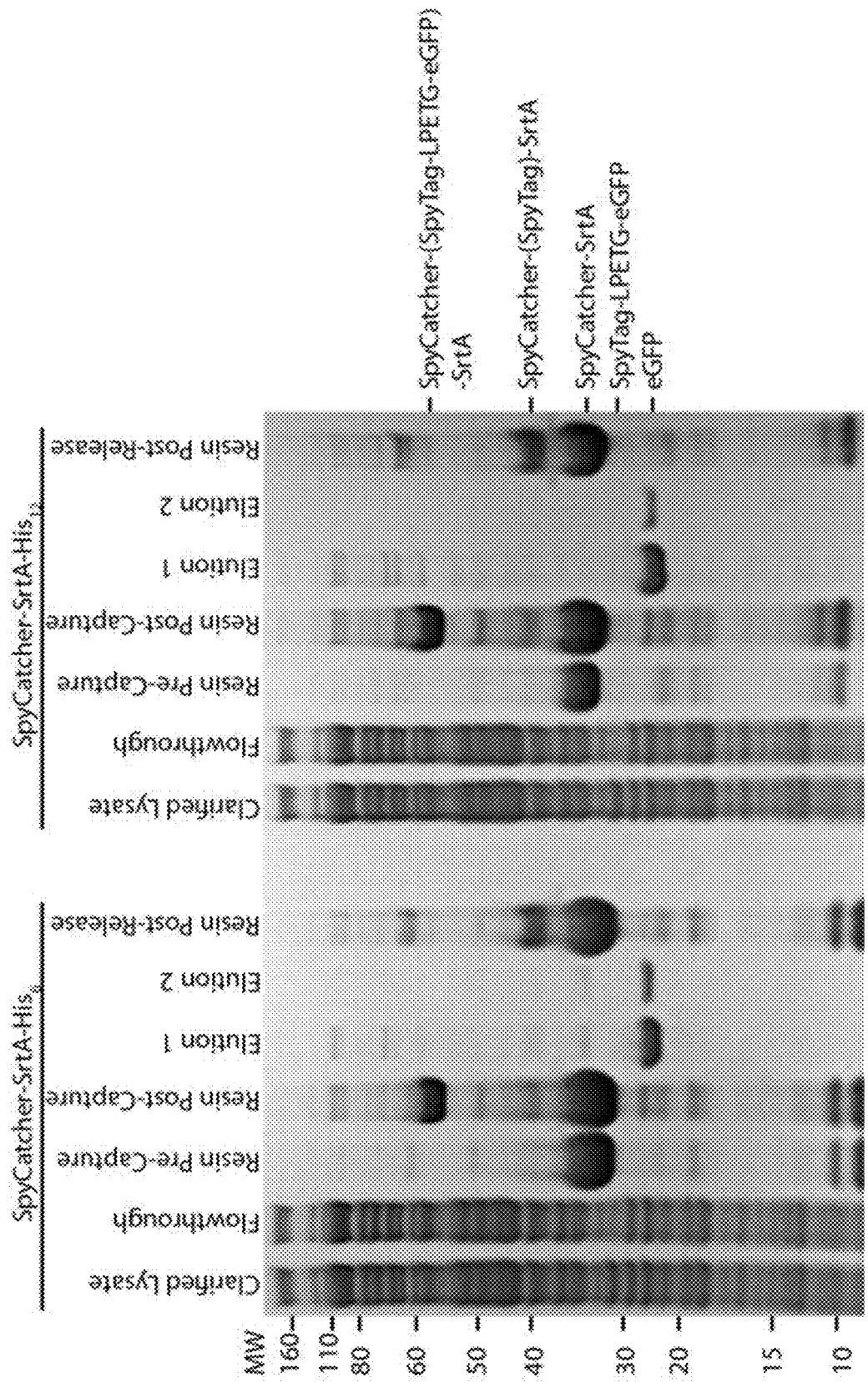
FIG. 19. SpyTag-LPETG-eGFP Purification. Purification of SpyTag-LPETG-eGFP with SpyCatcher-SrtA-His$_6$ or SpyCatcher-SrtA-His$_{12}$ resin was analyzed by Coomasie staining. Clarified lysates containing SpyTag-LPETG-eGFP were incubated with the indicated resin at room temperature for 10 minutes. SpyTag-SpyCatcher isopeptide bond formation results in the formation of a new ~60 kDa protein species. Following capture, the resin was washed with 2 column volumes of either PBS (SpyCatcher-SrtA-His$_6$) or PBS+20 mM imidazole (SpyCatcher-SrtA-His$_{12}$). The sortase reaction was then initiated by incubating the resin with PBS+250 µM $Ca^{21}$+2 mM GGG at 25° C. for 2 hours, resulting in cleavage of the sortase motif to obtain the final ~30 kDa eGFP product.

Example 33: Proximity-Based Sortase-Mediated Purification of Proteins Possessing an N-Terminal Binding Pair Partner and Sortase Recognition Sequence Sometimes it is not possible to fuse peptides/proteins to the C-terminus of a protein of interest. Therefore, a proximity-based sortase-mediated purification system was developed with the first binding pair partner and sortase recognition sequence fused to the N-terminus of the protein of interest (FIG. 18). In this system, the fusion protein can be captured on an affinity column that has been functionalized with the second binding pair partner and sortase fusion protein. Adding calcium alone or in combination with glycine or a peptide/protein with an N-terminal glycine leads to release of the purified protein of interest from the affinity column (FIG. 19). The efficiency in which the expressed protein of interest is captured by second binding pair partner-sortase fusion protein, on the affinity column, is >60% within 5 min.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A vector comprising a polynucleotide encoding a first protein, wherein:

said first protein comprises a protein of interest in series with a sortase recognition sequence and a first binding pair partner; wherein:

said protein of interest is N-terminal and connected via a linker to said sortase recognition sequence and said sortase recognition sequence is N-terminal and connected via a linker to said first binding pair partner; or said first binding pair partner is N-terminal and connected via a linker to said sortase recognition sequence and said sortase recognition sequence is N-terminal and connected via a linker to said protein of interest;

wherein said first binding pair partner comprises one member of a pair of protein moieties that form a heterodimer, and wherein said pair of protein moieties that form a heterodimer is selected from the group consisting of SpyCatcher and SpyTag; two complementary halves of a split intein; c-Jun and c-Fos; leucine zippers; split adhesin domains; SnoopCatcher and SnoopTag; S-protein and S-Tag; Streptavidin/Streptactin and Strep-tag or Strep-tag II; calmodulin and calmodulin binding peptide; and a binding pair of a dock-and-lock system, and wherein the sortase recognition sequence is selected from the group consisting of LPXTG (SEQ ID NO: 1), LPKTG (SEQ ID NO: 2), LPATG (SEQ ID NO: 3), LPNTG (SEQ ID NO: 4), LPETG (SEQ ID NO: 5), LPXAG (SEQ ID NO: 6), LPNAG SEQ ID NO: 7), LPXTA (SEQ ID NO: 8), LPNTA (SEQ ID NO: 9), LGXTG (SEQ ID NO: 10), LGATG (SEQ ID NO: 11), IPXTG (SEQ ID NO: 12), IPNTG (SEQ ID NO: 13), IPETG (SEQ ID NO: 14), NPQTN (SEQ ID NO: 15), LAXTG (SEQ ID NO: 16), LPXSG (SEQ ID NO: 17), LSETG (SEQ ID NO: 18), LPXCG (SEQ ID NO: 19), and XPETG (SEQ ID NO: 21).

2. A vector comprising a polynucleotide encoding a second protein, wherein:

said second protein comprises a second binding pair partner in series with a sortase and a first affinity tag having a selective affinity for a first affinity tag resin, wherein:

said second binding pair partner is N-terminal and connected via a linker to said sortase and said sortase is N-terminal and connected via a linker to said first affinity tag; or said sortase is N-terminal and connected via a linker to said second binding pair partner and said second binding pair partner is N-terminal and connected via a linker to said first affinity tag; or said first affinity tag is N-terminal and connected via a linker to said second binding pair partner and said second binding pair partner is N-terminal and connected via a linker to said sortase; or said first affinity tag is N-terminal and connected via a linker to said sortase and said sortase is N-terminal and connected via a linker to said second binding pair partner wherein said second binding pair partner comprises one member of a pair of protein moieties that form a heterodimer, and wherein said pair of protein moieties that form a heterodimer is selected from the group consisting of SpyCatcher and SpyTag; two complementary halves of a split intein; c-Jun and c-Fos; leucine zippers; split adhesin domains; SnoopCatcher and SnoopTag; S-protein and S-Tag; Streptavidin/Streptactin or a variant thereof and Strep-tag or Strep-tag II; calmodulin and calmodulin binding peptide; and a binding pair of a dock-and-lock system, and wherein said sortase is selected from the group consisting of sortase A (SrtA), sortase B (SrtB), sortase C (SrtC), sortase D (SrtD), sortase E (SrtE), and sortase F (SrtF).

3. A cell comprising the vector of claim 1 for recombinantly expressing the first protein, wherein said cell is a bacterial cell, a yeast cell, an insect cell, or a mammalian cell.

4. A cell comprising the vector of claim 2 for recombinantly expressing the second protein, wherein said cell is a bacterial cell, a yeast cell, an insect cell, or a mammalian cell.

5. The vector of claim 1, wherein said first protein further comprises a second affinity tag having a selective affinity for a second affinity tag resin.

6. The vector of claim 5, wherein the second affinity tag is selected from the group consisting of a histidine tag (His tag), a chitin-binding domain, a calmodulin tag, a polyglutamate tag, a maltose binding protein, glutathione-S-transferase, an S-tag, SBP-tag, Strep-tag, Strep-tag II, green fluorescent protein-tag, thioredoxin tag, Nus-tag, Fc-tag, Halo-tag, FLAG-tag, V5-tag, VSV-tag, Xpress tag, E-tag, Myc-tag, HA-tag, Softag, NE-tag, biotin (via biotin ligase), BirA, AviTag, BCCP (biotin carboxyl carrier protein), Spy-Tag, SpyCathcher, SnoopTag, and SnoopCatcher.

7. The vector of claim 2, wherein the first affinity tag is selected from the group consisting of a histidine tag (His tag), a chitin-binding domain, a calmodulin tag, a polyglutamate tag, a maltose binding protein, glutathione-S-transferase, an S-tag, SBP-tag, Strep-tag, Strep-tag II, green fluorescent protein-tag, thioredoxin tag, Nus-tag, Fc-tag, Halo-tag, FLAG-tag, V5-tag, VSV-tag, Xpress tag, E-tag, Myc-tag, HA-tag, Softag, NE-tag, biotin (via biotin ligase), BirA, AviTag, BCCP, SpyTag, SpyCathcher, SnoopTag, and SnoopCatcher.

* * * * *

SEQUENCE LISTING

```
<160> NUMBER OF SEQ ID NOS: 31

<210> SEQ ID NO 1
<211> LENGTH: 5
<212> TYPE: PRT
<213> ORGANISM: artificial sequence
<220> FEATURE:
<223> OTHER INFORMATION: sortase recognition sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1

Leu Pro Xaa Thr Gly
1               5

<210> SEQ ID NO 2
<211> LENGTH: 5
<212> TYPE: PRT
<213> ORGANISM: artificial sequence
<220> FEATURE:
<223> OTHER INFORMATION: sortase recognition sequence

<400> SEQUENCE: 2
```

```
Leu Pro Lys Thr Gly
1               5

<210> SEQ ID NO 3
<211> LENGTH: 5
<212> TYPE: PRT
<213> ORGANISM: artificial sequence
<220> FEATURE:
<223> OTHER INFORMATION: sortase recognition sequence

<400> SEQUENCE: 3

Leu Pro Ala Thr Gly
1               5

<210> SEQ ID NO 4
<211> LENGTH: 5
<212> TYPE: PRT
<213> ORGANISM: artificial sequence
<220> FEATURE:
<223> OTHER INFORMATION: sortase recognition sequence

<400> SEQUENCE: 4

Leu Pro Asn Thr Gly
1               5

<210> SEQ ID NO 5
<211> LENGTH: 5
<212> TYPE: PRT
<213> ORGANISM: artificial sequence
<220> FEATURE:
<223> OTHER INFORMATION: sortase recognition sequence

<400> SEQUENCE: 5

Leu Pro Glu Thr Gly
1               5

<210> SEQ ID NO 6
<211> LENGTH: 5
<212> TYPE: PRT
<213> ORGANISM: artificial sequence
<220> FEATURE:
<223> OTHER INFORMATION: sortase recognition sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 6

Leu Pro Xaa Ala Gly
1               5

<210> SEQ ID NO 7
<211> LENGTH: 5
<212> TYPE: PRT
<213> ORGANISM: artificial sequence
<220> FEATURE:
<223> OTHER INFORMATION: sortase recognition sequence

<400> SEQUENCE: 7

Leu Pro Asn Ala Gly
1               5

<210> SEQ ID NO 8
<211> LENGTH: 5
<212> TYPE: PRT
<213> ORGANISM: artificial sequence
<220> FEATURE:
```

```
<223> OTHER INFORMATION: sortase recognition sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 8

Leu Pro Xaa Thr Ala
1               5

<210> SEQ ID NO 9
<211> LENGTH: 5
<212> TYPE: PRT
<213> ORGANISM: artificial sequence
<220> FEATURE:
<223> OTHER INFORMATION: sortase recognition sequence

<400> SEQUENCE: 9

Leu Pro Asn Thr Ala
1               5

<210> SEQ ID NO 10
<211> LENGTH: 5
<212> TYPE: PRT
<213> ORGANISM: artificial sequence
<220> FEATURE:
<223> OTHER INFORMATION: LGXTG
<220> FEATURE:
<221> NAME/KEY: misc_feature
<222> LOCATION: (3)..(3)
<223> OTHER INFORMATION: Xaa can be any naturally occurring amino acid

<400> SEQUENCE: 10

Leu Gly Xaa Thr Gly
1               5

<210> SEQ ID NO 11
<211> LENGTH: 5
<212> TYPE: PRT
<213> ORGANISM: artificial sequence
<220> FEATURE:
<223> OTHER INFORMATION: sortase recognition sequence

<400> SEQUENCE: 11

Leu Gly Ala Thr Gly
1               5

<210> SEQ ID NO 12
<211> LENGTH: 5
<212> TYPE: PRT
<213> ORGANISM: artificial sequence
<220> FEATURE:
<223> OTHER INFORMATION: sortase recognition sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Ile Pro Xaa Thr Gly
1               5

<210> SEQ ID NO 13
<211> LENGTH: 5
<212> TYPE: PRT
<213> ORGANISM: artificial sequence
<220> FEATURE:
<223> OTHER INFORMATION: sortase recognition sequence
```

```
<400> SEQUENCE: 13

Ile Pro Asn Thr Gly
1               5

<210> SEQ ID NO 14
<211> LENGTH: 5
<212> TYPE: PRT
<213> ORGANISM: artificial sequence
<220> FEATURE:
<223> OTHER INFORMATION: sortase recognition sequence

<400> SEQUENCE: 14

Ile Pro Glu Thr Gly
1               5

<210> SEQ ID NO 15
<211> LENGTH: 5
<212> TYPE: PRT
<213> ORGANISM: artificial sequence
<220> FEATURE:
<223> OTHER INFORMATION: sortase recognition sequence

<400> SEQUENCE: 15

Asn Pro Gln Thr Asn
1               5

<210> SEQ ID NO 16
<211> LENGTH: 5
<212> TYPE: PRT
<213> ORGANISM: artificial sequence
<220> FEATURE:
<223> OTHER INFORMATION: sortase recognition sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 16

Leu Ala Xaa Thr Gly
1               5

<210> SEQ ID NO 17
<211> LENGTH: 5
<212> TYPE: PRT
<213> ORGANISM: artificial sequence
<220> FEATURE:
<223> OTHER INFORMATION: sortase recognition sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 17

Leu Pro Xaa Ser Gly
1               5

<210> SEQ ID NO 18
<211> LENGTH: 5
<212> TYPE: PRT
<213> ORGANISM: artificial sequence
<220> FEATURE:
<223> OTHER INFORMATION: sortase recognition sequence

<400> SEQUENCE: 18

Leu Ser Glu Thr Gly
1               5
```

```
<210> SEQ ID NO 19
<211> LENGTH: 5
<212> TYPE: PRT
<213> ORGANISM: artificial sequence
<220> FEATURE:
<223> OTHER INFORMATION: sortase recognition sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 19

Leu Pro Xaa Cys Gly
1               5

<210> SEQ ID NO 20
<211> LENGTH: 5
<212> TYPE: PRT
<213> ORGANISM: artificial sequence
<220> FEATURE:
<223> OTHER INFORMATION: sortase recognition sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20

Leu Pro Xaa Ala Gly
1               5

<210> SEQ ID NO 21
<211> LENGTH: 5
<212> TYPE: PRT
<213> ORGANISM: artificial sequence
<220> FEATURE:
<223> OTHER INFORMATION: sortase recognition sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 21

Xaa Pro Glu Thr Gly
1               5

<210> SEQ ID NO 22
<211> LENGTH: 61
<212> TYPE: PRT
<213> ORGANISM: Staphylococcal  aureus

<400> SEQUENCE: 22

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Met Arg Met
    50                  55                  60

<210> SEQ ID NO 23
<211> LENGTH: 56
<212> TYPE: PRT
<213> ORGANISM: artificial sequence
<220> FEATURE:
<223> OTHER INFORMATION: hypothermophilic variant of a B1 domain derived
      from Streptococcal Protein G
```

<400> SEQUENCE: 23

Met Thr Phe Lys Leu Ile Ile Asn Gly Lys Thr Leu Lys Gly Glu Ile
1               5                   10                  15

Thr Ile Glu Ala Val Asp Ala Ala Glu Ala Glu Lys Ile Phe Lys Gln
            20                  25                  30

Tyr Ala Asn Asp Tyr Gly Ile Asp Gly Glu Trp Thr Tyr Asp Asp Ala
        35                  40                  45

Thr Lys Thr Phe Thr Val Thr Glu
    50                  55

<210> SEQ ID NO 24
<211> LENGTH: 7
<212> TYPE: PRT
<213> ORGANISM: artificial sequence
<220> FEATURE:
<223> OTHER INFORMATION: sortase recognition motif

<400> SEQUENCE: 24

Leu Pro Glu Thr Gly Gly Gly
1               5

<210> SEQ ID NO 25
<211> LENGTH: 15
<212> TYPE: PRT
<213> ORGANISM: artificial sequence
<220> FEATURE:
<223> OTHER INFORMATION: (GGS)5 linker

<400> SEQUENCE: 25

Gly Gly Ser Gly Gly Ser Gly Gly Ser Gly Gly Ser Gly Gly Ser
1               5                   10                  15

<210> SEQ ID NO 26
<211> LENGTH: 6
<212> TYPE: PRT
<213> ORGANISM: artificial sequence
<220> FEATURE:
<223> OTHER INFORMATION: (GGS)2 linker

<400> SEQUENCE: 26

Gly Gly Ser Gly Gly Ser
1               5

<210> SEQ ID NO 27
<211> LENGTH: 9
<212> TYPE: PRT
<213> ORGANISM: artificial sequence
<220> FEATURE:
<223> OTHER INFORMATION: (GGS)3 LINKER

<400> SEQUENCE: 27

Gly Gly Ser Gly Gly Ser Gly Gly Ser
1               5

<210> SEQ ID NO 28
<211> LENGTH: 4
<212> TYPE: PRT
<213> ORGANISM: artificial sequence
<220> FEATURE:
<223> OTHER INFORMATION: peptide tag

<400> SEQUENCE: 28

Gly Gly Gly Lys
1

```
<210> SEQ ID NO 29
<211> LENGTH: 23
<212> TYPE: PRT
<213> ORGANISM: artificial sequence
<220> FEATURE:
<223> OTHER INFORMATION: (GGS)2-SGGGS-(GGS)4 linker

<400> SEQUENCE: 29

Gly Gly Ser Gly Gly Ser Ser Gly Gly Gly Ser Gly Gly Ser Gly Gly
1               5                   10                  15

Ser Gly Gly Ser Gly Gly Ser
            20

<210> SEQ ID NO 30
<211> LENGTH: 5
<212> TYPE: PRT
<213> ORGANISM: artificial sequence
<220> FEATURE:
<223> OTHER INFORMATION: peptide linker

<400> SEQUENCE: 30

Gly Gly Ser Ser Lys
1               5

<210> SEQ ID NO 31
<211> LENGTH: 4
<212> TYPE: PRT
<213> ORGANISM: artificial sequence
<220> FEATURE:
<223> OTHER INFORMATION: linker

<400> SEQUENCE: 31

Gly Gly Gly Ser
1
```